(12) United States Patent
Wei et al.

(10) Patent No.: US 11,624,077 B2
(45) Date of Patent: Apr. 11, 2023

(54) GENE KNOCKOUT METHOD

(71) Applicants: PEKING UNIVERSITY, Beijing (CN); EDIGENE BIOTECHNOLOGY INC., Beijing (CN)

(72) Inventors: Wensheng Wei, Beijing (CN); Yiou Chen, Beijing (CN); Yuexin Zhou, Beijing (CN); Hongmin Zhang, Beijing (CN); Pengfei Yuan, Beijing (CN); Yuan Liu, Beijing (CN)

(73) Assignees: Peking University, Beijing (CN); Edigene Biotechnology Inc., Beijing (CN)

( * ) Notice: Subject to any disclaimer, the term of this patent is extended or adjusted under 35 U.S.C. 154(b) by 191 days.

(21) Appl. No.: 16/637,591

(22) PCT Filed: Aug. 8, 2017

(86) PCT No.: PCT/CN2017/096510
§ 371 (c)(1),
(2) Date: Feb. 7, 2020

(87) PCT Pub. No.: WO2019/028686
PCT Pub. Date: Feb. 14, 2019

(65) Prior Publication Data
US 2020/0255866 A1    Aug. 13, 2020

(51) Int. Cl.
*C12N 15/90* (2006.01)
*C12N 9/22* (2006.01)
*C12N 15/11* (2006.01)
*C12N 15/65* (2006.01)
*G01N 21/64* (2006.01)

(52) U.S. Cl.
CPC .............. *C12N 15/90* (2013.01); *C12N 9/22* (2013.01); *C12N 15/111* (2013.01); *C12N 15/65* (2013.01); *G01N 21/6428* (2013.01); *C12N 2310/3517* (2013.01)

(58) Field of Classification Search
CPC .................... C12N 15/65; C12N 2310/20
See application file for complete search history.

(56) References Cited

U.S. PATENT DOCUMENTS

| | | | |
|---|---|---|---|
| 8,697,359 B1 | 4/2014 | Zhang | |
| 8,932,814 B2 | 1/2015 | Cong | |
| 10,113,167 B2 | 10/2018 | Doudna et al. | |
| 2014/0134740 A1 | 5/2014 | Gregory et al. | |
| 2014/0273226 A1 | 9/2014 | Wu | |
| 2014/0273233 A1 | 9/2014 | Chen et al. | |
| 2015/0037809 A1 | 2/2015 | Duchateau et al. | |
| 2016/0138094 A1 | 5/2016 | Summerer et al. | |
| 2017/0049909 A1 | 2/2017 | Cullen et al. | |
| 2017/0198302 A1* | 7/2017 | Feng | C12N 15/102 |
| 2021/0054030 A1 | 2/2021 | Wei et al. | |
| 2021/0163936 A1 | 6/2021 | Wei et al. | |
| 2022/0064633 A1 | 3/2022 | Wei et al. | |
| 2022/0186210 A1 | 6/2022 | Wei et al. | |

FOREIGN PATENT DOCUMENTS

| | | |
|---|---|---|
| CN | 103025344 A | 4/2013 |
| CN | 103668472 A | 3/2014 |
| CN | 104651399 A | 5/2015 |
| CN | 105316341 A | 2/2016 |
| CN | 106062197 A | 10/2016 |
| CN | 106232823 A | 12/2016 |
| CN | 106637421 A | 5/2017 |
| CN | 107090466 A | 8/2017 |
| CN | 107513538 A | 12/2017 |
| CN | 107849581 A | 3/2018 |
| EP | 3536796 A1 | 9/2019 |
| JP | 2013529083 A | 7/2013 |
| JP | 2015510772 A | 4/2015 |
| KR | 20160118987 A | 10/2016 |
| WO | 2011146121 A1 | 11/2011 |
| WO | 2013102290 A1 | 7/2013 |
| WO | 2013176772 A1 | 11/2013 |
| WO | 2014018423 A2 | 1/2014 |
| WO | 2014065596 A1 | 5/2014 |
| WO | 2014130955 A1 | 8/2014 |
| WO | 2014144592 A2 | 9/2014 |
| WO | 2014144761 A2 | 9/2014 |
| WO | 2014204724 A1 | 12/2014 |
| WO | 2014206568 A1 | 12/2014 |
| WO | 2016011080 A2 | 1/2016 |
| WO | 2016142719 A1 | 9/2016 |
| WO | 2016182893 A1 | 11/2016 |
| WO | 2016184989 A1 | 11/2016 |
| WO | 2016205745 A2 | 12/2016 |
| WO | 2017214460 A1 | 12/2017 |
| WO | 2018154027 A1 | 8/2018 |
| WO | 2019024081 A1 | 2/2019 |
| WO | 2019191876 A1 | 10/2019 |
| WO | 2020125762 A1 | 6/2020 |
| WO | 2020192712 A1 | 10/2020 |

OTHER PUBLICATIONS

Zhou, Yuexin, Hongmin Zhang, and Wensheng Wei. "Simultaneous generation of multi-gene knockouts in human cells." FEBS letters 590.23 (2016): 4343-4353. (Year: 2016).*

International Search Report, dated May 14, 2018, for PCT Application No. PCT/CN2017/096510, English Translation, 2 pages.

Zhou, Y. et al. (2016). "Simultaneous Generation of Multi-Gene Knockouts in Human Cells," FEBS Letters 590:4343-4353.

(Continued)

*Primary Examiner* — Weihua Fan
(74) *Attorney, Agent, or Firm* — Morrison & Foerster LLP

(57) ABSTRACT

A donor construct and a gene knockout method, as well as a system and kit for the gene knockout are provided. The donor construct is a linear donor DNA or can be cleaved in a cell to produce the linear donor DNA. The gene knockout method uses a marker gene contained in the donor construct to enrich cells in which a gene is knocked out, thereby improving the efficiency of generating the gene knockout by a sequence-specific nuclease.

33 Claims, 13 Drawing Sheets

Specification includes a Sequence Listing.

(56) References Cited

OTHER PUBLICATIONS

Adamson, B. et al. (2012). "A Genome-Wide Homologous Recombination Screen Identifies The RNA-Binding Protein RBMX as a Component of the DNA-Damage Response," Nat Cell Biol. 14(3):318-328, 27 pages.

Anders, S. et al. (2010). "Differential Expression Analysis For Sequence Count Data," Genome Biol 11:R106, 12 pages.

Auer, T.O. et al. (2014). "CRISPR/Cas9 and TALEN-Mediated Knock-In Approaches In Zebrafish," Methods, 9 pages.

Ausubel, F. et al. (1987). Current Protocols in Molecular Biology, Greene Publishing and Wiley Interscience, New York, TOC, 7 pages.

Billon, P. et al. (Sep. 21, 2017). "CRISPR-Mediated Base Editing Enables Efficient Disruption of Eukaryotic Genes through Induction of STOP Codons," Mol Cell 67:1068-1079.

Black, D.L. (2003). Mechanisms of Alternative Pre-Messenger RNA Splicing. Annual Review of Biochemistry. 72:291-336, 64 pages.

Boch, J. et al. (2010, e-pub. May 10, 2010). "Xanthomonas AvrBs3 Family-Type III Effectors: Discovery and Function," Annu Rev Phytopathol 48:419-436.

Boch, J. et al. (Dec. 11, 2009). "Breaking The Code Of DNA Binding Specificity Of TAL-Type III Effectors," Science 326(5959):1509-1512.

Bogdanove, A.J. et al. (Sep. 30, 2011). "TAL Effectors: Customizable Proteins For DNA Targeting," Science 333(6051):1843-1846.

Bradley, K.A. et al. (Nov. 8, 2001). "Identification Of The Cellular Receptor For Anthrax Toxin," Nature 414:225-229.

Bultmann, S. et al. (2012, e-pub. Mar. 2, 2012). "Targeted Transcriptional Activation of Silent oct4 Pluripotency Gene By Combining Designer TALEs and Inhibition of Epigenetic Modifiers," Nucleic Acids Res 40(12):5368-5377.

Burkard, M.E. et al. (Mar. 15, 2012). "Enabling and Disabling Polo-Like Kinase 1 Inhibition Through Chemical Genetics," ACS Chemical Biology 7:978-981.

Canver, M.C. et al. (2015). "BCL11A Enhancer Dissection By Cas9-Mediated In Situ Saturating Mutagenesis," Nature 527:192-197.

Chapman, J.R. et al. (Aug. 24, 2012). "Playing The End Game: DNA Double-Strand Break Repair Pathway Choice," Mol. Cell. 47:497-510.

Chen, B. et al. (Dec. 19, 2013). "Dynamic Imaging of Genomic Loci In Living Human Cells By an Optimized CRISPR/Cas System," Cell 155:1479-1491.

Chen, D. et al. (2011). "Bortezomib as The First Proteasome Inhibitor Anticancer Drug: Current Status and Future Perspectives," Curr. Cancer Drug Targets 11:239-253.

Chen, F. et al. (Sep. 2011, e-published on Jul. 17, 2011). "High-Frequency Genome Editing Using ssDNA Oligonucleotides With Zinc-Finger Nucleases," Nature Methods 8(9):753-755.

Christian, M. et al. (Oct. 2010, e-pub. Jul. 26, 2010). "Targeting DNA Double-Strand Breaks With TAL Effector Nucleases," Genetics 186(2):757-761.

Clancy, S. (2008). "RNA Splicing: Introns, Exons and Spliceosome," Nature Education 1:31, 3 pages.

Cong, L. et al. (2012). "Comprehensive Interrogation of Natural TALE DNA-Binding Modules and Transcriptional Repressor Domains," Nat Commun. 3:968, 14 pages.

Cong, L. et al. (Feb. 15, 2013). "Multiplex Genome Engineering Using CRISPR/Cas Systems," Science 339(6121):819-823, 9 pages.

Cristea, S. et al. (2013, e-pub. Oct. 5, 2012). "In vivo Cleavage of Transgene Donors Promotes Nuclease-Mediated Targeted Integration," Biotechnol. & Bioeng. 110(3):871-880.

Crooks, G. E. et al. (2004). "WebLogo: A Sequence Logo Generator," Genome Res. 14:1188-1190.

De Wilt, L.H.A.M. et al. (2012, e-pub. Oct. 18, 2011). "Proteasome-Based Mechanisms of Intrinsic and acquired Bortezomib Resistance In Non-Small Cell Lung Cancer," Biochem. Pharmacol. 83:207-217.

Deng, D. et al. (2012). "Recognition of Methylated DNA By TAL Effectors," Cell research 22(10):1502-1504.

Deng, D. et al. (Feb. 10, 2012, e-pub. Jan. 5, 2012). "Structural Basis For Sequence-Specific Recognition Of DNA By TAL Effectors," Science 335(6069):720-723, 9 pages.

Duan, J. et al. (2004). "Structural and Functional Analysis Of Mutations At The Human Hypoxanthine Phosphoribosyl Transferase (HPRT1) Locus," Human Mutation 23:599-611.

Dupuy, A. et al. (Nov. 13, 2013). Targeted Gene Therapy of Xeroderma Pigmentosum Cells Using Meganuclease and TALEN, PLoS One 8(11):e78678, 8 pages.

Engler, C. et al. (May 14, 2009). "Golden Gate Shuffling: A One-Pot DNA Shuffling Method Based On Type IIs Restriction Enzymes," PLoS One 4:e5553, 9 pages.

Engreitz, J.M. et al. (Nov. 17, 2016). "Local Regulation of Gene Expression by lncRNA Promoters, Transcription and Splicing," Nature 539(7629):452-455, with Supplemental, 19 pages.

Extended European Search Report, dated May 10, 2022, for European Patent Application No. 20777188.2, 10 pages.

Extended European Search Report, dated Oct. 20, 2021, for European Patent Application No. 18913494.3, 10 pages.

Ezkurdia, I. et al. (2014, e-pub. Jun. 16, 2014). "Multiple Evidence Strands Suggest That There May Be as Few as 19,000 Human Protein-Coding Genes," Hum. Mol. Genet. 23:5866-5878.

Fang, G. et al. (Dec. 2012). "Genome-Wide Mapping of Methylated Adenine Residues In Pathogenic *Escherichia coli* Using Single-Molecule Real-Time Sequencing," Nature biotechnology 30(12):1232-1239, 23 pages.

Findlay, G.M. et al. (2014). "Saturation Editing of Genomic Regions By Multiplex Homology-Directed Repair," Nature 513:120-123.

Franke, N.E. et al. (2012, e-pub. Sep. 23, 2011). "Impaired Bortezomib Binding To Mutant β5 Subunit of The Proteasome Is The Underlying Basis For Bortezomib Resistance In Leukemia Cells," Leukemia 26:757-768.

Freshney, R. I., (1987) "Culture of Specific Cell Types" Chapter 20 in Culture of Animal Cells: A Manual of Basic Techniques, Alan R. Liss & Co., New York; pp. 257-260, 270-273.

Fu, S. et al. (Jun. 18, 2010). "The Structure of Tumor Endothelial Marker 8 (TEM8) Extracellular Domain and Implications For Its Receptor Function For Recognizing Anthrax Toxin," PLoS One 5:e11203, 10 pages.

Fu, Y. et al. (May 7, 2015). "N6-Methyldeoxyadenosine Marks Active Transcription Start Sites In Chlamydomonas," Cell 161:1-14.

Fu, Y. et al. (Sep. 2013). "High-Frequency Off-Target Mutagenesis Induced By CRISPR-Cas Nucleases In Human Cells," Nat Biotechnol 31:822-826, 13 pages.

Garg, A. et al. (2012, e-pub. May 11, 2012). "Engineering Synthetic TAL Effectors With Orthogonal Target Sites," Nucleic Acids Res 40(15):7584-7595.

Garst, A.D. et al. (2017, e-pub. Dec. 12, 2016). "Genome-Wide Mapping of Mutations At Single-Nucleotide Resolution For Protein, Metabolic and Genome Engineering," Nat. Biotechnol. 35:48-55.

Genbank NR_110533.1, Shin, S.Y. et al. (Oct. 8, 2016). "*Homo sapiens* DiGeorge Syndrome Critical Region Gene 5 (Non-Protein Coding) (DGCR5). Transcript Variant 3, Non-Coding RNA," 2 pages.

Gilbert, L.A. et al. (Jul. 18, 2013). "CRISPR-Mediated Modular RNA-Guided Regulation Of Transcription In Eukaryotes," Cell 154:442-451.

Gilbert, L.A. et al. (Oct. 23, 2014). "Genome-Scale CRISPR-Mediated Control of Gene Repression and Activation," Cell 159:647-661.

Goyal, A. et al. (2017, e-pub. Sep. 30, 2016). "Challenges of CRISPR/Cas9 Applications For Long Non-Coding RNA Genes," Nucleic Acids Res 45(3):e12, 13 pages.

Greer, E.L. et al. (May 7, 2015). "DNA Methylation on N6-Adenine in C. elegans," Cell 161:868-878, 26 pages.

Guttman, M. et al. (2011). "lincRNAs Act In The Circuitry Controlling Pluripotency and Differentiation," Nature 477(7364):295-300, 32 pages.

(56) References Cited

OTHER PUBLICATIONS

Gürlebeck, D. et al. (2006). "Type III Effector Proteins From The Plant Pathogen Xanthomonas and Their Role In The Interaction With The Host Plant," J Plant Physiol. 163(3):233-255.

Harlow, E. et al. (1988). Antibodies A Laboratory Manual, Table of Contents only, 9 pages.

Hart, T. et al. (2014). "Measuring Error Rates In Genomic Perturbation Screens: Gold Standards For Human Functional Genomics," Molecular Systems Biology 10:733, 16 pages.

Hart, T. et al. (Dec. 3, 2015). "High-Resolution CRISPR Screens Reveal Fitness Genes and Genotype-Specific Cancer Liabilities," Cell 163:1-12.

He, Y.-F. et al. (Sep. 2, 2011). "Tet-Mediated Formation of 5-Carboxylcytosine and Its Excision By TDG In Mammalian DNA," Science 333(6047):1303-1307, 10 pages.

Heckl, D. et al. (Sep. 30, 2014). "Generation of Mouse Models of Myeloid Malignancy With Combinatorial Genetic Lesions Using CRISPR-Cas9 Genome Editing," Nat. Biotechnol. 32(9):941-946, 14 pages.

Heidari, N. et al. (2014). "Genome-Wide Map of Regulatory Interactions In The Human Genome," Genome Res. 24:1905-1917.

Hess, G.T. et al. (2016, e-pub. Oct. 31, 2016). "Directed Evolution Using dCas9-Targeted Somatic Hypermutation In Mammalian Cells," Nat. Methods, 10 pages.

Hsu, P.D. et al. (Sep. 2013). "DNA Targeting Specificity of RNA-Guided Cas9 Nucleases," Nat Biotechnol. 31:827-832, 17 pages.

Hsu, PD. et al. (Jun. 5, 2014). "Development and Applications of CRISPR-Cas9 For Genome Engineering," Cell 157(6):1262-1278, 34 pages.

Hu, J. et al. (2014). "Direct Activation of Human and Mouse Oct4 Genes Using Engineered TALE and Cas9 Transcription Factors," Nucleic Acids Res 42(7):4375-4390, 19 pages.

Huang, Y. et al. (Oct. 2014). "Connections Between TET Proteins and Aberrant DNA Modification In Cancer," Trends Genet 30(10):464-474, 25 pages.

International Preliminary Report on Patentability Opinion, dated Jun. 16, 2021, for PCT Application No. PCT/CN2019/127080, filed Dec. 20, 2019, 4 pages.

International Preliminary Report on Patentability Opinion, dated Sep. 28, 2021, for PCT Application No. PCT/CN2020/081283, filed Mar. 26, 2022, 5 pages.

International Search Report and Written Opinion, dated Jul. 1, 2020, for PCT Application No. PCT/CN2020/081283, filed Mar. 26, 2022, 10 pages.

International Search Report and Written Opinion, dated Mar. 25, 2020, for PCT Application No. PCT/CN2019/127080, filed Dec. 20, 2019, 8 pages.

International Search Report, dated Jan. 4, 2019, for PCT Application No. PCT/CN2018/081635, 6 pages.

International Search Report, dated May 7, 2018, for PCT Application No. PCT/CN2017/095988, English Translation, 3 pages.

Ito, S. et al. (Aug. 26, 2010). "Role of Tet Proteins In 5mC to 5hmC Conversion, ES-Cell Self-Renewal and Inner Cell Mass Specification," Nature 466(7310):1129-1133.

Jackson, S.P. (2002). "Sensing and Repairing DNA Double-Strand Breaks," Carcinogenesis 23(5):687-696.

Jiao, X. et al. (2012). "DAVID-WS: A Stateful Web Service To Facilitate Gene/Protein List Analysis," Bioinformatics 28:1805-1806.

Jinek, M. et al. (Aug. 17, 2012, e-pub. Jun. 28, 2012). "A Programmable Dual-RNA-Guided DNA Endonuclease In Adaptive Bacterial Immunity," Science 337(6096):816-821, 14 pages.

Joung, J. et al. (Aug. 17, 2017). "Genome-Scale Activation Screen Identifies a LncRNA Locus Regulating A Gene Neighborhood," Nature 548(7667):343-346, 28 pages.

Kaufman, R.J. et al. (1987). "Translational Efficiency of Polycistronic mRNAs and Their Utilization To Express Heterologous Genes In Mammalian Cells," The EMBO Journal 6(1):187-195.

Kay, S. et al. (2009). "How Xanthomonas Type III Effectors Manipulate The Host Plant," Curr Opin Microbiol 12(1):37-43.

Kay, S. et al. (Oct. 26, 2007). "A Bacterial Effector Acts As a Plant Transcription Factor and Induces a Cell Size Regulator," Science 318(5850):648-651.

Kim, H. et al. (Nov. 2011). "Surrogate Reporters for Enrichment of Cells With Nuclease-Induced Mutations," Nat. Methods 8(11):941-943.

Kim, H.J. et al. (2009). "Targeted Genome Editing In Human Cells With Zinc Finger Nucleases Constructed Via Modular Assembly," Genome Res. 19:1279-1288.

Kim, Y. et al. (Mar. 2013, e-pub. Feb. 17, 2013). "A Library of TAL effector Nucleases Spanning The Human Genome," Nat Biotechnol 31(3):251-258.

Kim, Y.-G. et al. (Feb. 1996). "Hybrid Restriction Enzymes: Zinc Finger Fusions To Fok I Cleavage Domain," Proc. Natl. Acad. Sci. USA 93:1156-1160.

Kohli, R.M. et al. (Oct. 24, 2013). TET Enzymes, TDG and The Dynamics of DNA Demethylation, Nature 502(7472):472-479, 21 pages.

Koike-Yusa, H. et al. (2014, e-pub. Dec. 23, 2013). "Genome-wide Recessive Genetic Screening In Mammalian Cells With a Lentiviral CRISPR-Guide RNA Library." Nat Biotechnol 32:267-273.

Kolde, R. et al. (2012, e-pub. Jan. 12, 2012). "Robust Rank Aggregation For Gene List Integration and Meta-Analysis," Bioinformatics 28(4):573-580.

Konermann, S. et al. (Jan. 29, 2015). "Genome-Scale Transcriptional Activation By an Engineered CRISPR-Cas9 Complex," Nature 517:583-588.

Koziol, M.J. et al. (Jan. 2016). "Identification of Methylated Deoxyadenosines In Vertebrates Reveals Diversity In DNA Modifications," Nature Structural & Molecular Biology 23(1):24-30, 23 pages.

Kretz, M. et al. (Jan. 10, 2013). "Control of Somatic Tissue Differentiation By The Long Non-Coding RNA TINCR," Nature 493:231-235, 16 pages.

Kriaucionis, S. et al. (Apr. 16, 2009). The Nuclear DNA Base 5-Hydroxymethylcytosine Is Present In Purkinje Neurons and The Brain, Science 324(5929):929-930.

Kubik, G. et al. (Jan. 5, 2015). "Programmable Sensors of 5-Hydroxymethylcytosine," J Am Chem Soc 137(1):2-5.

Kubik, G. et al. (2014). "Programmable and Highly Resolved In Vitro Detection of 5-Methylcytosine By TALEs," Angew Chem Int Ed Engl 53(23):6002-6006.

Kubik, G. et al. (2015). "Achieving Single-Nucleotide Resolution of 5-Methylcytosine Detection With TALEs," Chembiochem 16(2):228-231.

Lackner, D.H. et al. (Dec. 17, 2015). "A Generic Strategy For CRISPR-Cas9-Mediated Gene Tagging," Nature Communications 6:10237, 7 pages.

Leng, N. et al. (2013, e-pub. Feb. 21, 2013). "EBSeq: An Empirical Bayes Hierarchical Model For Inference in RNA-Seq Experiments," Bioinformatics 29(8):1035-1043.

Li, B. et al. (2011). "RSEM: Accurate Transcript Quantification From RNA-Seq Data With Or Without a Reference Genome," BMC Bioinformatics 12:323, 16 pages.

Li, H.L. et al. (2016, e-pub. Oct. 23, 2015). "Efficient Genomic Correction Methods In Human iPS Cells Using CRISPR-Cas9 System," Methods 101:27-35.

Li, K. et al. (Aug. 28, 2014). "Optimization of Genome Engineering Approaches with the CRISPR/Cas9 System," PLoS One 9(8):e105779, 10 pages.

Li, W. et al. (2014). "MAGeCK Enables Robust Identification Of Essential Genes From Genome-Scale CRISPR/Cas9 Knockout Screens," Genome Biol 15:554, 12 pages.

Liao, S. et al. (2015, e-pub. Jun. 29, 2015). "Enriching CRISPR-Cas9 Targeted Cells By Co-Targeting The HPRT Gene," Nucleic Acids Res. 43(20):e134, 8 pages.

Lim, K.H. et al. (Jul. 5, 2011). "Using Positional Distribution To Identify Splicing Elements and Predict Pre-mRNA Processing Defects In Human Genes," Proc. Natl. Acad. Sci. USA. 108(27):11093-11098.

Lin, N. et al. (Mar. 2014). "An Evolutionarily Conserved Long Noncoding RNA TUNA Controls Pluripotency and Neural Lineage Commitment," Mol. Cell. 53:1005-1019.

(56) References Cited

OTHER PUBLICATIONS

Liu, S.J. et al. (Jan. 6, 2017). "CRISPRi-Based Genome-Scale Identification of Functional Long Noncoding RNA Loci In Human Cells," Science 355(6320):1-19.
Liu, Y. et al. (Dec. 2018, e-pub. Nov. 5, 2018). "Genome-Wide Screening For Functional Long Noncoding RNAs In Human Cells By Cas9 Targeting Of Splice Sites," Nature Biotechnology 36(12):1203-2010.
Long, C. et al. (Jan. 31, 2018). "Correction of Diverse Muscular Dystrophy Mutations in Human Engineered Heart Muscle By Single-Site Genome Editing," Science Advances 4:eaap9004, 11 pages.
Lyras, D. et al. (2009). "Toxin B Is Essential For Virulence of Clostridium difficile," Nature 458:1176-1179.
Lü, S. et al. (2013). "The Resistance Mechanisms of Proteasome Inhibitor Bortezomi," Biomarker Research 1:13, 9 pages.
Ma, H. et al. (Mar. 10, 2015). "Multicolor CRISPR Labeling of Chromosomal Loci In Human Cells," Proc. Natl. Acad. Sci. USA 112:3002-3007.
Maiti, A. et al. (Oct. 14, 2011). "Thymine DNA Glycosylase Can Rapidly Excise 5-Formylcytosine and 5-Carboxylcytosine: Potential Implications For Active Demethylation of CpG Sites," J Biol Chem 286(41):35334-35338.
Mak, A.N.-S. et al. (Feb. 10, 2012) "The Crystal Structure of TAL Effector PthXo1 Bound To Its DNA Target," Science 335(6069):716-719, 11 pages.
Mali, P. et al. (Feb. 15, 2013, e-pub. Jan. 3, 2013). "RNA Guided Human Genome Engineering via Cas9," Science 339(6121):823-826, 8 pages.
Matlin, AJ. et al. (May 2005). "Understanding Alternative Splicing: Towards a Cellular Code," Nat. Rev. Mol. Cell Biol. 6:386-398.
Maurer, S. et al. (Nov. 4, 2016). "Interrogating Key Positions of Size-Reduced TALE Repeats Reveals a Programmable Sensor of 5-Carboxylcytosine," ACS Chem Biol 11(12):3294-3299.
Meyers, R.M. et al. (2017, e-pub. Oct. 30, 2017). "Computational Correction Of Copy Number Effect Improves Specificity Of CRISPR-Cas9 Essentiality Screens In Cancer Cells," Nat Genet 49:1779-1784.
Michlits, G. et al. (2017, e-pub. Oct. 16, 2017). "CRISPR-UMI: Single-Cell Lineage Tracing Of Pooled CRISPR-Cas9 Screens," Nat Methods 14:1191-1197.
Miller, J.C. et al. (Feb. 2011, e-pub. Dec. 22, 2010). "A Tale Nuclease Architecture For Efficient Genome Editing," Nature Biotechnology 29(2):143-148.
Miller, J.C. et al. (May 2015, e-pub. Mar. 23, 2015). "Improved Specificity of TALE-Based Genome Editing Using An Expanded RVD Repertoire," Nat Methods 12(5):465-471.
Mitamura, T. et al. (Oct. 24, 1997). "Structure-Function Analysis of The Diphtheria Toxin Receptor Toxin Binding Site By Site-Directed Mutagenesis," J. Biol. Chem. 272:27084-27090.
Miyaoka, Y. et al. (Mar. 2014). "Isolation of Single-Base Genome-Edited Human iPS Cells Without Antibiotic Selection," Nat Methods 11:291-293, 15 pages.
Morbitzer, R. (Dec. 14, 2010). "Regulation of Selected Genome Loci Using De Novo-Engineered Transcription Activator-Like Effector (TALE)-Type Transcription Factors," Proc Natl Acad Sci USA 107(50):21617-21622.
Moscou, M.J. et al. (Dec. 11, 2009, e-pub. Oct. 29, 2009). "A Simple Cipher Governs DNA Recognition By TAL Effectors," Science 326:1501, 1 page.
Muller, R.Y. et al. (2015). "An Efficient Method for Electroporation of Small Interfering RNAs into ENCODE Project Tier 1 GM12878 and K562 Cell Lines," J. Biomol. Tech 26:142-149.
Murugan, R.N. et al. (Sep. 30, 2011). "Plk1-Targeted Small Molecule Inhibitors: Molecular Basis For Their Potency and Specificity," Mol. Cells 32:209-220.
Mussolino, C. et al. (2011, e-pub. Aug. 3, 2011). "A Novel TALE Nuclease Scaffold Enables High Genome Editing Activity In Combination With Low Toxicity," Nucleic Acids Res 39(21):9283-9293.
Nakade, S. et al. (Nov. 20, 2014). "Microhomology-Mediated End-Joining-Dependent Integration of Donor DNA In Cells And Animals Using TALENs and CRISPR/Cas9," Nature Communications 5:5560, 8 pages.
Ng, B, et al. (Dec. 2004). "Increased Noncanonical Splicing of Autoantigen Transcripts Provides The Structural Basis For Expression of Untolerized Epitopes," Journal of Allergy and Clinical Immunology 114(6):1463-1470, 17 pages.
Nishimasu, H. et al. (Feb. 27, 2014). "Crystal Structure of cas9 in Complex With Guide RNA and Target DNA," Cell 156:935-949.
O'Brien, A. et al. (2014). "GT-Scan: Identifying Unique Genomic Targets," Bioinformatics 30(18):2673-2675.
Orlando, S.J. et al. (Aug. 2010, e-pub, Jun. 8, 2010). "Zinc-finger Nuclease-Driven Targeted Integration Into Mammalian Genomes Using Donors With Limited Chromosomal Homology," Nucleic Acids Research 38(15):e152, 15 pages.
Pastor, W.A. et al. (Jun. 2013). "TETonic Shift: Biological Roles of TET Proteins In DNA Demethylation and Transcription," Nat Rev Mol. Cell Biol. 14(6):341-356, 34 pages.
Peng, J. et al. (2015). "High-Throughput Screens In Mammalian Cells Using The CRISPR-Cas9 System," FEBS J. 282:2089-2096.
Perez, E.E. et al. (2008, e-pub. Jun. 29, 2008). "Establishment of HIV-1 Resistance In CD4+ T Cells By Genome Editing Using Zinc-Finger Nucleases," Nat. Biotechnol. 26:808-816.
Pfaffeneder, T. et al. (2011). "The Discovery of 5-Formylcytosine In Embryonic Stem Cell DNA," Angew Chem Int Ed Engl 50(31):7008-7012.
Phillips, E.R. et al. (2007). "DNA Double-Strand Break Repair and Development," Oncogene 26:7799-7808.
Potter, C.J. et al. (Apr. 13, 2010). "Splinkerette PCR For Mapping Transposable Elements In *Drosophila*," PLoS One 5(4):e10168, 9 pages.
Qian, L. et al. (May 2014, e-pub. Mar. 25, 2014). "Bidirectional Effect Of Wnt Signaling Antagonist DKK1 On The Modulation Of Anthrax Toxin Uptake," Science China Life Sciences 57(5):469-481.
Quinn, J.J. et al. (Jan. 2016). "Unique Features of Long Non-Coding RNA Biogenesis and Function," Nat. Rev. Genet. 17:47-62.
Ramakrishna, S. et al. (Feb. 26, 2014). "Surrogate Reporter-Based Enrichment of Cells Containing RNA-Guided Cas9 Nuclease-Induced Mutations," Nature Communications 5:3378, 10 pages.
Ratel, D. et al. (2006). "N6-Methyladenine: The Other Methylated Base of DNA," BioEssays 28:309-315.
Rathi, P. et al. (Jul. 18, 2016). "Isolation of Human Genomic DNA Sequences With Expanded Nucleobase Selectivity," J Am Chem Soc 138(31):9910-9918.
Ren, Q. et al. (Mar. 9, 2015). "A Dual-Reporter System for Real-Time Monitoring and High-throughput CRISPR/Cas9 Library Screening of the Hepatitis C Virus," Scientific Reports 5:8865.
Richardson, C.D. et al. (2016, e-pub. Jan. 20, 2016). "Enhancing Homology-Directed Genome Editing By Catalytically Active and Inactive CRISPR-Cas9 Using Asymmetric Donor DNA," Nat. Biotechnol., 7 pages.
Rinn, J.L. et al. (2012). "Genome Regulation By Long Noncoding RNAs," Annu. Rev. Biochem 81:145-166, 25 pages.
Robinson, M.D. et al. (2008, e-pub. Aug. 29, 2007). "Small-Sample Estimation Of Negative Binomial Dispersion, With Applications To SAGE Data," Biostatistics 9:321-332.
Sakuma, T. et al. (2016, e-pub. Dec. 17, 2015). "MMEJ-Assisted Gene Knock-In Using TALENs and CRISPR/Cas9 With The PITCh Systems," Nat. Protoc. 11(1):118-133.
Sambrook, J. et al. (1989). Molecular Cloning: A Laboratory Manual, 3rd Ed. 29 pages.
Sambrook, J. et al. (2001). Molecular Cloning: A Laboratory Manual Cold Spring Harbor Laboratory Press, Cold Spring Harbor,N. Y., 3rd ed., 1 page, Table of Contents.
Sanjana, N. (Mar. 19, 2014). "Human and Mouse Non-Targeting Guides From GeCKOV2 Library," SanjanaLab, 5 pages.
Savić, N. et al. (2016). "Advances In Therapeutic CRISPR/Cas9 Genome Editing," Translational Research: The Journal Of Laboratory and Clinical Medicine 168:15-21.

(56) References Cited

OTHER PUBLICATIONS

Schmid-Burgk. J.L. et al. (Jul. 28, 2016). "CRISPaint Allows Modular Base-Specific Gene Tagging Using a Ligase-4-Dependent Mechanism," Nature Communications 7(12338):1-12.
Schmierer, B. et al. (2017, e-pub. Oct. 9, 2017). "CRISPR/Cas9 Screening Using Unique Molecular Identifiers," Molecular Systems Biology 13:945, 8 pages.
Seed, B. (1987). "An LFA-3 cDNA Encodes a Phospholipid-Linked Membrane Protein Homologous To Its Receptor CD2," Nature 329:840-842.
Shalem, O. et al. (Jan. 3, 2014). "Genome-Scale CRISPR-Cas9 Knockout Screening In Human Cells," Science 343:84-87.
Shechner, D.M. et al. (2015, e-pub. Jun. 1, 2015). "Multiplexable, Locus-Specific Targeting Of Long RNAs With CRISPR-Display," Nat Methods 12:664-670.
Steegmaier, M. et al. (Feb. 20, 2007). "BI 2536, A Potent and Selective Inhibitor of Polo-Like Kinase 1, Inhibits Tumor Growth In Vivo," Curr. Biol. 17:316-322.
Suzuki, E. et al. (Dec. 22, 2011). "Molecular Mechanisms of Bortezomib Resistant Adenocarcinoma Cells," PLoS One 6(12):e27996, 11 pages.
Taggart, A.J. et al. (2012). "Large-Scale Mapping of Branchpoints In Human Pre-mRNA Transcripts In Vivo," Nat. Struct. Mol. Biol. 19(7):719-721, 9 pages.
Tahiliani, M. et al. (May 15, 2009). "Conversion of 5-Methylcytosine To 5-Hydroxymethylcytosine In Mammalian DNA By MLL Partner TET1," Science 324(5929):930-935, 11 pages.
Tan, Y.Y. et al. (Aug. 15, 1989). "In Vitro Evaluation Of 6-Thioguanine and Alpha-Interferon as a Therapeutic Combination In HL-60 and Natural Killer Cells," Cancer Res. 49:4431-4434.
Tao, L. et al. (2016). "Frizzled Proteins Are Colonic Epithelial Receptors For C. difficile Toxin B," Nature 538:350-355.
Uren, A.G. et al. (2009, e-pub. Apr. 30, 2009). "A High-Throughput Splinkerette-PCR Method For The Isolation and Sequencing of Retroviral Insertion Sites," Nat. Protoc. 4(5):789-798.
Valton, J. et al. (Nov. 9, 2012). "Overcoming Transcription Activator-Like Effector (TALE) DNA Binding Domain Sensitivity To Cytosine Methylation," J Biol Chem 287(46):38427-38432.
Van Overbeek, M. et al. (Aug. 18, 2016). "DNA Repair Profiling Reveals Nonrandom Outcomes at Cas9-Mediated Breaks," Mol. Cell 63:1-14.
Wacker, S.A. et al. (Mar. 2012). "Using Transcriptome Sequencing To Identify Mechanisms Of Drug Action and Resistance," Nat. Chem. Biol. 8:235-237.
Wang, T. et al. (Jan. 3, 2014). "Genetic Screens In Human Cells Using The CRISPR-Cas9 System," Science 343:80-84.
Wang, T. et al. (Nov. 27, 2015). "Identification and Characterization of Essential Genes In The Human Genome," Science 350(6264):1096-1101.
Warf, M.B. et al. (2010). "Role of RNA Structure In Regulating Pre-mRNA Splicing," Trends Biochem. Sci. 35:169-178, 21 pages.
Wei, W. et al. (Mar. 24, 2006). "The LDL Receptor-Related Protein LRP6 Mediates Internalization and Lethality Of Anthrax Toxin," Cell 124:1141-1154.
Wion, D. (Mar. 2006). "N6-Methyl-Adenine: An Epigenetic Signal For DNA-Protein Interactions," Nature Reviews Microbiology 4:183-192.
Wu, H. et al. (Sep. 2015). "Charting Oxidized Methylcytosines At Base Resolution," Nat Struct Mol Biol 22(9):656-661, 14 pages.
Xu, H. et al. (2015). "Sequence Determinants of Improved CRISPR sgRNA Design," Genome Res. 25:1147-1157.
Yang, J. et al. (2016). "Assembly of Customized TAL Effectors Through Advanced ULtiMATE System." TALENs: Methods and Protocols pp. 49-60.
Yang, J. et al. (May 2014) Complete Decoding of TAL Effectors For DNA Recognition, Cell Research 24(5):628-631.
Yang, J. et al. (Sep. 27, 2013). "ULtiMATE System For Rapid Assembly of Customized TAL Effectors," PLoS One 8(9):e75649, 8 pages.
Yin, B. et al. (Jul. 2007). "PCR-Based Procedures To Isolate Insertion Sites of DNA Elements," Biotechniques 43(1):79-84.
Yu, C. et al. (Feb. 5, 2015). "Small Molecules Enhance CRISPR Genome Editing in Pluripotent Stem Cells," Cell Stem Cell 16:142-147.
Yu, M. et al. (Jun. 8, 2012). "Base-Resolution Analysis of 5-Hydroxymethylcytosine In The Mammalian Genome," Cell 149(6):1368-1380, 23 pages.
Yuan, P. et al. (2015, e-pub. Dec. 30, 2014). "Chondroitin Sulfate Proteoglycan 4 Functions As The Cellular Receptor For Clostridium difficile Toxin B," Cell Res 25:157-168.
Zhang, G. et al. (May 7, 2015). "N6-Methyladenine DNA Modification In *Drosophila*," Cell 161:1-14.
Zhang, Y. et al. (2017, e-pub. Oct. 12, 2017). "Deciphering TAL Effectors For 5-Methylcytosine and 5-Hydroxymethylcytosine Recognition," Nature Communications, 8(1):1-9.
Zhou, Y. et al. (2017, e-pub. Jan. 13, 2017). "Painting a Specific Chromosome With CRISPR/Cas9 For Live-Cell Imaging," Cell Res. 27:298-301, 4 pages.
Zhou, Y. et al. (May 22, 2014). "High-Throughput Screening Of a CRISPR/Cas9 Library For Functional Genomics In Human Cells," Nature 509:487-491.
Zhu, S. et al. (2017). "Genome-Wide CRISPR/Cas9 Screening for High-Throughput Functional Genomics in Human Cells," Methods Mol Biol 1656:175-181.
Zhu, S. et al. (Dec. 2016, e-pub. Oct. 31, 2016). "Genome-Scale Deletion Screening Of Human Long Non-Coding RNAs Using a Paired-Guide RNA CRISPR-Cas9 Library," Nature Biotechnology 34(12):1279-1286.
Tsuji, S. et al. (2016). "Sequence-Specific Recognition of Methylated DNA by an Engineered Transcription Activator-Like Effector Protein," Chem. Commun. 52:14238-14241.

\* cited by examiner

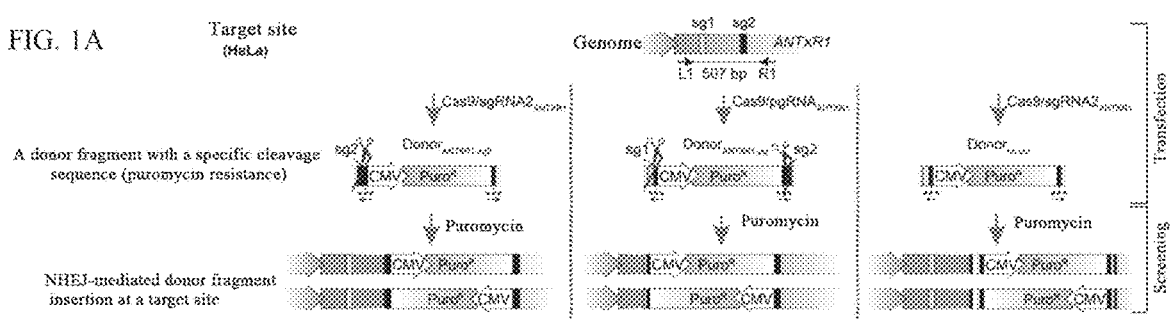
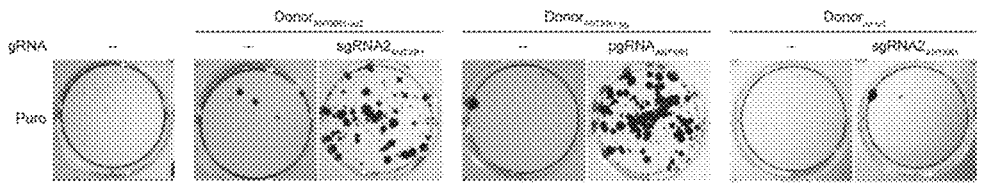
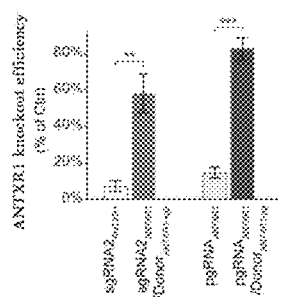

FIG. 3A
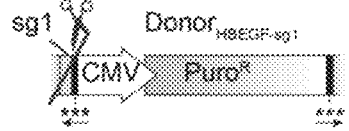
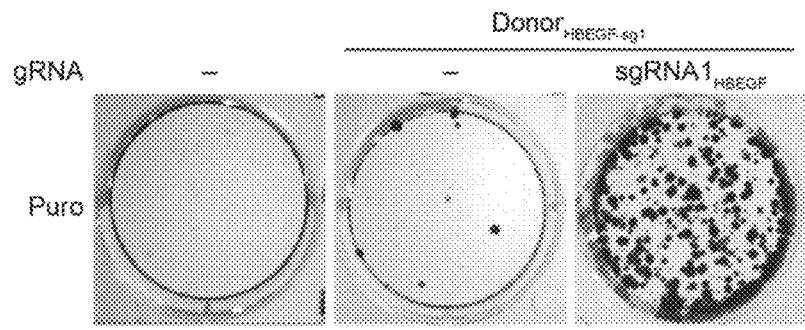
FIG. 3B
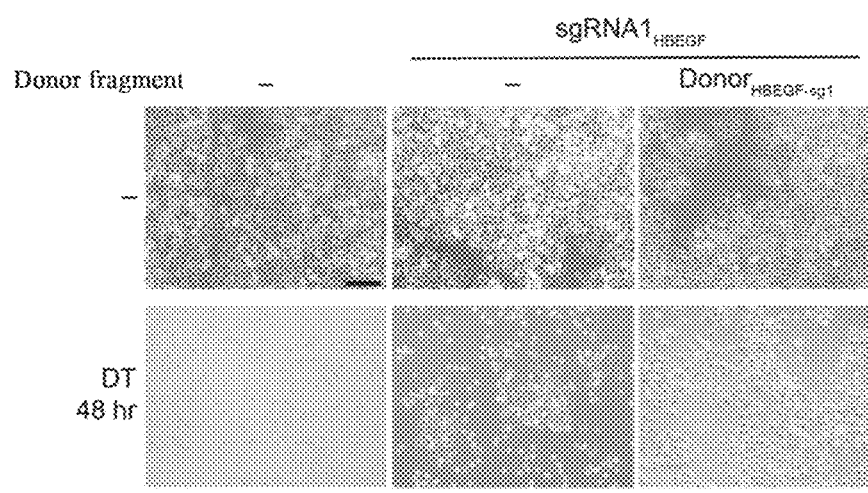
FIG. 3C
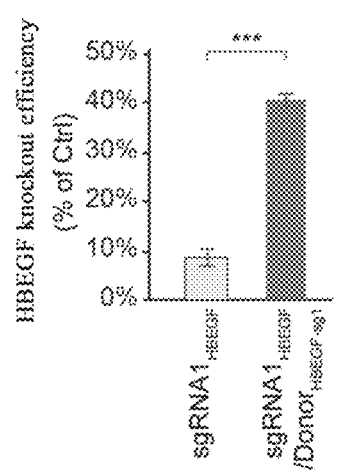
FIG. 3D

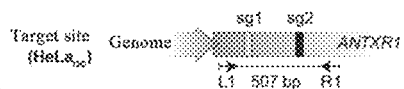
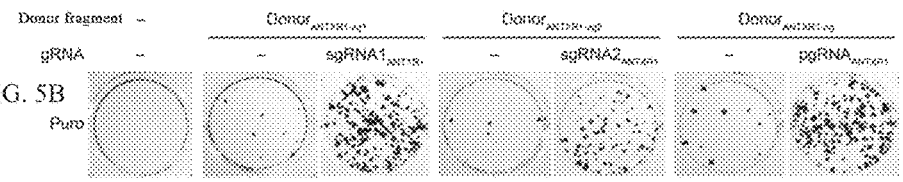
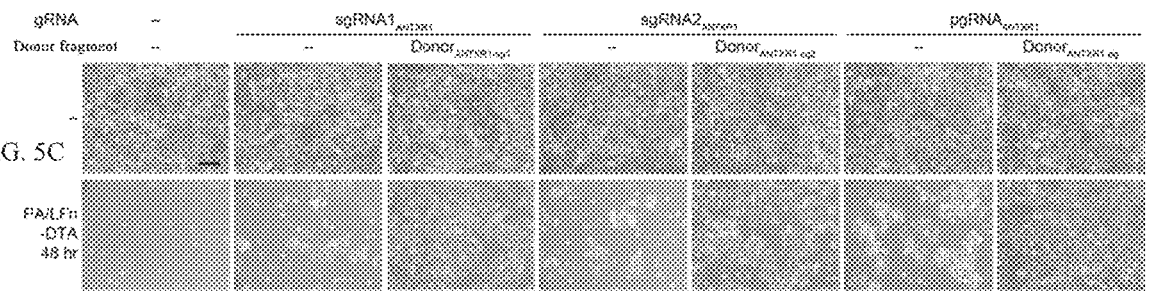
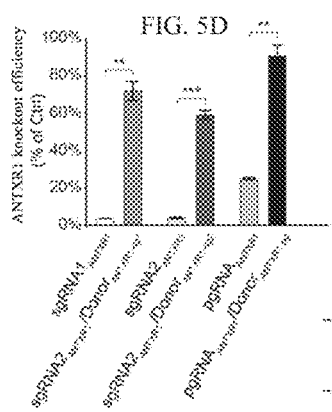
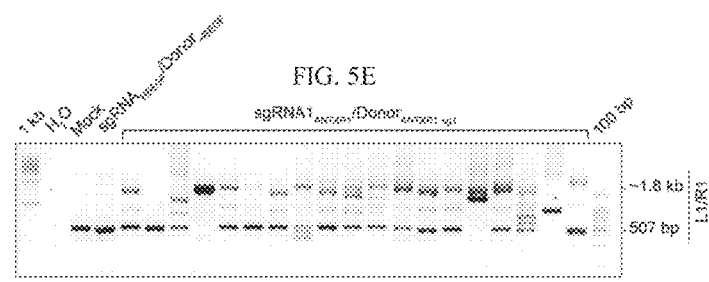

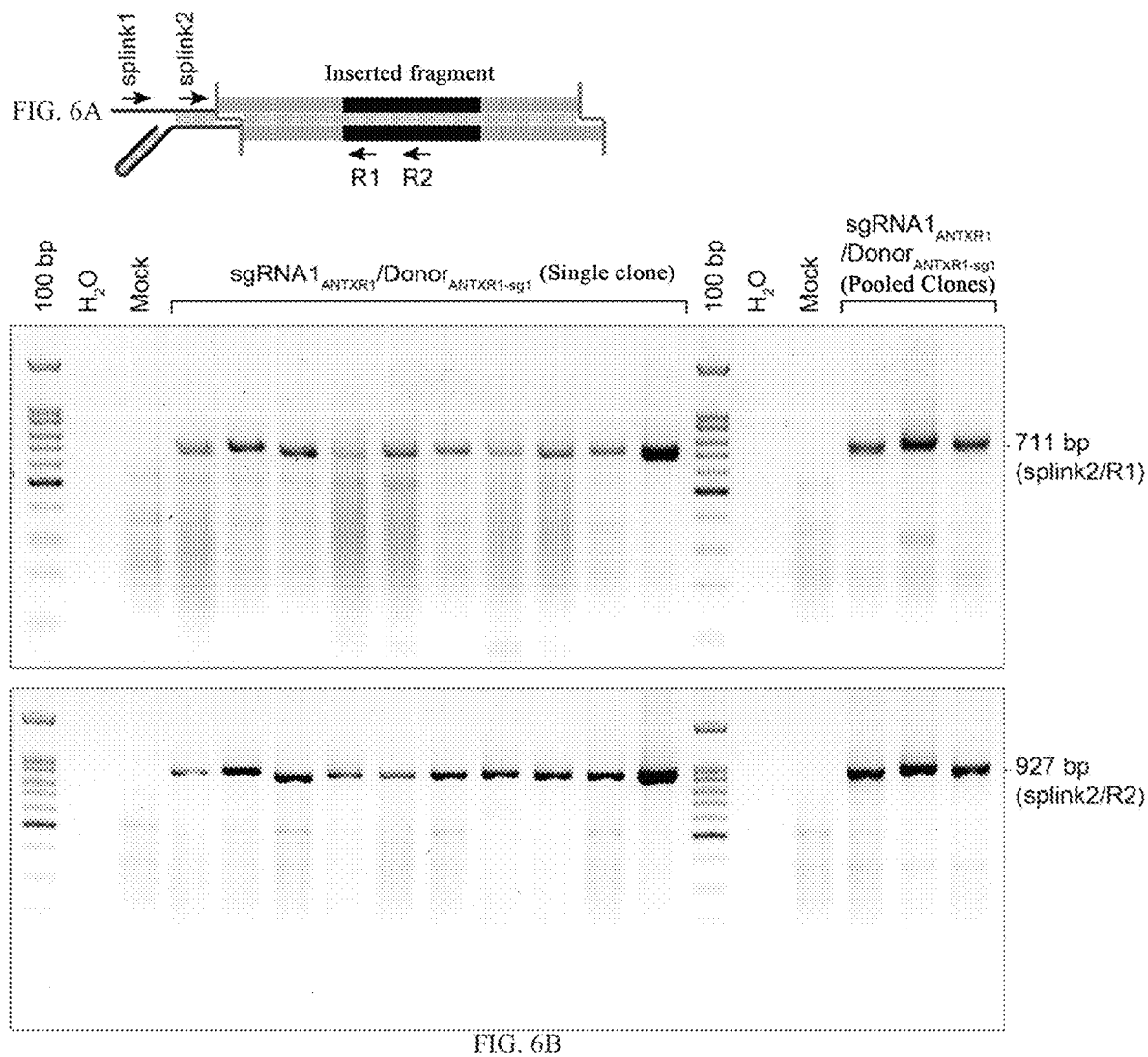

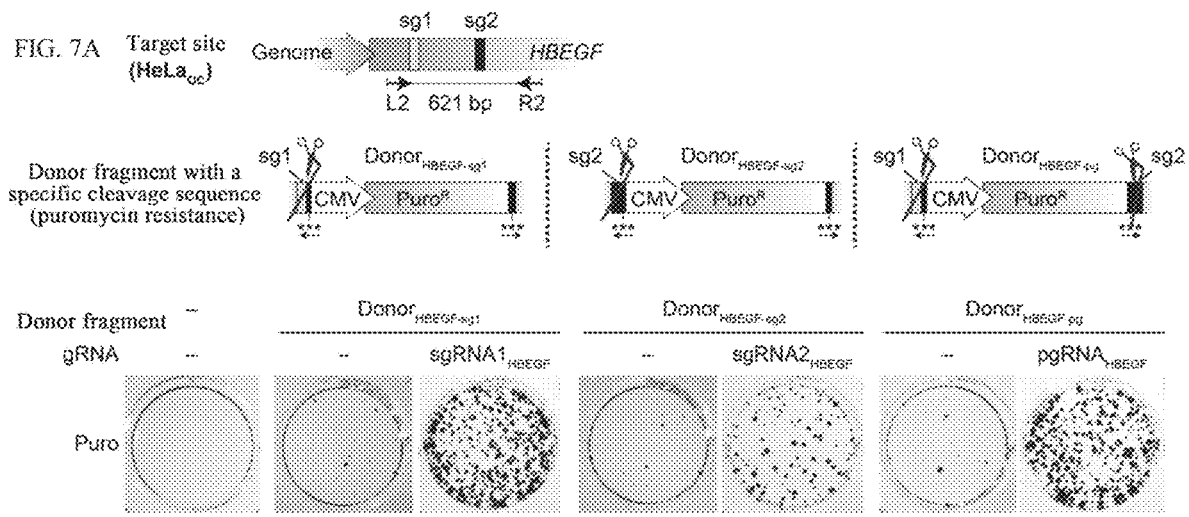
FIG. 7A
FIG. 7B
FIG. 7C
FIG. 7D

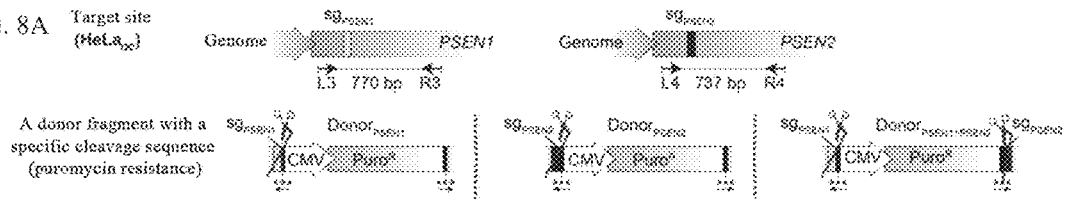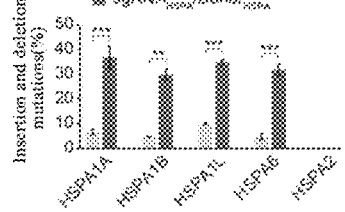

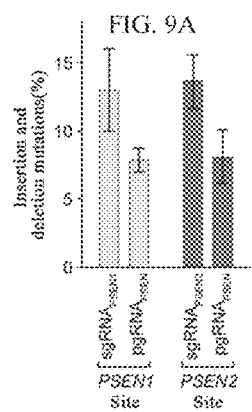
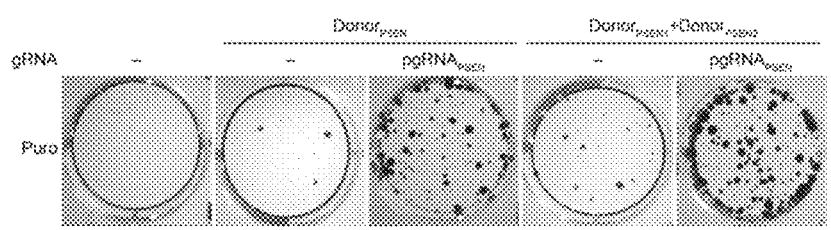
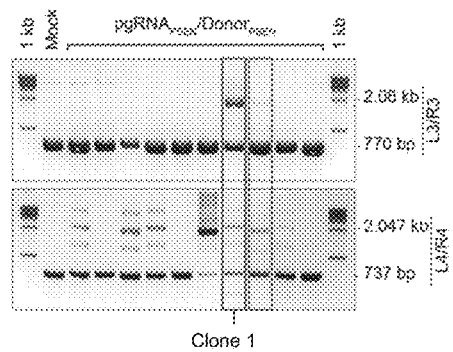
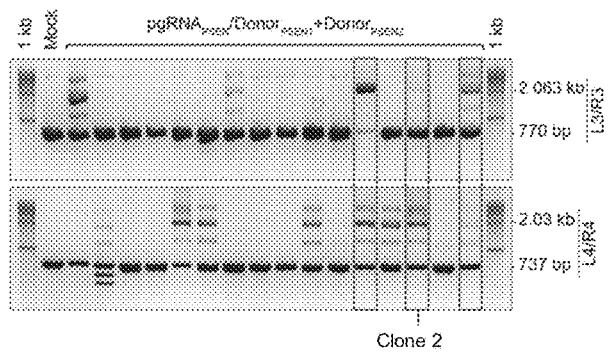
FIG. 9C

| Number of sites with donor fragments inserted | Number of clones with corresponding inserts/total number of clones(%) |
|---|---|
| 4 | 0 / 21 (0%) |
| 3 | 2 / 21 (9.5%) |
| 2 | 9 / 21 (42.9%) |
| 1 | 9 / 21 (42.9%) |
| 0 | 1 / 21 (4.8%) |

SEQUENCE LISTING

```
<160> NUMBER OF SEQ ID NOS: 119

<210> SEQ ID NO 1
<211> LENGTH: 20
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 1
gtacggggcg atcatccaca                                              20

<210> SEQ ID NO 2
<211> LENGTH: 20
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 2
aatcgactcg aacttcgtgt                                              20

<210> SEQ ID NO 3
<211> LENGTH: 22
<212> TYPE: DNA
<213> ORGANISM: Homo sapiens

<400> SEQUENCE: 3
agcggagagc cctcggcatc gg                                           22

<210> SEQ ID NO 4
<211> LENGTH: 23
<212> TYPE: DNA
<213> ORGANISM: Homo sapiens

<400> SEQUENCE: 4
tgctcatctg cgccgggcaa ggg                                          23

<210> SEQ ID NO 5
<211> LENGTH: 20
<212> TYPE: DNA
<213> ORGANISM: Artificial Sequence
<220> FEATURE:
<223> OTHER INFORMATION: ARTIFICIALLY SYNTHESIZED SEQUENCE
```

```
<400> SEQUENCE: 5
aagcggagga caggattggg                                               20

<210> SEQ ID NO 6
<211> LENGTH: 20
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 6
cctctgtggc cctggagatg                                               20

<210> SEQ ID NO 7
<211> LENGTH: 22
<212> TYPE: DNA
<213> ORGANISM: Homo sapiens

<400> SEQUENCE: 7
gactggcgag agcctggagc gg                                            22

<210> SEQ ID NO 8
<211> LENGTH: 22
<212> TYPE: DNA
<213> ORGANISM: Homo sapiens

<400> SEQUENCE: 8
cggaccagct gctaccccta gg                                            22

<210> SEQ ID NO 9
<211> LENGTH: 20
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 9
gccgcttcga aagtgactgg                                               20

<210> SEQ ID NO 10
<211> LENGTH: 20
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 10
gatcccccag tgcccatcag                                               20

<210> SEQ ID NO 11
<211> LENGTH: 23
<212> TYPE: DNA
<213> ORGANISM: Homo sapiens

<400> SEQUENCE: 11
ccagaatgca cagatgtctg agg                                           23

<210> SEQ ID NO 12
<211> LENGTH: 22
<212> TYPE: DNA
<213> ORGANISM: Homo sapiens

<400> SEQUENCE: 12
ttcatggcct ctgacagcga gg                                            22
```

```
<210> SEQ ID NO 13
<211> LENGTH: 20
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 13
tggtgtctca ggcggttcta                                                   20

<210> SEQ ID NO 14
<211> LENGTH: 20
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 14
tgaactatga ggcgctgcac                                                   20

<210> SEQ ID NO 15
<211> LENGTH: 20
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 15
tgactttcgt ggctatgcgt                                                   20

<210> SEQ ID NO 16
<211> LENGTH: 20
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 16
ctagcaccca ggcatccaaa                                                   20

<210> SEQ ID NO 17
<211> LENGTH: 20
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 17
gagagtgact cccgttgtcc                                                   20

<210> SEQ ID NO 18
<211> LENGTH: 24
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 18
acattgcaaa cacaggaaat tgag                                              24

<210> SEQ ID NO 19
<211> LENGTH: 20
<212> TYPE: DNA
<213> ORGANISM: Artificial Sequence
<220> FEATURE:
<223> OTHER INFORMATION: ARTIFICIALLY SYNTHESIZED SEQUENCE
```

<400> SEQUENCE: 19
gtgttgagtt tccggcgttc                                              20

<210> SEQ ID NO 20
<211> LENGTH: 20
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 20
tcgcttgttc tggctgatgt                                              20

<210> SEQ ID NO 21
<211> LENGTH: 24
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 21
gcactctccc aaaacagtat ctta                                         24

<210> SEQ ID NO 22
<211> LENGTH: 20
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 22
gtgcctccac ccagatcaaa                                              20

<210> SEQ ID NO 23
<211> LENGTH: 20
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 23
gggtgaggcg caaaaggata                                              20

<210> SEQ ID NO 24
<211> LENGTH: 20
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 24
acaccagcgt caatggagag                                              20

<210> SEQ ID NO 25
<211> LENGTH: 23
<212> TYPE: DNA
<213> ORGANISM: Artificial Sequence
<220> FEATURE:
<223> OTHER INFORMATION: PAM sequence

<400> SEQUENCE: 25
gtacggggcg atcatccaca cgg                                          23

<210> SEQ ID NO 26
<211> LENGTH: 23
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 26
gcaaaagtgg cataaaaccg cgg                                              23

<210> SEQ ID NO 27
<211> LENGTH: 23
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 27
tatcgcttcc gattagtccg cgg                                              23

<210> SEQ ID NO 28
<211> LENGTH: 23
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 28
ctatctcgag tggtaatgcg cgg                                              23

<210> SEQ ID NO 29
<211> LENGTH: 23
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 29
gtagctgctg taaatcgcat cgg                                              23

<210> SEQ ID NO 30
<211> LENGTH: 23
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 30
tataccagac cacagcgccg cgg                                              23

<210> SEQ ID NO 31
<211> LENGTH: 23
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 31
gcacgaggtg aacagccgct cgg                                              23

<210> SEQ ID NO 32
<211> LENGTH: 23
<212> TYPE: DNA
<213> ORGANISM: Artificial Sequence
<220> FEATURE:
<223> OTHER INFORMATION: ARTIFICIALLY SYNTHESIZED SEQUENCE

```
<400> SEQUENCE: 32
atgatatctg acatgcagcg cgg                                              23

<210> SEQ ID NO 33
<211> LENGTH: 23
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 33
aatcgactcg aacttcgtgt cgg                                              23

<210> SEQ ID NO 34
<211> LENGTH: 23
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 34
cgaatcggaa ctttgtaccg cgg                                              23

<210> SEQ ID NO 35
<211> LENGTH: 23
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 35
accgagcgga gagccctcgg cat                                              23

<210> SEQ ID NO 36
<211> LENGTH: 23
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 36
aaacatgccg agggctctcc gct                                              23

<210> SEQ ID NO 37
<211> LENGTH: 24
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 37
accgtgctca tctgcgccgg gcaa                                             24

<210> SEQ ID NO 38
<211> LENGTH: 24
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 38
aaacttgccc ggcgcagatg agca                                             24
```

```
<210> SEQ ID NO 39
<211> LENGTH: 58
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 39
tatacgtctc aaccgagcgg agagccctcg gcatgtttaa gagctatgct ggaaacag        58

<210> SEQ ID NO 40
<211> LENGTH: 56
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 40
tatacgtctc aaaacttgcc cggcgcagat gagcacggtg tttcgtcctt tccaca          56

<210> SEQ ID NO 41
<211> LENGTH: 23
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 41
accggactgg cgagagcctg gag                                              23

<210> SEQ ID NO 42
<211> LENGTH: 23
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 42
aaacctccag gctctcgcca gtc                                              23

<210> SEQ ID NO 43
<211> LENGTH: 23
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 43
accgcggacc agctgctacc cct                                              23

<210> SEQ ID NO 44
<211> LENGTH: 23
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 44
aaacaggggt agcagctggt ccg                                              23

<210> SEQ ID NO 45
<211> LENGTH: 58
<212> TYPE: DNA
<213> ORGANISM: Artificial Sequence
<220> FEATURE:
<223> OTHER INFORMATION: ARTIFICIALLY SYNTHESIZED SEQUENCE
```

<400> SEQUENCE: 45
tatacgtctc aaccggactg gcgagagcct ggaggtttaa gagctatgct ggaaacag    58

<210> SEQ ID NO 46
<211> LENGTH: 55
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 46
tatacgtctc aaaacagggg tagcagctgg tccgcggtgt ttcgtccttt ccaca    55

<210> SEQ ID NO 47
<211> LENGTH: 24
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 47
accgccagaa tgcacagatg tctg    24

<210> SEQ ID NO 48
<211> LENGTH: 24
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 48
aaaccagaca tctgtgcatt ctgg    24

<210> SEQ ID NO 49
<211> LENGTH: 23
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 49
accgttcatg gcctctgaca gcg    23

<210> SEQ ID NO 50
<211> LENGTH: 23
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 50
aaaccgctgt cagaggccat gaa    23

<210> SEQ ID NO 51
<211> LENGTH: 58
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 51
tatacgtctc aaccgccaga atgcacagat gtctggttta agagctatgc tggaaaca    58

```
<210> SEQ ID NO 52
<211> LENGTH: 55
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 52
tatacgtctc aaaaccgctg tcagaggcca tgaacggtgt ttcgtccttt ccaca         55

<210> SEQ ID NO 53
<211> LENGTH: 22
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 53
accgcaggag taggtggtgc cc                                            22

<210> SEQ ID NO 54
<211> LENGTH: 22
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 54
aaacgggcac cacctactcc tg                                            22

<210> SEQ ID NO 55
<211> LENGTH: 59
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 55
agagccctcg gcatcggctt ccagtggctc tctttggtta gtcacctact agttagtca    59

<210> SEQ ID NO 56
<211> LENGTH: 42
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 56
ggcttaggat tgttacgccc tcacttatct actaatcaat ta                      42

<210> SEQ ID NO 57
<211> LENGTH: 57
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 57
tccactgcga cgtcgcgagt agcggagagc cctcggcatc ggcttccagt ggctctc      57

<210> SEQ ID NO 58
<211> LENGTH: 59
<212> TYPE: DNA
<213> ORGANISM: Artificial Sequence
<220> FEATURE:
<223> OTHER INFORMATION: ARTIFICIALLY SYNTHESIZED SEQUENCE
```

<400> SEQUENCE: 58
tctgcgccgg gcaaggggga cgcagggagg atggggg tta gtcacctact agttagtca       59

<210> SEQ ID NO 59
<211> LENGTH: 58
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 59
tccactgcga cgtcgcgagt tgctcatctg cgccgggcaa ggggacgca gggaggat          58

<210> SEQ ID NO 60
<211> LENGTH: 59
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 60
cccggcgcag atgagcacca gagtggccaa agagagctca cttatctact aatcaatta        59

<210> SEQ ID NO 61
<211> LENGTH: 52
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 61
ggcttaggat tgttacgccc cccttgcccg gcgcagatga gcaccagagt gg              52

<210> SEQ ID NO 62
<211> LENGTH: 59
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 62
gcgagagcct ggagcggctt cggagagggc tagctgctta gtcacctact agttagtca       59

<210> SEQ ID NO 63
<211> LENGTH: 56
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 63
tccactgcga cgtcgcgagt gactggcgag agcctggagc ggcttcggag agggct          56

<210> SEQ ID NO 64
<211> LENGTH: 58
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 64
agctgctacc cctaggaggc ggccgggacc ggaaagttag tcacctacta gttagtca        58

<210> SEQ ID NO 65
<211> LENGTH: 59
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 65
tccactgcga cgtcgcgagt cggaccagct gctaccccta ggaggcggcc gggaccgga    59

<210> SEQ ID NO 66
<211> LENGTH: 59
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 66
gggtagcagc tggtccgtgg atacagtggg agggtcctca cttatctact aatcaatta    59

<210> SEQ ID NO 67
<211> LENGTH: 56
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 67
ggcttaggat tgttacgccc cctaggggta gcagctggtc cgtggataca gtggga    56

<210> SEQ ID NO 68
<211> LENGTH: 53
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 68
gatgtctgag gacaaccacc tgagcaatac tttagtcacc tactagttag tca    53

<210> SEQ ID NO 69
<211> LENGTH: 54
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 69
tccactgcga cgtcgcgagt ccagaatgca cagatgtctg aggacaacca cctg    54

<210> SEQ ID NO 70
<211> LENGTH: 54
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 70
ctgacagcga ggaagaagtg tgtgatgagc ggttagtcac ctactagtta gtca    54

<210> SEQ ID NO 71
<211> LENGTH: 50
<212> TYPE: DNA
<213> ORGANISM: Artificial Sequence
<220> FEATURE:
<223> OTHER INFORMATION: ARTIFICIALLY SYNTHESIZED SEQUENCE -continued

```
<400> SEQUENCE: 71
tccactgcga cgtcgcgagt ttcatggcct ctgacagcga ggaagaagtg            50

<210> SEQ ID NO 72
<211> LENGTH: 55
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 72
ggcttaggat tgttacgccc cctcgctgtc agaggccatg aatgtgagca tagcc      55

<210> SEQ ID NO 73
<211> LENGTH: 50
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 73
gccatgaatg tgagcatagc cctgcctctc acttatctac taatcaatta            50

<210> SEQ ID NO 74
<211> LENGTH: 56
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 74
accacctact cctgcgtggg ggtgttccaa cacgttagtc acctactagt tagtca     56

<210> SEQ ID NO 75
<211> LENGTH: 54
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 75
tccactgcga cgtcgcgagt cctgggcacc acctactcct gcgtgggggt gttc       54

<210> SEQ ID NO 76
<211> LENGTH: 61
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 76
cgaagagtaa ccgttgctag gagagaccgt ggctgaatga gactggtgtc gacactagtg   60
g                                                                  61

<210> SEQ ID NO 77
<211> LENGTH: 48
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 77
cgcgccacta gtgtcgacac cagtctctaa ttttttttttt caaaaaaa              48
```

```
<210> SEQ ID NO 78
<211> LENGTH: 28
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 78
cgaagagtaa ccgttgctag gagagacc                                              28

<210> SEQ ID NO 79
<211> LENGTH: 25
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 79
gtggctgaat gagactggtg tcgac                                                 25

<210> SEQ ID NO 80
<211> LENGTH: 24
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 80
gcaacctccc cttctacgag cggc                                                  24

<210> SEQ ID NO 81
<211> LENGTH: 24
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 81
gcatggccgt gttgagcggt tccc                                                  24

<210> SEQ ID NO 82
<211> LENGTH: 51
<212> TYPE: DNA
<213> ORGANISM: Homo sapiens

<400> SEQUENCE: 82
taatctggga gcctgcccta cttccagaat gcacagatgt ctgaggacaa c                    51

<210> SEQ ID NO 83
<211> LENGTH: 50
<212> TYPE: DNA
<213> ORGANISM: Artificial Sequence
<220> FEATURE:
<223> OTHER INFORMATION: ARTIFICIALLY SYNTHESIZED SEQUENCE
<220> FEATURE:
<221> NAME/KEY: mutation
<222> LOCATION: (28)..(29)
<223> OTHER INFORMATION: A  base deletion between the two bases
<220> FEATURE:
<221> NAME/KEY: mutation
<222> LOCATION: (38)..(39)
<223> OTHER INFORMATION: A  base deletion between the two bases

<400> SEQUENCE: 83
taatctggga gcctgcccta cttccagaat gcacagattc tgaggacaac                      50
```

```
<210> SEQ ID NO 84
<211> LENGTH: 13
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 84
taatctggga gcc                                                         13

<210> SEQ ID NO 85
<211> LENGTH: 12
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 85
tctgaggaca ac                                                          12

<210> SEQ ID NO 86
<211> LENGTH: 33
<212> TYPE: DNA
<213> ORGANISM: Homo sapiens

<400> SEQUENCE: 86
ctcacattca tggcctctga cagcgaggaa gaa                                    33

<210> SEQ ID NO 87
<211> LENGTH: 34
<212> TYPE: DNA
<213> ORGANISM: Artificial Sequence
<220> FEATURE:
<223> OTHER INFORMATION: ARTIFICIALLY SYNTHESIZED SEQUENCE
<220> FEATURE:
<221> NAME/KEY: mutation
<222> LOCATION: (22)..(22)
<223> OTHER INFORMATION: An inserted base

<400> SEQUENCE: 87
ctcacattca tggcctctga caagcgagga agaa                                   34

<210> SEQ ID NO 88
<211> LENGTH: 22
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 88
ctcacattca tggcctctga ca                                                22

<210> SEQ ID NO 89
<211> LENGTH: 12
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 89
agcgaggaag aa                                                          12

<210> SEQ ID NO 90
<211> LENGTH: 40
<212> TYPE: DNA
<213> ORGANISM: Homo sapiens
```

<400> SEQUENCE: 90
gttgtcctac ttccagaatg cacagatgtc tgaggacaac                     40

<210> SEQ ID NO 91
<211> LENGTH: 41
<212> TYPE: DNA
<213> ORGANISM: Artificial Sequence
<220> FEATURE:
<223> OTHER INFORMATION: ARTIFICIALLY SYNTHESIZED SEQUENCE
<220> FEATURE:
<221> NAME/KEY: mutation
<222> LOCATION: (28)..(28)
<223> OTHER INFORMATION: inserted base

<400> SEQUENCE: 91
gttgtcctac ttccagaatg cacagatgtt ctgaggacaa c                   41

<210> SEQ ID NO 92
<211> LENGTH: 30
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 92
gttgtcctac ttccagaatg cacagatgtt                                30

<210> SEQ ID NO 93
<211> LENGTH: 28
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 93
tccagaatgc acagattctg aggacaac                                  28

<210> SEQ ID NO 94
<211> LENGTH: 20
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 94
ctcacattca tggcctctga                                           20

<210> SEQ ID NO 95
<211> LENGTH: 36
<212> TYPE: DNA
<213> ORGANISM: Homo sapiens

<400> SEQUENCE: 95
cggcatcgac ctgggcacca cctactcctg cgtggg                         36

<210> SEQ ID NO 96
<211> LENGTH: 36
<212> TYPE: DNA
<213> ORGANISM: Homo sapiens

<400> SEQUENCE: 96
aggcatcgac ctgggcacca cctactcctg tgtggg                         36

```
<210> SEQ ID NO 97
<211> LENGTH: 36
<212> TYPE: DNA
<213> ORGANISM: Homo sapiens

<400> SEQUENCE: 97
cggcatcgac ctgggcacca cctattcgtg cgtcgg                           36

<210> SEQ ID NO 98
<211> LENGTH: 36
<212> TYPE: DNA
<213> ORGANISM: Homo sapiens

<400> SEQUENCE: 98
gggcatcgac ctgggcacca cctactcctg cgtggg                           36

<210> SEQ ID NO 99
<211> LENGTH: 36
<212> TYPE: DNA
<213> ORGANISM: Homo sapiens
<220> FEATURE:
<221> NAME/KEY: misc_feature
<222> LOCATION: (1)..(36)
<223> OTHER INFORMATION: n represents a, t, c or g

<400> SEQUENCE: 99
nggcatcgac ctgggcacca cctantcntg ngtngg                           36

<210> SEQ ID NO 100
<211> LENGTH: 18
<212> TYPE: DNA
<213> ORGANISM: Artificial Sequence
<220> FEATURE:
<223> OTHER INFORMATION: sgRNA encoding sequence

<400> SEQUENCE: 100
cccgtggtgg atgaggac                                               18

<210> SEQ ID NO 101
<211> LENGTH: 41
<212> TYPE: DNA
<213> ORGANISM: Homo sapiens

<400> SEQUENCE: 101
tcggcatcga cctgggcacc acctactcct gcgtgggggt g                     41

<210> SEQ ID NO 102
<211> LENGTH: 16
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 102
tcggcatcga cctggg                                                 16

<210> SEQ ID NO 103
<211> LENGTH: 25
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 103
caccacctac tcctgcgtgg gggtg                                       25
```

```
<210> SEQ ID NO 104
<211> LENGTH: 40
<212> TYPE: DNA
<213> ORGANISM: Artificial Sequence
<220> FEATURE:
<223> OTHER INFORMATION: ARTIFICIALLY SYNTHESIZED SEQUENCE
<220> FEATURE:
<221> NAME/KEY: mutation
<222> LOCATION: (16)..(17)
<223> OTHER INFORMATION: a base deletion between the two bases

<400> SEQUENCE: 104
tcggcatcga cctgggacca cctactcctg cgtggggtg                          40

<210> SEQ ID NO 105
<211> LENGTH: 41
<212> TYPE: DNA
<213> ORGANISM: Homo sapiens

<400> SEQUENCE: 105
taggcatcga cctgggcacc acctactcct gtgtgggggt g                       41

<210> SEQ ID NO 106
<211> LENGTH: 34
<212> TYPE: DNA
<213> ORGANISM: Artificial Sequence
<220> FEATURE:
<223> OTHER INFORMATION: ARTIFICIALLY SYNTHESIZED SEQUENCE
<220> FEATURE:
<221> NAME/KEY: mutation
<222> LOCATION: (9)..(10)
<223> OTHER INFORMATION: 7 bases deletion between the two bases

<400> SEQUENCE: 106
taggcatcgc accacctact cctgtgtggg ggtg                               34

<210> SEQ ID NO 107
<211> LENGTH: 12
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 107
taggcatcga cc                                                       12

<210> SEQ ID NO 108
<211> LENGTH: 25
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 108
caccacctac tcctgtgtgg gggtg                                         25

<210> SEQ ID NO 109
<211> LENGTH: 41
<212> TYPE: DNA
<213> ORGANISM: Homo sapiens

<400> SEQUENCE: 109
tgggcatcga cctgggcacc acctactcgt gcgtgggcgt g                       41
```

```
<210> SEQ ID NO 110
<211> LENGTH: 29
<212> TYPE: DNA
<213> ORGANISM: Artificial Sequence
<220> FEATURE:
<223> OTHER INFORMATION: ARTIFICIALLY SYNTHESIZED SEQUENCE
<220> FEATURE:
<221> NAME/KEY: mutation
<222> LOCATION: (6)..(7)
<223> OTHER INFORMATION: 12 basese deletion between the two bases

<400> SEQUENCE: 110
taggcaccac ctactcctgt gtggggtg                                      29

<210> SEQ ID NO 111
<211> LENGTH: 35
<212> TYPE: DNA
<213> ORGANISM: Artificial Sequence
<220> FEATURE:
<223> OTHER INFORMATION: ARTIFICIALLY SYNTHESIZED SEQUENCE
<220> FEATURE:
<221> NAME/KEY: mutation
<222> LOCATION: (10)..(11)
<223> OTHER INFORMATION: 6 bases deletion between the two sequences

<400> SEQUENCE: 111
tgggcatcga caccacctac tcgtgcgtgg gcgtg                              35

<210> SEQ ID NO 112
<211> LENGTH: 53
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 112
cgacctgggc accacctact cctgcgtggg ggtgttccaa cacggcaagg tgg          53

<210> SEQ ID NO 113
<211> LENGTH: 53
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 113
cgacctgggc accacctact cctgtgtggg ggtgttccag cacggcaagg tgg          53

<210> SEQ ID NO 114
<211> LENGTH: 53
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 114
cgacctgggc accacctact cgtgcgtggg cgtgtttcag cagggccgcg tgg          53

<210> SEQ ID NO 115
<211> LENGTH: 53
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 115
cgacctgggc accacctatt cgtgcgtcgg ggtcttccaa catggcaagg tgg          53
```

```
<210> SEQ ID NO 116
<211> LENGTH: 21
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 116
ctcacattca tggcctctga c                                              21

<210> SEQ ID NO 117
<211> LENGTH: 36
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 117
gggcatcgac ctgggcacca cctactcgtg cgtggg                              36

<210> SEQ ID NO 118
<211> LENGTH: 31
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 118
ggcatcgacc tgggcaccac ctatctggtg g                                   31

<210> SEQ ID NO 119
<211> LENGTH: 29
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 119
tgggcaccac ctactcgtgc gtgggcgtg                                      29
```

GENE KNOCKOUT METHOD

CROSS REFERENCE TO RELATED APPLICATIONS

This application is a National Phase application under 35 U.S.C. § 371 of International Application No. PCT/CN2017/096510, filed Aug. 8, 2017, the contents of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 794922001200SEQLIST.txt, date recorded: Jun. 29, 2022, size: 23,114 bytes).

FIELD OF THE INVENTION

The present invention relates to the genome editing technology, in particular to a gene knockout method.

BACKGROUND OF THE INVENTION

The genome editing technology has revolutionized experimental researches on gene functions. Three major technologies, ZFNs (zinc finger nucleases) [1], TALENs (transcription activator-like effector nucleases) [2-4] and CRISPR/Cas9 systems [5-7], employ different mechanisms to generate sequence-specific double-strand breaks (DSBs) and subsequently trigger natural repair systems to complete sequence-specific modifications [8, 9]. These technologies have been widely applied in functional gene researches [10], dynamic and real-time imaging of chromosomal sites [11, 12], correction of disease mutations [13], gene therapy [14] and other aspects. The CRISPR/Cas9 system has become particularly popular for its efficiency and ease of operation. The CRISPR/Cas9 system was originally used by the bacterial immune system to fight against foreign viruses or plasmids. In a class II CRISPR system, a Cas9 endonuclease cleaves a double-stranded DNA under the guidance of an sgRNA, resulting in a double-strand break in the genome and production of repair errors (base deletions or insertions) by making use of the instability of the cell genome repair, thereby achieving the effect of genome editing.

Although the CRISPR/Cas9 system has unprecedented advantages in design- and sequence-specificity-based genomic researches, the genome editing triggered by the CRISPR/Cas9 system is still a rare event in a cell population. It requires tedious labour to get real genetically edited single clones. Therefore, the system is still technically challenging, even for a simple task of producing a gene knockout in a mammalian cell [15]. Various efforts have been made to improve the efficiency of the protocol of producing the gene knockout, for instance, integrating the CRISPR/Cas9 system to permanently express the Cas9 and sgRNA [16], pregenerating a cell line stably expressing the Cas9 [17], enhancing the non-homologous end joining (NHEJ) pathway [18], enriching gene-targeted events by simultaneously disrupting an individual gene to achieve specific drug selection [19], and enriching gene knockouts by surrogate reporters [20, 21]. However, various shortcomings limit the wide application of these technologies. In particular, it remains a difficult task to generate multi-gene knockouts in a mammalian cell. When using a traditional method, it is sometimes a time-consuming, onerous and high-risk task even to knock out a single gene [22], as such method lacks effective enrichment for rare clones containing target gene modifications.

If the disruption of a target gene can result in a phenotypic change that can be used for enrichment, gene knockout clones can be easily obtained, for instance, Hela CSPG4$^{-/-}$ cells achieved resistance to *Clostridium difficile* toxin B [23]. However, this strategy is not universal. The traditional method involves co-transfection of plasmids expressing antibiotic resistance or fluorescent proteins [23, 24]; however, this method cannot enrich a limited number of cells containing targeted modifications.

h has been reported that exogenous dsDNA fragments may be integrated into chromosomal sites with DSBs through different repair mechanisms. Long flanking sequences need to be constructed for the homologous recombination (HR) repair which is with a low integration efficiency; while the integration efficiency of the non-homologous end joining (NHEJ) DNA repair [27, 28] is usually higher than that of the homologous recombination repair [29]. Previous studies have used NHEJ triggered by the CRISPR/Cas to mediate insertion of exogenous linear donor DNAs to achieve the purpose of a gene knockin [30-34].

SUMMARY OF THE INVENTION

The present invention provides a donor construct and a gene knockout method, as well as a system and kit for the gene knockout. The gene knockout method of the present invention uses a marker gene comprised in the donor construct to enrich cells in which a gene is knocked out, thereby improving the efficiency of a sequence-specific nuclease generated gene knockout.

According to one aspect of the present invention, a donor construct is provided, wherein the donor construct is a linear donor DNA or is capable of been cleaved in a cell to produce a linear donor DNA, and the linear donor DNA sequentially comprises, from the middle to both ends: an expression cassette; a short sequence extension comprising a reverse termination codon located at the 5'-end of the expression cassette and a short sequence extension consisting of a forward termination codon located at the 3'-end of the expression cassette; a target sequence located at the 5'-end and/or 3'-end, comprising a target site cleavable by the sequence-specific nuclease; and protective sequences located at both ends; wherein the expression cassette comprises a promoter-driven marker gene.

In the present invention, the linear donor DNA is a double-stranded linear donor DNA.

In a preferred embodiment, the donor construct is a linear donor DNA.

In some embodiments, the sequence-specific nuclease is a zinc finger nuclease (ZFN).

In some other embodiments, the sequence-specific nuclease is a transcription activator-like effector nuclease (TALEN).

In some other embodiments, the sequence-specific nuclease is a Cas9 nuclease.

In some other embodiments, the sequence-specific nuclease is an NgAgo nuclease.

In some embodiments, the linear donor DNA only has a target sequence at the 5'-end or the 3'-end.

In some embodiments, the linear donor DNA has target sequences at both ends, respectively.

In some embodiments, the target sequences at both ends of the linear donor DNA are the same.

In some embodiments, the target sequences at both ends of the linear donor DNA are different. In a further embodiment, the different target sequences at both ends of the linear donor DNA are derived from the same gene. In another further embodiment, the different target sequences at both ends of the linear donor DNA are derived from different genes.

In a preferred embodiment, the marker gene is an antibiotic resistance gene or a fluorescent protein gene.

In a preferred embodiment, the protective sequence is 5-30 bp, most preferably 20 bp, in length.

According to another aspect of the present invention, a method for generating a gene knockout in a cell is provided, comprising the steps of:

(1) introducing into a cell a sequence-specific nuclease capable of cleaving a specific target site in a cell genome, and a donor construct;

wherein the donor construct is a linear donor DNA or is capable of been cleaved in a cell to produce a linear donor DNA, and the linear donor DNA sequentially comprises, from the middle to both ends: an expression cassette; a short sequence extension consisting of a reverse termination codon located at the 5'-end of the expression cassette and a short sequence extension consisting of a forward termination codon located at the 3'-end of the expression cassette; a target sequence located at the 5'-end and/or 3'-end, comprising a target sequence cleavable by the sequence-specific nuclease; and protective sequences located at both ends; and the expression cassette comprises a promoter-driven marker gene;

wherein the linear donor DNA is inserted into the specific target site in the cell genome by non-homologous end joining; and (2) screening cells positive for the marker expression.

In the present invention, the linear donor DNA is a double-stranded linear donor DNA.

In a preferred embodiment, the donor construct is a linear donor DNA.

In some embodiments, the linear donor DNA only has a target sequence at the 5'-end or the 3'-end.

In some embodiments, the linear donor DNA has target sequences at both ends, respectively.

In some embodiments, the target sequences at both ends of the linear donor DNA are the same.

In some embodiments, the target sequences at both ends of the linear donor DNA are different. In a further embodiment, the different target sequences at both ends of the linear donor DNA are derived from the same gene. In another further embodiment, the different target sequences at both ends of the linear donor DNA are derived from different genes.

In some embodiments, the sequence-specific nuclease is a zinc finger nuclease (ZFN).

In some other embodiments, the sequence-specific nuclease is a transcription activator-like effector nuclease (TALEN).

In some other embodiments, the sequence-specific nuclease is a Cas9 nuclease.

In a preferred embodiment, the method further comprises introducing into the cell a guide RNA (gRNA) that recognizes a specific target site in the cell genome, wherein the target sequence in the linear donor DNA is recognized by the gRNA.

In some embodiments, the gRNA is an sgRNA.

In a more preferred embodiment, the method further comprises introducing into the cell an sgRNA that recognizes a single specific target site in the cell genome, wherein the target sequence comprising the target site recognized by the sgRNA is located at the 5'-end and/or the 3'-end of the linear donor DNA. In some embodiments, the target sequence comprising the target site recognized by the sgRNA is derived from a single gene in the cell genome. In some embodiments, the target sequence comprising the target site recognized by the sgRNA is a consensus sequence of two or more genes in the cell genome, provided that the consensus sequence has no more than one base difference from the sequences in any of the two or more genes at positions corresponding to the consensus sequence.

In some more preferred embodiments, the method further comprises introducing into the cell two sgRNAs that recognize two specific target sites in one gene in the cell genome, wherein two target sequences respectively comprising the two target sites recognized by the two sgRNAs are located in two linear donor DNAs, respectively, or located at both ends of the same linear donor DNA, respectively.

In still some more preferred embodiments, the method further comprises introducing into the cell two or more sgRNAs that recognize two or more specific target sites in the cell genome, wherein two or more target sequences respectively comprising the two or more target sites recognized by the two or more sgRNAs are located at both ends of the same linear donor DNA, respectively, or located in different linear donor DNAs. The two or more specific target sites in the cell genome are located in different genes, respectively.

In some other embodiments, the sequence-specific nuclease is an NgAgo nuclease.

In a preferred embodiment, the method further comprises introducing into the cell a guide DNA (gDNA) that recognizes a specific target site in the cell genome, wherein the target sequence in the linear donor DNA comprises a target site recognized by the gDNA.

In the present invention, the gene knockout can be a single gene knockout or a multi-gene knockout. The multi-gene knockout is a knockout of two or more genes, such as a knockout of three, four, five or more genes.

In a preferred embodiment, the marker gene is an antibiotic resistance gene or a fluorescent protein gene.

In a preferred embodiment, the cells are screened by the drug resistance.

In another preferred embodiment, the cells are screened by the FACS method.

In a preferred embodiment, the protective sequence is 5-30 bp, most preferably 20 bp, in length.

According to another aspect of the present invention, a system or kit for the gene knockout is provided, comprising: a sequence-specific nuclease capable of cleaving a specific target site in the cell genome, and a donor construct;

wherein the donor construct is a linear donor DNA or is capable of been cleaved in a cell to produce a linear donor DNA, and the linear donor DNA sequentially comprises, from the middle to both ends: an expression cassette; a short sequence extension consisting of a reverse termination codon located at the 5'-end of the expression cassette and a short sequence extension consisting of a forward termination codon located at the 3'-end of the expression cassette; a target sequence located at the 5'-end and/or 3'-end, comprising a target sequence cleavable by the sequence-specific nuclease; and protective sequences located at both ends; and the expression cassette comprises a promoter-driven marker gene.

In the present invention, the linear donor DNA is a double-stranded linear donor DNA.

In some embodiments, the donor construct is a linear donor DNA. In some other embodiments, the donor construct is a circular donor construct that can be cleaved in a cell to produce a linear donor DNA.

In some embodiments, the sequence-specific nuclease is a zinc finger nuclease (ZFN).

In some other embodiments, the sequence-specific nuclease is a transcription activator-like effector nuclease (TALEN).

In some other embodiments, the sequence-specific nuclease is a Cas9 nuclease.

In a preferred embodiment, the system or kit further comprises an sgRNA that recognizes a specific target site in the cell genome, wherein the target sequence in the linear donor DNA comprises a target site recognized by the sgRNA.

In some embodiments, the gRNA is an sgRNA.

In some other embodiments, the sequence-specific nuclease is an NgAgo nuclease.

In a preferred embodiment, the system or kit further comprises a gDNA that recognizes a specific target site in the cell genome, wherein the target sequence in the linear donor DNA comprises a target site recognized by the gDNA.

In a preferred embodiment, the marker gene is an antibiotic resistance gene or a fluorescent protein gene.

In a preferred embodiment, the protective sequence is 5-30 bp, most preferably 20 bp, in length.

In the present invention, the cleavage is to generate double-strand breaks (DSBs).

According to another aspect of the present invention, a universal donor construct is provided, wherein the universal donor construct is a linear donor DNA or is capable of been cleaved in a cell to produce a linear donor DNA, and the linear donor DNA sequentially comprises, from the middle to both ends: an expression cassette; a short sequence extension consisting of a reverse termination codon located at the 5'-end of the expression cassette and a short sequence extension consisting of a forward termination codon located at the 3'-end of the expression cassette; a universal target sequence located at the 5'-end and/or 3'-end, comprising a target site cleavable by a Cas9 nuclease; and protective sequences located at both ends;

wherein the expression cassette comprises a promoter-driven marker gene; and wherein the universal target sequence is absent in a cell genome to be subjected to a gene knockout.

In some embodiments, the universal donor construct is a linear donor DNA.

In some embodiments, the linear donor DNA is a double-stranded linear donor DNA.

In some embodiments, the linear donor DNA only has the universal target sequence at the 5'-end or the 3'-end.

In some embodiments, the linear donor DNA has the universal target sequences at both ends, respectively.

In a preferred embodiment, the marker gene is an antibiotic resistance gene or a fluorescent protein gene.

In a preferred embodiment, the protective sequence is 5-30 bp, most preferably 20 bp, in length.

In a preferred embodiment, the universal target sequence in the universal donor construct comprises 5'-GTACGGGGCGATCATCCACA-3' (SEQ ID NO:1) or 5'-AATCGACTCGAACTTCGTGT-3' (SEQ ID NO:2).

According to another aspect of the present invention, a method for generating a gene knockout in a cell is provided, comprising the steps of:

(1) introducing into the cell:
 (a) a Cas9 nuclease;
 (b) a gRNA that recognizes a specific target sequence in a cell genome;

(c) a universal donor construct, wherein the universal donor construct is a linear donor DNA or is capable of been cleaved in a cell to produce a linear donor DNA, and the linear donor DNA sequentially comprises, from the middle to both ends: an expression cassette; a short sequence extension consisting of a reverse termination codon located at the 5'-end of the expression cassette and a short sequence extension consisting of a forward termination codon located at the 3'-end of the expression cassette; a universal target sequence located at the 5'-end and/or 3'-end, comprising a target site cleavable by a Cas9 nuclease; and protective sequences located at both ends;

wherein the expression cassette comprises a promoter-driven marker gene; and wherein the universal target sequence is absent in the cell genome to be subjected to a gene knockout; and (d) a gRNA that recognizes the universal target sequence contained in the linear donor DNA;

(2) inserting the linear donor DNA into a specific target site in the cell genome by non-homologous end joining; and (3) screening cells positive for the marker expression.

In some embodiments, the donor construct is a linear donor DNA.

In some embodiments, the linear donor DNA is a double-stranded linear donor DNA.

In some embodiments, the linear donor DNA only has the universal target sequence at the 5'-end or the 3'-end.

In some embodiments, the linear donor DNA has the universal target sequences at both ends.

In some embodiments, the gRNA that recognizes the specific target site in the cell genome may be a gRNA, or a plurality of gRNAs that recognize different target sites in the cell genome, such as two, three, or more gRNAs that recognize different target sites in the cell genome. The different target sites may be located in the same gene or may be located in different genes. When the different target sites are located in different genes respectively, the knockout of multiple genes can be achieved.

Therefore, in the present invention, the gene knockout can be a single gene knockout or a multi-gene knockout. The multi-gene knockout is a knockout of two or more genes, such as a knockout of three, four, five or more genes.

In some embodiments, the gRNA that recognizes the specific target site in the cell genome is an sgRNA.

In some embodiments, the gRNA that recognizes the universal target sequence contained in the linear donor DNA is an sgRNA.

In some embodiments, the sgRNA that recognizes the specific target site in the cell genome and the sgRNA that recognizes the universal target sequence contained in the linear donor DNA are located in the same vector.

In some embodiments, the sgRNA that recognizes the specific target site in the cell genome and the sgRNA that recognizes the universal target sequence contained in the linear donor DNA are located in different vectors.

In a preferred embodiment, the marker gene is an antibiotic resistance gene or a fluorescent protein gene.

In a preferred embodiment, the cells are screened by the drug resistance.

In another preferred embodiment, the cells are screened by the FACS method.

In a preferred embodiment, the protective sequence is 5-30 bp, most preferably 20 bp, in length.

In a preferred embodiment, the universal target sequence in the universal donor construct comprises 5'-GTACGGGGCGATCATCCACA-3' (SEQ ID NO:1) or 5'-AATCGACTCGAACTTCGTGT-3' (SEQ ID NO:2).

According to another aspect of the present invention, a system or kit for a gene knockout is provided, comprising:

(1) a Cas9 nuclease or a vector or cell capable of expressing the Cas9 nuclease;

(2) a gRNA that recognizes a specific target sequence in a cell genome;

(3) a universal donor construct, wherein the universal donor construct is a linear donor DNA or is capable of been cleaved in a cell to produce a linear donor DNA, and the linear donor DNA sequentially comprises, from the middle to both ends: an expression cassette; a short sequence extension consisting of a reverse termination codon located at the 5'-end of the expression cassette and a short sequence extension consisting of a forward termination codon located at the 3'-end of the expression cassette; a universal target sequence located at the 5'-end and/or 3'-end, comprising a target site cleavable by a Cas9 nuclease; and protective sequences located at both ends;

wherein the expression cassette comprises a promoter-driven marker gene; and wherein the universal target sequence is absent in the cell genome to be subjected to a gene knockout; and (4) a gRNA that recognizes the universal target sequence contained in the linear donor DNA.

In some embodiments, the linear donor DNA is a double-stranded linear donor DNA.

In some embodiments, the donor construct is a linear donor DNA.

In some other embodiments, the donor construct is a circular donor construct that can be cleaved in a cell to produce a linear donor DNA.

In some embodiments, the gRNA that recognizes the specific target sites in the cell genome may be a gRNA, or a plurality of gRNAs that recognize different target sites in the cell genome, such as two, three, or more gRNAs that recognize different target sites in the cell genome. The different target sites may be located in the same gene or may be located in different genes. When the different target sites are located in different genes respectively, the knockout of multiple genes can be achieved.

In some embodiments, the gRNA that recognizes the specific target sequence in the cell genome is an sgRNA.

In some embodiments, the gRNA that recognizes the universal target sequence contained in the linear donor DNA is an sgRNA.

In some embodiments, the gRNA that recognizes the specific target site in the cell genome and the gRNA that recognizes the universal target sequence contained in the linear donor DNA are located in the same vector.

In some embodiments, the gRNA that recognizes the specific target site in the cell genome and the gRNA that recognizes the universal target sequence contained in the linear donor DNA are located in different vectors.

In a preferred embodiment, the marker gene is an antibiotic resistance gene or a fluorescent protein gene.

In a preferred embodiment, the protective sequence is 5-30 bp, most preferably 20 bp, in length.

In the present invention, the cleavage is to generate double-strand breaks (DSBs).

In a preferred embodiment, the target sequence in the universal donor construct comprises 5'-GTACGGGGCGATCATCCACA-3' (SEQ ID NO:1) or 5'-AATCGACTCGAACTTCGTGT-3' (SEQ ID NO:2).

In the present invention, by inserting a marker gene into a cleavage target site for the gene knockout, rare clones with the generated gene knockout can be effectively enriched through the marker. The present invention is particularly useful for targeting genes of which sgRNAs designing is difficult, and in cases where several gene knockouts need to be targeted simultaneously. The present method is helpful for various genome editing systems that produce DNA double-strand breaks, especially for the wider application of the CRISPR system in the biomedical field of genes and gene functions.

BRIEF DESCRIPTION OF THE DRAWINGS

FIGS. 1A-1C show the donor design and experimental verification of enrichment of cells containing Cas9/gRNA-targeting mutations in the ANTXR1 gene in HeLa cells by puromycin selection. FIG. 1A A schematic diagram of NHEJ-based knockin of linear donor at an sgRNA- or pgRNA-targeting site in the ANTXR1 gene. The genomic site and linear donor have cleavage sequences sg1 and sg2 for the gRNA. The termination codon is marked with ***, and the arrow points in the direction of the reading frame. FIG. 1B MTT staining of puromycin-resistant clones of cells transfected with a donor (with or without a gRNA).

FIG. 1C Comparison of ANTXR1 knockout rates of HeLa cells transfected with sgRNA/pgRNA (with (a dark-colored bar) or without (a light-colored bar) the corresponding donors). The ANTXR1 knockout rate is expressed as the percentage of cells resistant to PA/LFnDTA. Cells were selected with puromycin (1 μg/ml) prior to the PA/LFnDTA resistance analysis. Error bars indicate s.d. (n=3), t-test, P<0.01, *P<0.001. FIG. 1D Summary of ANTXR1 knockout cells enriched when using different gRNAs and their donors.

FIG. 2A Images of different HeLa cell groups treated with or without PA/LFnDTA. Mixed cells were obtained by transfection using sgRNA or pgRNA with or without the corresponding linear donors. The plotting scale is 200 μm. FIG. 2B PCR verification of the linear donor-integrated ANTXR1 locus of puromycin-resistant (puro+) single clones. The clones were obtained from HeLa cells transfected with sgRNA2$_{ANTXR1}$/Donor$_{ANTXR1-sg2}$ (left) or pgRNA$_{ANTXR1}$/Donor$_{ANTXR1-pg}$ (right).

FIGS. 3A-3D show the donor design and experimental verification of enrichment of HEBGF disruption events in HeLa cells by puromycin selection. FIG. 3A Design of a donor targeting the HBEGF gene. FIG. 3B MTT staining of puromycin-resistant clones of cells transfected with linear donor Donor$_{HBEGF-sg1}$ (with or without Cas9/sgRNA). FIG. 3C Images of different HeLa cell groups treated with or without DT (40 ng/ml). Pooled population was obtained by transfection using an sgRNA (sgRNA1HBEGF) (with or without its corresponding linear donor (Donor$_{HBEGF-sg1}$). The plotting scale is 200 μm. FIG. 3D HBEGF knockout rates of HeLa cells transfected with an sgRNA (sgRNA1HBEGF), a Cas9-expressing plasmid, and a reporter plasmid containing a puromycin-resistant gene (a light-colored bar), or with an sgRNA, a Cas9-expressing plasmid, and a linear donor (Donor$_{HBEGF-sg1}$) (a dark-colored bar). The HBEGF knockout rate is expressed as the percentage of cells resistant to DT. Cells were selected by puromycin (1 μg/ml) prior to the DT resistance analysis. Error bars indicate s.d. (n=3), t-test, ***P<0.001.

FIG. 4A Design of a donor targeting the HBEGF gene. FIG. 4B Images of different HEK293T cell groups treated with or without DT (40 ng/ml). Pooled cells were obtained by transfection using sgRNA (sgRNA2HBEGF) (with or without its corresponding linear donor (Donor$_{HBEGF-sg2}$)). The plotting scale is 200 µm. FIG. 4C HBEGF knockout rates of HEK293T cells transfected with an sgRNA (sgRNA2HBEGF) plasmid expressing mCherry, and a plasmid expressing Cas9 (a light-colored bar), or with an sgRNA, a plasmid expressing Cas9, and a linear donor (Donor$_{HBEGF-sg2}$, EGFP) (a dark-colored bar). The HBEGF knockout rate is expressed as the percentage of cells resistant to DT. Cells were selected by FACS prior to the DT resistance analysis. Error bars indicate s.d. (n=3), t-test, ***P<0.05.

FIGS. 5A-5F show the donor design and experimental verification of enrichment of ANTXR1 disruption events in HeLa$_{oc}$ cells by puromycin selection. FIG. 5A Design of a donor targeting ANTXR1. The donor comprises an sgRNA cleavage sequence at the 5'-end (Donor$_{ANTR1-sg1}$ or Donor$_{ANTXR1-sg2}$) or two gRNAs at both ends (Donor$_{ANTXR1-pg}$). FIG. 5B MTT staining of puromycin-resistant clones of cells transfected with a donor (with or without a gRNA). FIG. 5C Images of different HeLa$_{oc}$ cell groups treated with or without PA/LFnDTA. Pooled cells were obtained by transfection using sgRNA or pgRNA with or without the corresponding linear donors. The plotting scale is 200 µm. FIG. 5D ANTXR1 knockout rates of HeLa$_{oc}$ cells transfected using sgRNAs with or without the corresponding donors. The ANTXR1 knockout rate is expressed as the percentage of cells resistant to PA/LFnDTA. Cells were selected by puromycin (1 µg/ml) prior to the PA/LFnDTA resistance analysis. Error bars indicate s.d. (n=3), t-test, ***P<0.001. FIG. 5E PCR verification of the linear donor-integrated ANTXR1 locus of puromycin-resistant single clones. FIG. 5F Summary of ANTXR1 knockout cells enriched when using different gRNAs and their donors.

FIGS. 6A-6B show the off-target assessment of a donor insertion in HeLa$_{oc}$ cells by splinkerette PCR (spPCR) analysis. FIG. 6A The adaptor and primer design for the spPCR analysis. Splink1 and Splink2 primers are complementary to the adaptor sequence, and primers R1 and R2 are complementary to the linear donor sequence. FIG. 6B The spPCR reaction results.

FIGS. 7A-7D show the donor design and experimental verification of enrichment of HBEGF disruption events in HeLa$_{oc}$ cells by puromycin selection. FIG. 7A Design of a donor targeting HBEGF. The donor comprises an sgRNA cleavage sequence at the 5'-end (Donor$_{HBEGF-sg1}$ or Donor$_{HBEGF-sg2}$) or two gRNAs at both ends (Donor$_{HBEGF-pg}$) FIG. 7B MTT staining of puromycin-resistant clones of cells transfected with a donor (with or without sgRNA/pgRNA). FIG. 7C PCR verification of the linear donor-integrated HBEGF locus of a puromycin-resistant single clone. FIG. 7D Summary of HBEGF knockout cells enriched when using different gRNAs and their donors.

FIGS. 8A-8F show the donor design and experimental verification of generation of two or more gene knockouts in one step in HeLa$_{oc}$ cells. FIG. 8A A schematic diagram of NHEJ-based knockin of a linear donor at an sgRNA- or pgRNA-targeting site in PSEN1 and PSEN2 genes. FIG. 8B-8C The sequencing analysis of partial encoding sequences of PSEN1 and PSEN2 in genome, comprising an sgRNA encoding region (underlined) and a mutant allele. Clone 1 (FIG. 8B) was derived from HeLa$_{oc}$ cells transfected with pgRNA$_{PsEN1+PsEN2}$/Donorp$_{PSEN1+PSEN2}$ Clone 2 (FIG. 8C) was derived from HeLa$_{oc}$ cells transfected with pgR-NA$_{PSEN1+PSEN2}$/Donor$_{PSEN1}$+Donor$_{PSEN2}$. The nucleotides in the shaded region represent the PAM sequence that directs Cas9 to perform DNA recognition and cleavage. Dashed lines indicate deletions, higher letters indicate nucleotide insertions, and light gray arrows in the background indicate the direction of the CMV promoter in the donor. FIG. 8D Multiple sequence alignment analysis of the HSPA gene family showing the consensus sequence; an sgRNA targeting the consensus sequence of five HSPA family genes; and the design of the universal linear donor (Donor$_{HSPA}$) for enrichment of cells containing multi-gene mutations. The black shaded nucleotides represent the consensus sequence of all the five HSPA genes. Dark gray shaded nucleotides represent the consensus sequence of three or four HSPA genes, while light gray shaded nucleotides represent non-consensus nucleotides.

FIG. 8E Indels triggered by sgRNA$_{HHSPA}$ in five target genes after puromycin selection in the absence and presence of Donor$_{HSP4}$. Error bars indicate s.d. (n=3), t-test, P<0.01, *P<0.001. FIG. 8F Partial encoding sequences of HSPA1A, HSPA1B, HSPA1L and HSPA6 genes in the genome of HeLa clone 3 comprising an sgRNA-targeting region (underlined). Clone 3 was derived from HeLa$_{oc}$ cells transfected with sgRNA$_{HHSPA}$/Donor$_{HSPA}$. The shaded nucleotides represent the PAM sequence, and the dashed lines represent deletions. Light gray arrows in the background indicate the direction of the CMV promoter in the donor.

FIGS. 9A-9C show the efficiency evaluation of PSEN1 and PSEN2 sgRNAs in HeLa$_{oc}$ cells and the single clone recognition. FIG. 9A Efficiency evaluation of indels caused by sgRNA$_{PSEN1}$, sgRNA$_{PSEN2}$ and pgRNA$_{PSEN}$ at PSEN1 and PSEN2 loci through the T7E1 analysis. Error bars indicate s.d. (n=3). FIG. 9B MTT staining of puromycin-resistant clones of cells transfected with a donor (with or without pgRNA$_{PSEN}$). FIG. 9C PCR results of the two linear donor-integrated PSEN1 (L3/R3) and PSEN2 (L4/R4) sites, of puromycin-resistant single clones.

FIG. 11A PCR verification results of linear donor integration of puromycin-resistant single clones at all the five gene loci. FIG. 11B Summary of donor insertion results at four gene loci, HSPA1A, HSPA1B, HSPA1L and HSPA6.

DETAILED DESCRIPTION OF THE INVENTION

Figure 2A:
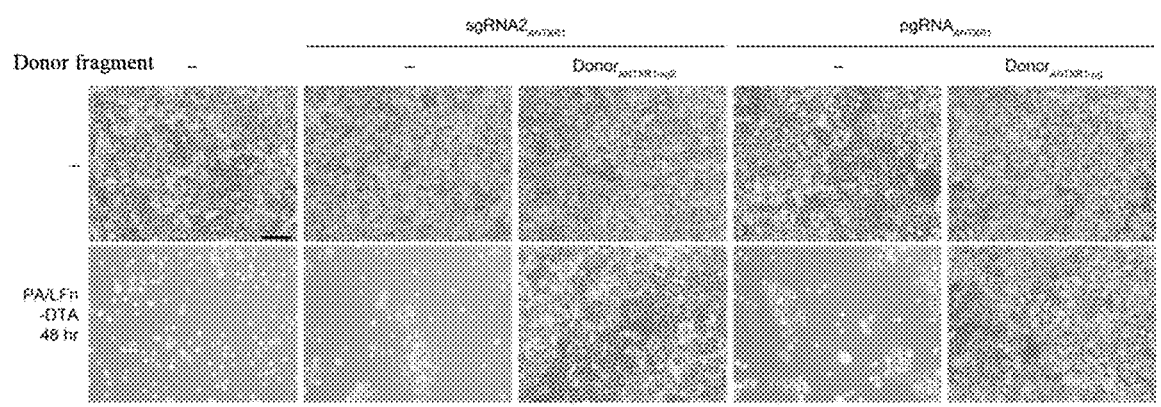
FIGS. 2A-2B show the experimental verification of enrichment of ANTXR1 knockout cells in a pooled population and single clones by donor-mediated puromycin resistance selection.

The present invention provides a novel donor construct and a gene knockout method. The method uses a linear donor DNA to improve the efficiency of generating a gene knockout by a sequence-specific nuclease. The linear donor DNA of the present invention comprises at least one target site that can be cleaved by a sequence-specific nuclease. The target site comprised in the linear donor DNA is designed according to the target site in the cell genome, so that a sequence-specific nuclease that can cleave the target site in the cell genome can also cleave the target site comprised in the linear donor DNA. After a sequence-specific nuclease and a donor construct are introduced into a cell, double-strand breaks (DSBs) are generated at a specific target site in the cell by the sequence-specific nuclease, and at the same time the sequence-specific nuclease cleaves at least one target site contained in the linear donor DNA. This allows the linear donor DNA to be inserted into the cleaved target site in the cell genome by the non-homologous end joining (NHEJ) pathway with a higher efficiency. Subsequent selection of cells through a marker can effectively enrich cells in which a gene is knocked out by cleavage at the specific target site of the genome, thereby greatly improving the efficiency of generating the gene knockout by the sequence-specific nuclease.

The target site comprised in the linear donor DNA is designed according to the target site in the cell genome, and the linear donor DNA obtained is a specific linear donor. When gene knockouts are required at different target sites in the cell genome, it is necessary to construct a matched linear donor DNA according to the sequence of the target site. Therefore, in order to further optimize the present invention, the inventors further provide a universal linear donor DNA in the present invention. The universal linear donor DNA comprises a universal target sequence that can be cleaved by a sequence-specific nuclease. The universal target sequence is absent in the cell genome to be subjected to a gene knockout, i.e., there is no sequence, which is identical to the universal target sequence and cleavable by the sequence-specific nuclease, in the cell genome to be subjected to a gene knockout. In this case, after a sequence-specific nuclease and a universal linear donor DNA are introduced into a cell, a sequence-specific nuclease generates double-strand breaks (DSBs) at a specific target site in the cell, and the universal target sequence contained in the universal linear donor DNA is also cleaved by the sequence-specific nuclease through a universal gRNA that recognizes the target sequence. At this time, the linear donor DNA can still be inserted into the cleaved target site in the cell genome by the non-homologous end joining (NHEJ) pathway with a higher efficiency. Subsequent selection of cells through a marker can effectively enrich cells in which a gene is knocked out by cleavage at the specific target site of the genome, and can also greatly improve the efficiency of generating a gene knockout by the sequence-specific nuclease. The target sequence in the universal linear donor DNA is not relevant to the gene to be knocked out, and it can be used as a universal donor for the knockout of different target genes in different cells, and can improve the efficiency of generating a gene knockout by the sequence-specific nuclease. A universal linear donor DNA is particularly useful in the case of gene knockout using the Cas9/CRISPR system which targets a target sequence using a gRNA (preferably an sgRNA). When gene knockout is performed, it is only necessary to construct a gRNA for a specific target site in the cell genome, without the need to specifically construct a matched linear donor DNA, i.e., a universal linear donor DNA and a gRNA targeting the universal linear donor DNA can be directly used, thereby reducing the operation complexity and improving the efficiency.

It has been reported that if one of the homologous alleles is modified, the mutation frequency of the target alleles is usually higher [25, 26]. Thus, while not wishing to be bound by theory, the inventors speculate that if a donor can be inserted at a specific site in one of the target alleles, and clones that express a marker gene contained in the donor are selected, it may be possible to enrich rare events where all the alleles are modified.

In the present invention, the "gene knockout" is to realize the loss of gene functions through genome editing. The gene knockout effect that is usually pursued is simultaneous knockout of two alleles, at which time the corresponding protein loses its functions and a gene knockout cell line is obtained. If only one allele is knocked out, the protein can also play its partial role, i.e., the protein functions are only down-regulated. Cells with both alleles knocked out can be enriched effectively by using the linear donor DNA and the method of the present invention.

The donor construct of the present invention is a double-stranded DNA. The donor construct of the present invention may itself be a linear donor DNA. Alternatively, the donor construct of the present invention may be a circular DNA molecule comprising a linear donor DNA, and when introduced into a cell, it is cleaved in the cell to produce the linear donor DNA. A method for cleaving a circular donor construct in a cell to produce a linear donor DNA is well known in the art. For instance, the circular construct can further comprise cleavage sites for another sequence-specific nuclease upstream of the 5'-end and downstream of the 3'-end of the linear donor DNA.

The method of the present invention may further comprise introducing to the cell another sequence-specific nuclease, which cleaves a sequence upstream of the 5'-end and downstream of the 3'-end of the linear donor DNA in the circular construct in the cell, thereby producing the linear donor DNA.

In the linear donor DNA of the present invention, the "reverse termination codon" means the codon oriented in the opposite direction to the reading frame of the expression cassette. The "forward termination codon" means the codon oriented in the same direction as the reading frame of the expression cassette. The role of termination codons is that, regardless of whether the linear donor is inserted into the genome forward or backward, both the triplet termination codons can terminate endogenous and exogenous gene expression.

The "protective sequence" in the linear donor DNA of the present invention can be any sequence, and preferably the protective sequence is different from the target sequence in the same linear donor DNA. The protective sequence can be 5-30 bp, preferably 20 bp, in length. The role of the protective sequence is to protect the target sequence in the linear donor DNA from being cleaved by an enzyme (e.g., an exonuclease) in the cell.

The "marker gene" described herein refers to any marker gene whose expression can be selected or enriched, i.e., when the marker gene is expressed in a cell, cells expressing the marker gene can be selected and enriched in a certain manner. The marker gene useful in the present invention includes, but is not limited to, a fluorescent protein gene that can be sorted by FACS after expression, or a resistance gene that can be screened by an antibiotic, or a protein gene that can be recognized by a corresponding antibody and screened by immunostaining or magnetic beads adsorption after expression. The resistance gene useful in the present invention includes, but is not limited to, resistance genes against Blasticidin, Geneticin (G-418), Hygromycin B, Mycophenolic Acid, Puromycin, Zeocin or Neomycin. The fluorescent protein gene useful in the present invention includes, but is not limited to, genes of Cyan Fluorescent Protein, Green Fluorescent Protein, Yellow Fluorescent Protein, Orange Fluorescent Protein, Red Fluorescent Protein, Far-Red Fluorescent Protein, or Switchable Fluorescent Proteins.

Examples of the sequence-specific nuclease comprises a zinc finger nuclease (ZFN). The zinc finger nuclease is a non-naturally occurring and artificially modified endonuclease, which is composed of a zinc finger protein domain and a non-specific endonuclease domain. The zinc finger protein domain comprises a series of Cys2-His2 zinc finger proteins in series. Each zinc finger protein recognizes and binds to a specific base triplet on the DNA strand in the 3' to 5' direction and a base in the 5' to 3' direction. Multiple zinc finger proteins can be connected in series to form a zinc finger protein group, which recognizes a stretch of specific base sequence with a strong specificity. The non-specific endonuclease linked to the zinc finger protein group is derived from the DNA cleavage domain consisting of 96 amino acid residues at the carboxyl terminus of FokI. Each FokI monomer is linked to a zinc finger protein group to form a ZFN that recognizes a specific site. When two recognition sites are at an appropriate distance (6-8 bp), two monomeric ZFNs interact with each other to produce an enzymatic digestion function, so as to achieve the purpose of site-specific DNA cleavage. 8-10 zinc finger domains are designed for the target sequence. By linking these zinc finger domains to DNA nucleases, double-strand breaks (DSBs) of the target sequences can be produced, and the DSB repair mechanism can be thus induced to conduct directional modification of specific sites in the genome.

Another example of the sequence-specific nuclease comprises a transcription activator-like effector nuclease (TALEN). The transcription activator-like effector nuclease is mainly composed of a Fok I endonuclease domain and a DNA binding domain of the TALE protein. The TALE protein contains multiple peptide segment repeats, each of which comprises 33-35 amino acids, and each peptide segment recognizes one base. Like ZFNs, TALENs can also cleave DNA target sequences to form DSBs, thereby activating DNA damage repair mechanisms and performing site-specific modification of the genome.

Another example of the sequence-specific nuclease system useful in the present invention comprises the Cas9/CRISPR (Clustered Regularly Interspaced Short Palindromic Repeats) system. The Cas9/CRISPR system utilizes RNA-directed DNA binding for sequence-specific cleavage of a target DNA, in which a crRNA (CRISPR-derived RNA) binds to tracrRNA (trans-activating RNA) by base pairing to form a tracrRNA/crRNA complex, which directs the nuclease Cas9 protein to cleave the double-stranded DNA at a specific position in the target sequence that is paired with the crRNA. The target sequence paired with the crRNA is usually a sequence of about 20 nucleotides located upstream of the genomic PAM (protospacer adjacent motif) site (NNG).

The Cas9 protein cleaves the target site by means of a guide RNA. The term "guide RNA" is also known as gRNA (guide RNA). A gRNA typically comprises a nucleotide on the crRNA complementary to the target sequence and an RNA scaffold formed by base pairing of the crRNA and the tracrRNA, and is capable of recognizing the target sequence paired with the crRNA. The gRNA can form a complex with the Cas9 protein and guide the Cas9 protein to the target sequence for cleaving the target site therein.

The gRNA is commonly used in the form of an sgRNA (single guide RNA). The sgRNA, also known as a "single-stranded guide RNA", is an RNA strand formed by fusing the crRNA with the trancrRNA.

Another example of the sequence-specific nuclease system useful in the present invention comprises an NgAgo nuclease and its gDNA. An NgAgo nuclease can bind to a single-stranded guide DNA (gDNA) phosphorylated at the 5'-end to cleave the target sequence complementary to the gDNA, thus producing DNA double-strand breaks.

The linear donor DNA of the present invention may have a target sequence only at one end, or may have target sequences at both ends, respectively. The target sequences at both ends of the linear donor DNA can be different. When a gene knockout is required to be produced by cleavage at two different target sites in the cell genome, two linear donor DNAs can be provided, and each linear donor DNA comprises a corresponding target sequence, respectively; or alternatively, a linear donor DNA can be provided, each end of which comprises a corresponding target sequence. When a gene knockout is required to be produced by cleavage at multiple different target sites in the cell genome, an appropriate number of linear donor DNAs can be provided, and one or both ends of each linear donor DNA comprises one of the multiple different corresponding target sequences, respectively. For instance, linear donor DNAs can be provided in the same number as the number of the target sites, and each linear donor DNA comprises a corresponding target sequence, respectively. Alternatively, linear donor DNAs may be provided in an number less than the number of the target sites, wherein both ends of all or part of the linear donor DNAs comprise one of the multiple different corresponding target sequences, respectively, and each of other linear donor DNAs comprises one of the other corresponding target sequences, respectively.

For a universal linear donor DNA comprising a universal target sequence, the universal target sequence may be contained at either end or both ends. The target sequence of such universal linear donor DNA is independent of the target sites to be cleaved in the cell genome, and is thus universally applicable to the case of generating a gene knockout by the cleavage of any one target site, any two target sites, or any more target sites in the cell genome.

The "universal target sequence" of the present invention refers to a sequence that can be cleaved by a sequence-specific nuclease. However, the universal target sequence is absent in the cell genome to be subjected to a gene knockout, in other words, there is no sequence, which is identical to the universal target sequence and cleavable by the sequence-specific nuclease, in the cell genome to be subjected to a gene knockout. The universal target sequence is different from the target sequence that is present in the cell genome and cleavable by the same sequence-specific nuclease. The linear donor DNA comprising the universal target site is not specific to any target site in the cell genome, and is thus universally applicable to the gene knockout of any gene in the cell, without the need to construct a specific linear donor DNA for the gene to be knocked out and the target site in the gene.

The sequence-specific nuclease can be introduced into a cell in the form of a protein or its coding nucleic acid sequence (e.g., an mRNA or a cDNA). A nucleic acid encoding the sequence-specific nuclease can be introduced into a cell by inclusion in a plasmid or viral vector, e.g., introduced into a cell by transfection. A nucleic acid encoding the sequence-specific nuclease can also be delivered directly to a cell by electroporation, liposome, microinjection, or other means.

The donor construct can be delivered by any method suitable for introducing a nucleic acid into a cell, e.g., introduced into a cell by transfection.

In the cases of producing gene knockouts using the Cas9/CRISPR system and the NgAgo nuclease, an sgRNA or a gDNA should also be introduced into a cell. The sgRNA or gDNA can be delivered by any method suitable for introducing an RNA or a DNA into a cell. The sgRNA can be introduced into a cell in the form of an isolated RNA. The isolated sgRNA can be prepared by in vitro transcription using any in vitro transcription system known in the art. The sgRNA can also be introduced into a cell by a vector comprising an sgRNA coding sequence and a promoter. The vector may be a viral vector or a plasmid. The means for introduction into a cell can be transfection.

Two or more sgRNAs for different respective target sites can be introduced into a cell to direct cleavage by Cas9 at two or more different target sites in the cell genome to produce gene knockouts. The two or more sgRNAs may be comprised in different vectors, or may be contained in the same vector, such as a vector comprising a pair of gRNAs (paired gRNAs), or a vector comprising more sgRNAs.

In the method of the present invention, when two or more sgRNAs for different respective target sites are introduced into a cell, linear donor DNAs comprising target sequences recognized by these sgRNAs are simultaneously introduced. Since the linear donor DNA may comprise a target sequence only at the 5'-end or 3'-end, or may also comprise target sequences at both ends, respectively, the number of sgRNAs and the number of linear donor DNAs can be different, i.e., it is possible that one sgRNA corresponds to one linear donor DNA, or two sgRNAs correspond to two linear donor DNAs.

When the Cas9/CRISPR system and the universal linear donor DNA of the present invention are used for a gene knockout, in addition to introducing the universal linear donor DNA and the Cas9 nuclease into a cell, an sgRNA for a specific target sequence in the cell genome and an sgRNA for a universal target sequence on the universal linear donor DNA are also introduced into the cell, so as to direct the Cas9 to cleave the specific target sequence in the cell genome and the universal target sequence on the universal linear donor DNA. An sgRNA for a specific target sequence in the cell genome and an sgRNA for a universal target sequence on the universal linear donor DNA may be comprised in different vectors, or may be comprised in the same vector.

An sgRNA for a specific target sequence in the cell genome may be one sgRNA or more sgRNAs, such as two, three, or more gRNAs. The more than one sgRNA may target different specific target sites in the cell genome respectively, so as to achieve simultaneous cleavage on different target sites in the cell genome. When these different target sites are located in different genes respectively, the knockout of multiple genes, such as of two, three or more genes, can be achieved. Specifically, when the multi-gene knockout is performed, a plurality of sgRNAs for a plurality of respective specific target sites in the cell genome and an sgRNA for a universal target sequence on the universal linear donor DNA may be introduced into the cell, so as to direct the Cas9 to cleave the plurality of specific target sites in the cell genome and the universal target sequence on the universal linear donor DNA. The plurality of specific target sequences are located on different genes respectively, thereby achieving the multi-gene knockout. The plurality of sgRNAs for the plurality of respective specific target sites in the cell genome may be comprised in different vectors, or may be comprised in the same vector. Any one or more sgRNAs of the plurality of sgRNAs for the plurality of respective specific target sites in the cell genome, and an sgRNA for a universal target sequence on the universal linear donor DNA may be comprised in different vectors, or may be comprised in the same vector.

According to the present invention, the universal target sequence on the universal donor construct DNA is preferably 5'-GTACGGGGCGATCATCCACA-3' (SEQ ID NO:1) or 5'-AATCGACTCGAACTTCGTGT-3' (SEQ ID NO:2).

Preferably, in the present invention, in the case of producing a gene knockout using the Cas9/CRISPR system, a Cas9, an sgRNA and a linear donor DNA can be introduced into a cell simultaneously; or for instance, a Cas9 can be first introduced into a cell, and then an sgRNA and a linear donor DNA are introduced into the cell. In some embodiments, the cell is co-transfected with a Cas9-containing vector, an sgRNA-containing vector, and a linear donor DNA. In some other embodiments, a Cas9 and an sgRNA are assembled in vitro into a protein-RNA complex, which is used to co-transfect the cell with a linear donor DNA. In some other embodiments, a Cas9 and an sgRNA are stably expressed in the cell by lentivirus, and the cell is transfected with a linear donor DNA. In other embodiments, a Cas9 is first stably expressed in the cell, and the cell is then co-transfected with an sgRNA-containing vector and a linear donor DNA.

In the system or kit provided by the present invention for a gene knockout, a sequence-specific nuclease may be in the form of a protein or its coding nucleic acid sequence (e.g., an mRNA or a cDNA), such as in the form of a plasmid or viral vector comprising a nucleic acid encoding the sequence-specific nuclease. In the case of using the Cas9/CRISPR system, an sgRNA may be in the form of an isolated RNA, or in the form of a vector comprising an sgRNA coding sequence and a promoter, such as a viral vector or a plasmid vector.

The cell described herein can be any eukaryotic cell, such as an isolated animal cell, e.g., a totipotent cell, a pluripotent cell, an adult stem cell, a fertilized egg, a somatic cell, or the like. In some embodiments, the cell is a vertebrate cell. In some embodiments, the cell is a mammalian cell. In some embodiments, the cell is a human cell. In some embodiments, the cell is a cell from a cow, a goat, a sheep, a cat, a dog, a horse, a rodent, fish, and a primate. In some embodiments, the rodent comprises mice, rats, and rabbits.

The method of the present invention can be used to perform targeted gene knockout in a single gene or multiple genes in a cell, such as two, three, four, five or more targeted gene knockouts. Targeted gene knockout for multiple genes can be performed simultaneously or successively. For instance, sequence-specific nucleases or sequence-specific nuclease systems for two or more target genes can be introduced into a cell and then cells are subjected to enrichment screening. Alternatively, a sequence-specific nuclease(s) or a sequence-specific nuclease system(s) for one or more target genes can be first introduced into a cell and cells are subjected to enrichment screening, and then a sequence-specific nuclease(s) or a sequence-specific nuclease system(s) for other target genes can be introduced into the cell and the cells are subjected to enrichment screening. Different marker/marker genes can be used for different target genes. For instance, in the case of producing a gene knockout using the Cas9/CRISPR system, two or more sgRNAs for different respective target sites can be introduced into a cell, and a linear donor DNA(s) comprising target sequences recognized by these sgRNAs is(are) simultaneously introduced, as previously mentioned. When these different target sites are located in different genes, knockout of multiple genes can be achieved. Target sequences in an sgRNA and a linear donor DNA can also be designed by using the consensus sequence of two or more genes in the cell genome. At this point, an sgRNA recognizing a single specific target site in the cell genome can be introduced into a cell, and a linear donor DNA comprising a target sequence recognized by the sgRNA is simultaneously introduced, wherein the target sequence recognized by the sgRNA is the consensus sequence of two or more genes in the cell genome, in the condition that the consensus sequence has no more than one base difference from the sequences in any of the two or more genes at positions corresponding to the consensus sequence. A two-base difference may disrupt recognition by an sgRNA, as demonstrated in Example 7.

The target gene edited with the linear donor DNA of the present invention targets is not particularly limited, as long as double-strand breaks can be produced on it by the Cas9/CRISPR system. The target gene may be an exon, an intron or a regulatory sequence, or any combination thereof.

The term "comprise" or "contain", as used in the present invention, indicates "include, but are not limited to", "consist essentially of" or "consist of".

The present invention is further illustrated in conjunction with the following examples and the accompanying drawings, which are used for illustration purposes only and are not intended to limit the scope of the present invention. If not specially stated, the examples are all conducted in accordance with normal experimental conditions, such as those described in Sambrook J & Russell DW, Molecular cloning: a laboratory manual, 2001, or in accordance with the instructions provided by the manufacturers.

Example 1. Enrichment of ANTXR1 Gene Knockout Events in HeLa Cells Using Linear Donor DNAs 1. Design of sgRNAs Two sgRNAs targeting the first exon of the ANTXR1 gene in HeLa cells were designed, and their efficiency in producing deletions or insertion mutations (Indels) at target sites was verified by T7E1 assay. The verification results are shown in Table 1. The target sequence that sgRNA1$_{ANTXR1}$ targets is referred to as sg1 in this example, and the target sequence that sgRNA2$_{ANTXR1}$ targets is referred to as sg2 in this example.

random sequence, a reverse termination codon, CMV promoter-driven puromycin-resistant gene, a forward termination codon, and a 20-bp protective sequence, respectively. The random sequence is different from sg1 or sg2.

3. Transfection

HeLa cells were co-transfected with a Cas9-expressing plasmid, sgRNA2$_{ANTXR1}$ or pgRNA$_{ANTXR1}$, and the corresponding donors. As a control, HeLa cells were transfected with linear donor DNAs (Donor$_{ANTXR1-sg2}$, Donor$_{ANTXR1-pg}$, and Donor$_{no\ cut}$) alone. To the cells puromycin was added for resistance screening. A pooled population and single clones were obtained and stained with MTT (3-(4,5-dimethylthiazol-2-yl)-2,5-diphenyltertazolium bromide). The results are shown in FIG. 1B.

A number of puromycin-resistant (puro+) cell clones were obtained from samples receiving sgRNA2$_{ANTXR1}$ and its corresponding donor Donor$_{ANTXR1-sg2}$, and from samples receiving pgRNA$_{ANTXR1}$ and its corresponding donor Donor$_{ANTXR1-pg}$. Only a few puromycin-resistant clones were produced by transfection with donors alone, probably because integration of linear donors into the chromosome was rare and random. In addition, co-transfection using the control donor Donor$_{no\ cut}$ with the Cas9-expressing plasmid and sgRNA2$_{ANTXR1}$ also failed to produce a significant number of puro+clones (see the rightmost panel in FIG. 1B), indicating that sgRNA-mediated cleavage by Cas9 in a donor is important for an effective donor integration. Integration of pgRNA$_{ANTXR1-sg2}$-mediated double-cleaved Donor$_{ANTXR1-pg}$ was more efficient than sgRNA2$_{ANTXR1}$ plus Donor$_{ANTXR1-sg2}$, however, no matter which linear donor DNA was used, sufficient puro+clones were produced for subsequent mutant identification.

4. Verification of Gene Knockout Efficiency

In addition, HeLa cells were co-transfected using a Cas9-expressing plasmid and sgRNA2$_{ANTXR1}$ or pgRNA$_{ANTXR1}$, with or without the corresponding donors. A pooled population and single clones were obtained by screening with puromycin (1 μg/ml). The plasmid expressing the puromy-

TABLE 1

The sgRNAs targeting the first exon of the ANTXR1 gene in HeLa cells

| sgRNA | Target sequence (PAM) (5' to 3') | SEQ ID NO: | Mean Indels ± s.d. (%, n = 3) |
|---|---|---|---|
| sgRNA1$_{ANTXR1}$ | AGCGGAGAGCCCTCGGCAT (CGG) | 3 | 19.97 ± 1.84 |
| sgRNA2$_{ANTXR1}$ | TGCTCATCTGCGCCGGGCAA (GGG) | 4 | 16.83 ± 2.05 |

2. Construction of Linear Donor DNAs

A total of two linear donor DNAs (DonorANTXR1-sg2 and DonorANTXR1-pg) were constructed, the structures of which are shown in FIG. 1A.

Donor$_{ANTXR1-sg2}$ comprises, from 5'-end to 3'- end: a 20-bp protective sequence, sg2, a reverse termination codon, CMV promoter-driven puromycin-resistant gene, a forward termination codon, and a 20-bp protective sequence, respectively.

Donor$_{ANTXR1-pg}$ comprises, from 5'-end to 3'-end: a 20-bp protective sequence, sg 1, a reverse termination codon, CMV promoter-driven puromycin-resistant gene, a forward termination codon, sg2, and a 20-bp protective sequence, respectively.

Figure 2B:
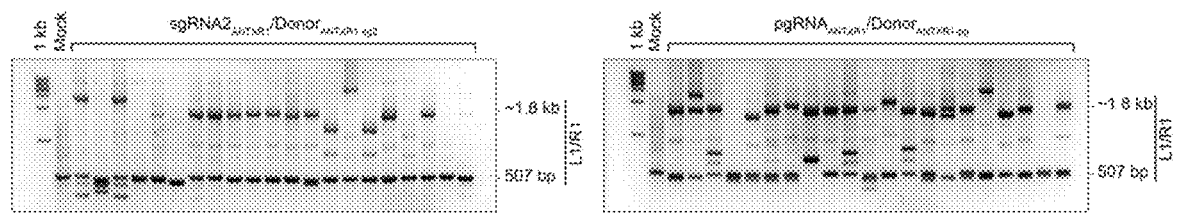

A linear donor DNA (Donor$_{no\ cut}$) as a control comprises, from 5'-end to 3'-end: a 20-bp protective sequence, a 20-bp cin-resistant gene is used for co-transfection instead, when the corresponding donors are not added. As the ANTXR1 gene knockout in HeLa cells results in resistance of the cells to chimeric anthrax toxin (PA/LFnDTA) [17], the pooled population and single clones obtained by puromycin screening were treated with PA/LFnDTA (PA: 150 ng/ml; and LFnDTA: 100 ng/ml) to compare the effect of linear donor DNAs on the ANTXR1 knockout efficiency. Images of different cells after being treated with PA/LFnDTA are shown in FIG. 2A. The ANTXR1 knockout efficiency was determined by calculating the percentage of cells with the toxin resistance in the puro+pooled population, as shown in FIG. 1C. Compared with the use of sgRNA2$_{ANTXR1}$ alone or pgRNA$_{ANTXR1}$ alone, the use of linear donor DNAs improved the gene knockout efficiency by 6 to 8 times. PCR verification was performed on the linear donor-integrated ANTXR1 site in puro+single clones. The L 1/R1 primer sequences used in PCR amplification are shown in Table 2. The results are shown in FIG. 2B, and it can be seen that most of the clones isolated from the puro+cell mixture contain donor inserts at the sgRNA-targeting sites (see also FIG. 1D). It can also be seen from FIG. 1D that nearly 90% of the cells carrying the donor fragment are real gene knockout clones.

TABLE 2

Primers for amplifying the linear donor-integrated ANTXR1 site in HeLa cells

| Primer pair | Sequence |
|---|---|
| L1/R1 | 5'-AAGCGGAGGACAGGATTGGG-3' (SEQ ID NO: 5) /5'-CCTCTGTGGCCCTGGAGATG-3' (SEQ ID NO: 6) |

Example 2. Enrichment of HBEGF Gene Knockout Events in HeLa Cells Using a Linear Donor DNA Since a donor with a single- or double-cleavage site is capable of greatly improving the selection of cells with a modification at a target site, for convenience, in this example, only a single-cleavage donor was adopted.

1. Design of sgRNAs

Two sgRNAs targeting the HBEGF gene in HeLa cells were designed, and their efficiency in producing Indels at target sites was verified by T7E1 assay. The verification results are shown in Table 3. The target sequence that sgRNA1$_{HBEGY}$ targets is referred to as sg 1 in this example, and the target sequence that sgRNA2$_{HBEGF}$ targets is referred to as sg2 in this example.

TABLE 3

The sgRNAs Targeting the HBEGF Gene in HeLa Cells

| sgRNA | Target sequence (PAM) (5' to 3') | SEQ ID NO: | Mean Indels ± s.d. (%, n = 3) |
|---|---|---|---|
| sgRNA1$_{HBEGF}$ | GACTGGCGAGAGCCTGGAG(CGG) | 7 | 32.03 ± 7.13 |
| sgRNA2$_{HBEGF}$ | CGGACCAGCTGCTACCCCT(AGG) | 8 | 14.27 ± 0.90 |

2. Construction of Linear Donor DNAs

A linear donor DNA (Donor$_{HBEGF-sg1}$) was constructed, the structure of which is shown in FIG. 3A.

Donor$_{HBEGY-sg1}$ comprises, from 5'-end to 3'-end: a 20-bp protective sequence, sg 1, a reverse termination codon, CMV promoter-driven puromycin-resistant gene, a forward termination codon, and a 20-bp protective sequence, respectively.

3. Transfection

HeLa cells were co-transfected with a Cas9-expressing plasmid, sgRNA1$_{HBEGF}$, and its corresponding donor Donor$_{HBEGF-sg1}$. As a control, HeLa cells were transfected with donor Donor$_{HBEGY-sg1}$ alone. Puromycin was added to the cells for resistance screening. A pooled population and single clones were obtained and stained with MTT. The results are shown in FIG. 3B.

Similar to the results of Example 1, only the donor plus sgRNA obtained a large number of puro+clones. This result again demonstrates that the donor insertion depends on specific sgRNA/Cas9-mediated DSBs.

4. Verification of Gene Knockout Efficiency

In addition, HeLa cells were co-transfected using a Cas9-expressing plasmid and sgRNA1$_{HBEGF}$, with or without its corresponding donor Donor$_{HBEGF-sg1}$. A pooled population and single clones were obtained by screening with puromycin (1 μg/ml). The plasmid expressing the puromycin-resistant gene is used for co-transfection insdead, when the corresponding donor is not added. As the HBEGF gene encodes a diphtheria toxin (DT) receptor, knocking this gene out in HeLa cells would result in resistance of the cells to DT [17], the pooled population and single clones obtained by puromycin screening were treated with DT (40 ng/ml) to compare the effect of the linear donor DNA on the HBEGF knockout efficiency. Images of different cells after being treated with DT are shown in FIG. 3C. The HBEGF knockout efficiency was determined by calculating the percentage of cells with DT resistance in the puro+pooled population, as shown in FIG. 3D. As can be seen from FIG. 3C and FIG. 3D, the use of the linear donor DNA greatly improves the HBEGF gene knockout efficiency compared with the use of sgRNA1$_{HBEGF}$ alone.

Figure 4A:
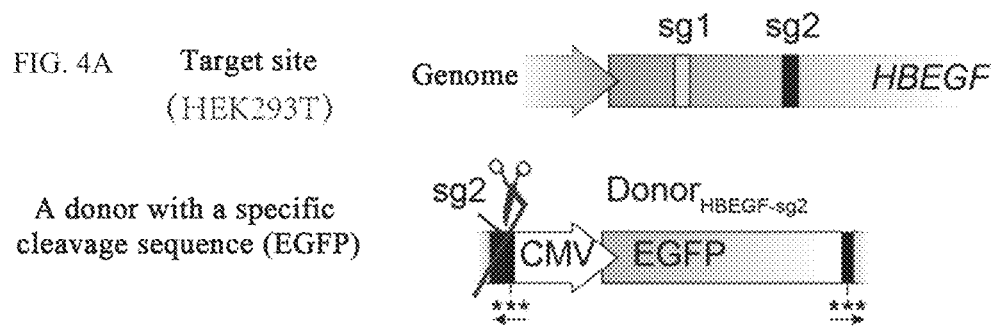
FIGS. 4A-4C show the donor design and experimental verification of enrichment of HBEGF disruption events in HEK293T cells by EGFP.

Example 3. Enrichment of HBEGF Gene Knockout Events in HEK293T Cells Using a Linear Donor DNA 1. Design of an sgRNA and construction of a linear donor DNA An sgRNA2$_{HBEGF}$ targeting the HBEGF gene in HEK293T cells was designed and a linear donor DNA (Donor$_{HBEGF-sg2}$) was constructed. The donor comprises, from 5'-end to 3'-end: a 20-bp protective sequence, sg2, a reverse termination codon, CMV promoter-driven EGFP gene, a forward termination codon, and a 20-bp protective sequence, respectively, as shown in FIG. 4A.

2. Verification of Gene Knockout Efficiency

Figure 4B:
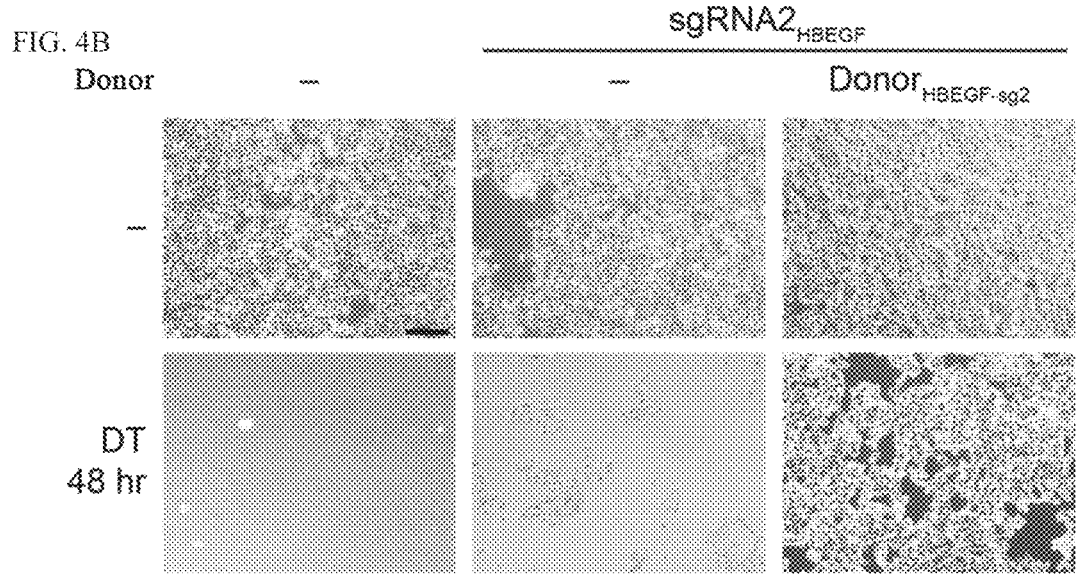
Figure 4C:
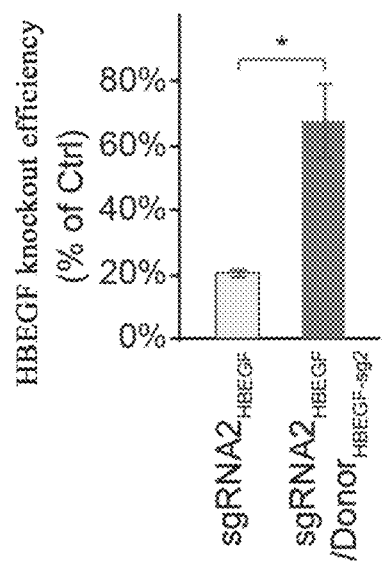

HEK293T cells were co-transfected using a Cas9-expressing plasmid and sgRNA2$_{HBEGF}$, with or without its corresponding donor Donor$_{HBEGF-sg2}$. Cells were screened by FACS. The group added the donor was screened for EGFP-positive cells by FACS, while the group didn't add the donor was screened for mCherry-positive cells by FACS. FACS-selected cells were treated with DT (40 ng/ml) to compare the effects of the linear donor DNAs on the HBEGF knockout efficiency. Images of different cells after being treated with DT are shown in FIG. 4B. The HBEGF knockout efficiency was determined by calculating the percentage of cells with DT resistance in the EGFP-positive cells, as shown in FIG. 4C. The use of the linear donor DNA greatly improves the HBEGF gene knockout efficiency compared with the use of sgRNA2$_{HBEGF}$ alone.

Example 4. Enrichment of ANTXR1 Gene Knockout Events in HeLa$_{oc}$ Cells Using Linear Donor DNAs 1. Establishment of HeLa$_{oc}$ cell line The HeLa$_{oc}$ cell line stably expressing Cas9 was established according to the existing method [17].

2. Design of sgRNAs and construction of linear donor DNAs

Two sgRNAs (sgRNA1$_{ANTXR1}$ and sgRNA2$_{ANTXR1}$) targeting the ANTXR1 gene in HeLa$_{oc}$ cells were designed, and three linear donor DNAs (Donor$_{ANTXR1-sg1}$, Donor$_{ANTXR1-sg2}$ and Donor$_{ANTXR1-pg}$) were constructed, as shown in FIG. 5A. The target sequence that sgRNA1$_{ANTXR1}$ targets is referred to as sg 1 in this example, and the target sequence that sgRNA2$_{ANTXR1}$ targets is referred to as sg2 in this example.

Donor$_{ANTXR1-sg1}$ comprises, from 5'-end to 3'- end: a 20-bp protective sequence, sg 1, a reverse termination codon, CMV promoter-driven puromycin-resistant gene, a forward termination codon, and a 20-bp protective sequence, respectively.

Donor$_{ANTXR1-sg2}$ comprises, from 5'-end to 3'-end: a 20-bp protective sequence, sg2, a reverse termination codon, CMV promoter-driven puromycin-resistant gene, a forward termination codon, and a 20-bp protective sequence, respectively.

Donor$_{ANTXR1-pg}$ comprises, from 5'-end to 3'-end: a 20-bp protective sequence, sg 1, a reverse termination codon, CMV promoter-driven puromycin-resistant gene, a forward termination codon, sg2, and a 20-bp protective sequence, respectively.

3. Transfection

HeLa$_{oc}$ cells were co-transfected with a Cas9-expressing plasmid, sgRNA1$_{ANTXR1}$ or sgRNA2$_{ANTXR1}$ or pgRNA$_{ANTXR1}$, and the corresponding donors. As a control, HeLa$_{oc}$ cells were transfected with linear donor DNAs (Donor$_{ANTXR1-SG1}$, Donor$_{ANTXR1-sg2}$, and Donor$_{ANTXR1-pg}$) alone. To the cells puromycin was added for resistance screening, and the cells were stained with MTT. The results are shown in FIG. 5B.

Similar to the results in HeLa cells, only the donors plus sgRNAs obtained a large number of puro+clones.

4. Verification of Gene Knockout Efficiency

In addition, HeLa$_{oc}$ cells were co-transfected using a Cas9-expressing plasmid and sgRNA1$_{ANTXR1}$ or sgRNA2$_{ANTXR1}$ or pgRNA$_{ANTXR1}$, with or without the corresponding donors, and screened with puromycin (1 μg/ml). The cells obtained by screening were treated with PA/LFnDTA. Images of different cells treated with PA/LFnDTA are shown in FIG. 5C. The ANTXR1 knockout efficiency was determined by calculating the percentage of cells with the toxin resistance in the puro+pooled population, as shown in FIG. 5D. The use of linear donor DNAs greatly improves the ANTXR1 gene knockout efficiency compared to the use of sgRNAs alone.

For puro+single clones, PCR verification was performed on the integration site of donor Donor$_{ANTXR1-sg1}$ in the ANTXR1 gene. It was found that most of the puro+clones contain donor inserts at the sgRNA-targeting sites (FIG. 5E and FIG. 5F), and most of the cells carrying donor fragments are real gene knockout clones (FIG. 5F).

A PCR fragment of about 500 bp (the length corresponding to the wild type ANTXR1 gene) and a PCR fragment of about 1.8 kb (the length corresponding to the wild type ANTXR1 gene plus a donor insert) were subjected to genome sequencing. The results are shown in Table 4.

TABLE 4

Genomic sequencing results of a PCR fragment of about 500 bp and a PCR fragment of about 1.8 kb Target site: ANTXR1 (Chr 2, Hela$_{oc}$)

| Category | Sequencing results of the PCR band (about 500 bp) of the same size as the wild type Wild type \| Mutant type \| Mutation rate | Sequencing results of the PCR band (about 1.8 kb) of the same size as the wild type after the donor insertion Wild type \| Mutant type \| Mutation rate |
|---|---|---|
| sgRNA$_1$ | 15 \| 0 \| 0% | — \| — \| — |
| sgRNA$_1$/Donor$_1$ | 1 \| 14 \| 93% | 15 \| 15 \| 100% |
| sgRNA2 | 13 \| 2 \| 15% | — \| — \| — |
| sgRNA$_2$/Donor$_2$ | 5 \| 10 \| 67% | 15 \| 15 \| 100% |
| pgRNA$_{1-2}$ | 10 \| 5 \| 33% | — \| — \| — |
| pgRNA$_{1-2}$/Donor$_{1-2}$ | 1 \| 14 \| 93% | 15 \| 15 \| 100% |

As can be seen from the PCR verification results (FIG. 5E) and sequencing results (Table 4), most clones contain only one donor insert. However, in donor-positive clones, the vast majority of alleles are edited (or mutated) at the target site, while sgRNAs alone are inefficient in producing insertion or deletion mutations (indels) without using a donor for enrichment. This finding clearly demonstrates that the donor insertion is closely related to the role of sgRNAs or pgRNAs.

5. Effect of a Donor on the Off-Target Effect of the CRISPR/Cas System

To examine whether the use of an external donor would affect the off-target effect of the CRISPR/Cas system, a whole genome integration site was found by splinkerette PCR analysis [35-37].

In this example, the off-target insertions in single clones and pooled clones were verified by splinkerette PCR analysis after puromycin selection. If a correct donor insertion in the ANTXR1 gene is present, amplification with primers Splink2/R1 and Splink2/R2 will result in 711- and 927-bp products, respectively (see FIG. 6A).

For splinkerette PCR analysis, we randomly selected 10 single clones with donor insertions and 3 puro+pooled clones targeting ANTXR1 in HeLa$_{oc}$ cells. Based on the splinkerette PCR results (FIG. 6B) which is similar to those clones that were not transfected with donors, that there is no detectable off-target effect in single clones or pooled population enriched by the donors.

Example 5. Enrichment of HBEGF Gene Knockout Events in HeLa$_{oc}$ Cells Using Linear Donor DNAs 1. Design of sgRNAs and construction of linear donor DNAs Two sgRNAs (sgRNA1$_{HBEGF}$ and sgRNA2$_{HBEGF}$) targeting the HBEGF gene in HeLa$_{oc}$ cells were designed, and three linear donor DNAs (Donor$_{HBEGF-sg1}$, Donor$_{HBEGF-sg2}$ and Donor$_{HBEGF-pg}$) were constructed, as shown in FIG. 7A. The target sequence that sgRNA1$_{HBEGF}$ targets is referred to as sg 1 in this example, and the target sequence that sgRNA2$_{HBEGF}$ targets is referred to as sg2 in this example.

Donor$_{HBEGF-sg1}$ comprises, from 5'-end to 3'-end: a 20-bp protective sequence, sg 1, a reverse termination codon, CMV promoter-driven puromycin-resistant gene, a forward termination codon, and a 20-bp protective sequence, respectively.

Donor$_{HBEGF-sg2}$ comprises, from 5'-end to 3'-end: a 20-bp protective sequence, sg2, a reverse termination codon, CMV promoter-driven puromycin-resistant gene, a forward termination codon, and a 20-bp protective sequence, respectively.

Donor$_{HBEGF-pg}$ comprises, from 5'-end to 3'-end: a 20-bp protective sequence, sg 1, a reverse termination codon, CMV promoter-driven puromycin-resistant gene, a forward termination codon, sg2, and a 20-bp protective sequence, respectively.

3. Transfection

HeLa$_{oc}$ cells were co-transfected with a Cas9-expressing plasmid, sgRNA1$_{HBEGF}$ or sgRNA2$_{HBEGF}$ or pgRNA$_{HBEGF}$, and the corresponding donors. As a control, HeLa$_{oc}$ cells were transfected with linear donor DNAs (Donor$_{HBEGF-sg1}$, Donor$_{HBEGF-sg2}$ and Donor$_{HBEGF-pg}$) alone. Puromycin was added to the cells for resistance screening. The results are shown in FIG. 7B.

Similar to the results in HeLa cells, only the donors plus sgRNAs obtained a large number of puro+clones.

4. Verification of Gene Knockout Efficiency

For puro+single clones, PCR verification was performed on the integration site of donor Donor$_{HBEGF-sg1}$ in the HBEGF gene. The L2/R2 primer sequences used in PCR amplification are shown in Table 5. It was found that most of the puro+clones contain donor inserts at the sgRNA-targeting sites (FIG. 7C and FIG. 7D), and most of the cells carrying donor fragments are real gene knockout clones (FIG. 7D).

TABLE 5

Primers for amplifying the linear donor-integrated HBEGF locus in HeLa$_{oc}$ cells

| Primer pair | Sequence |
|---|---|
| L2/R2 | 5'-GCCGCTTCGAAAGTGACTGG-3' (SEQ ID NO: 9) /5'-GATCCCCCAGTGCCCATCAG-3' (SEQ ID NO: 10) |

Example 6. Double Gene Knockout in HeLa$_{oc}$ Cells Using Linear Donor DNAs

1. Design of sgRNAs

Two target genes, PSEN1 and PSEN2, in HeLa$_{oc}$ cells were selected. Two sgRNAs targeting these two target genes respectively were designed, and their efficiency in producing indels at target sites was verified by T7E1 assay. The results are shown in Table 6. The target sequence that sgRNA$_{PSEN1}$ targets is referred to as sg$_{PSEN1}$ in this example, and the target sequence that sgRNA$_{PSEN2}$ targets is referred to as sg$_{PSEN2}$ in this example.

TABLE 6

The sgRNAs targeting PSEN1 and PSEN2 genes in HeLa$_{oc}$ cells

| sgRNA | Target sequence (5' to 3') | SEQ ID NO: | Mean Indels ± s.d. (%, n = 3) |
|---|---|---|---|
| sgRNA$_{PSEN1}$ | CCAGAATGCACAGATGTCTG(AGG) | 11 | 13.03 ± 3.04 |
| sgRNA$_{PSEN2}$ | TTCATGGCCTCTGACAGCG(AGG) | 12 | 13.67 ± 0.55 |

2. Construction of Linear Donor DNAs

Two types of donors were constructed. One type had two separate donors (Donor$_{PSEN1}$+Donor$_{PSEN2}$), and each donor had a corresponding sgRNA target sequence; and the other type of donor (Donor$_{PSEN}$) had two sgRNA-targeting sequences at both ends, respectively, as shown in FIG. 8A. Donor$_{PSEN1}$ or Donor$_{PSEN2}$ had a cleavage site for sgRNA$_{PSEN1}$ or sgRNA$_{PSEN2}$ at the 5'-end. Donor$_{PSEN}$ had a cleavage site for sgRNA$_{PSEN1}$ at the 5'-end and a cleavage site for sgRNA$_{PSEN2}$ at the 3'-end. Among the donors:

Donor$_{PSEN}$1 comprises, from 5'-end to 3'-end: a 20-bp protective sequence, sg$_{PSEN1}$, a reverse termination codon, CMV promoter-driven puromycin-resistant gene, a forward termination codon, and a 20-bp protective sequence, respectively.

Donor$_{PSEN}$2 comprises, from 5'-end to 3'-end: a 20-bp protective sequence, sg$_{PSEN2}$, a reverse termination codon, CMV promoter-driven puromycin-resistant gene, a forward termination codon, and a 20-bp protective sequence, respectively.

Donor$_{PSEN}$ comprises, from 5'-end to 3'-end: a 20-bp protective sequence, sg$_{PSEN1}$, a reverse termination codon, CMV promoter-driven puromycin-resistant gene, a forward termination codon, Sg$_{PSEN2}$, and a 20-bp protective sequence, respectively.

3. Verification of transfection and gene knockout efficiency

HeLa$_{oc}$ cells were co-transfected with a Cas9-expressing plasmid, sgRNA$_{PSEN1}$ or sgRNA$_{PSEN2}$; or HeLa$_{oc}$ cells were co-transfected with a Cas9-expressing plasmid and pgRNA$_{PSEN}$ to produce indels at specific sites of the PSEN1 and PSEN2 genes. T7E1 analysis was performed on the indels production efficiency [26] (see Table 7 for the primers used). The results are shown in FIG. 9A, and their co-transfections all show only ordinary activity.

HeLa$_{oc}$ cells were co-transfected with a Cas9-expressing plasmid, pgRNA$_{PSEN}$, and Donor$_{PSEN}$; or HeLa$_{oc}$ cells were co-transfected with a Cas9-expressing plasmid, pgRNA$_{PSEN}$, and Donor$_{PSEN1}$+Donor$_{PSEN2}$. To the cells puromycin was added for resistance screening to obtain puro+clones (see FIG. 9B). Similar to the results of the previous examples, the donors plus pgRNAs obtained a large number of puro+clones.

For each transfection result, puro+single clones were subjected to PCR verification of the integration sites of donors Donor$_{PSEN}$ and Donor$_{PSEN1}$+Donor$_{PSEN2}$ in the PSEN1 and PSEN2 genes. The primers used in the PCR amplification are shown in Table 7, wherein L3/R3 were used to amplify the integration site in PSEN1, and L4/R4 were used to amplify the integration site in PSEN2. The PCR verification results are shown in FIG. 9C. Clones containing donor insertions in both genes are indicated by boxes. Clone 1 and clone 2 were selected for further genome sequencing analysis, and both clones showed disruption of PSEN1 and PSEN2 (FIG. 8B and FIG. 8C).

TABLE 7

Primers for amplifying the linear donor-integrated PSEN1 and PSEN2 sites in HeLa$_{OC}$ cells

| Primer pair | Sequence |
| --- | --- |
| L3/R3 | 5'-TGGTGTCTCAGGCGGTTCTA-3' (SEQ ID NO: 13) /5'-TGAACTATGAGGCGCTGCAC-3' (SEQ ID NO: 14) |
| L4/R4 | 5'-TGACTTTCGTGGCTATGCGT-3' (SEQ ID NO: 15) /5'-CTAGCACCCAGGCATCCAAA-3' (SEQ ID NO: 16) |

Example 7. Multi-Gene Knockout in HeLa$_{oc}$ Cells Using a Linear Donor DNA

1. Selection of Target Genes and Design of an sgRNA

The HSPA gene family in HeLa$_{oc}$ cells was selected, which includes five homologous genes, HSAPA1A, HSPA1B, HSBA1L, HSPA6 and HSPA2. The sgRNA$_{HSPA}$ simultaneously targeting HSAPA1A, HSPA1B and HSBA1L was designed. The target sequence that the sgRNA targets has a mismatch with the corresponding sequence in HSPA6 and two mismatches with HSPA2. These are shown in FIG. 8D.

2. Construction of Linear Donor DNAs

A linear donor Donor$_{HSPA}$ was constructed, comprising, from 5'-end to 3'-end: a 20-bp protective sequence, sg$_{HSPA}$, a reverse termination codon, CMV promoter-driven puromycin-resistant gene, a forward termination codon, and a 20-bp protective sequence, respectively (FIG. 8D).

3. Verification of Transfection and Gene Knockout Efficiency

HeLa$_{oc}$ cells were co-transfected using a Cas9-expressing plasmid and sgRNA$_{HSPA}$, with or without its corresponding donor Donor$_{HSPA}$, indels were triggered, and resistance screening was performed by puromycin. The group without the donor added was co-transfected with a plasmid expressing a puromycin-resistant gene instead. The indels efficiency for all five genes was evaluated by T7E1 assay (see Table 8 for the primers used). The results are shown in FIG. 8E. Compared with sgRNA$_{HSPA}$ alone, the use of donor HSPA increased the mutation rate at the HSPA1A site by approximately 5.5 times, increased the mutation rate at the HSPA1B site by approximately 6.1 times, increased the mutation rate at the HSPA1L site by approximately 3.4 times, and increased the mutation rate at the HSPA6 site by approximately 6.6 times. Interestingly, no indels was detected in the HSPA2 gene, regardless of whether the donor was used, indicating that the two mismatches completely disrupt the recognition by sgRNA$_{HSPA}$. Furthermore, and more importantly, selection using a donor did not increase the risk of off-target effects.

Figure 10:
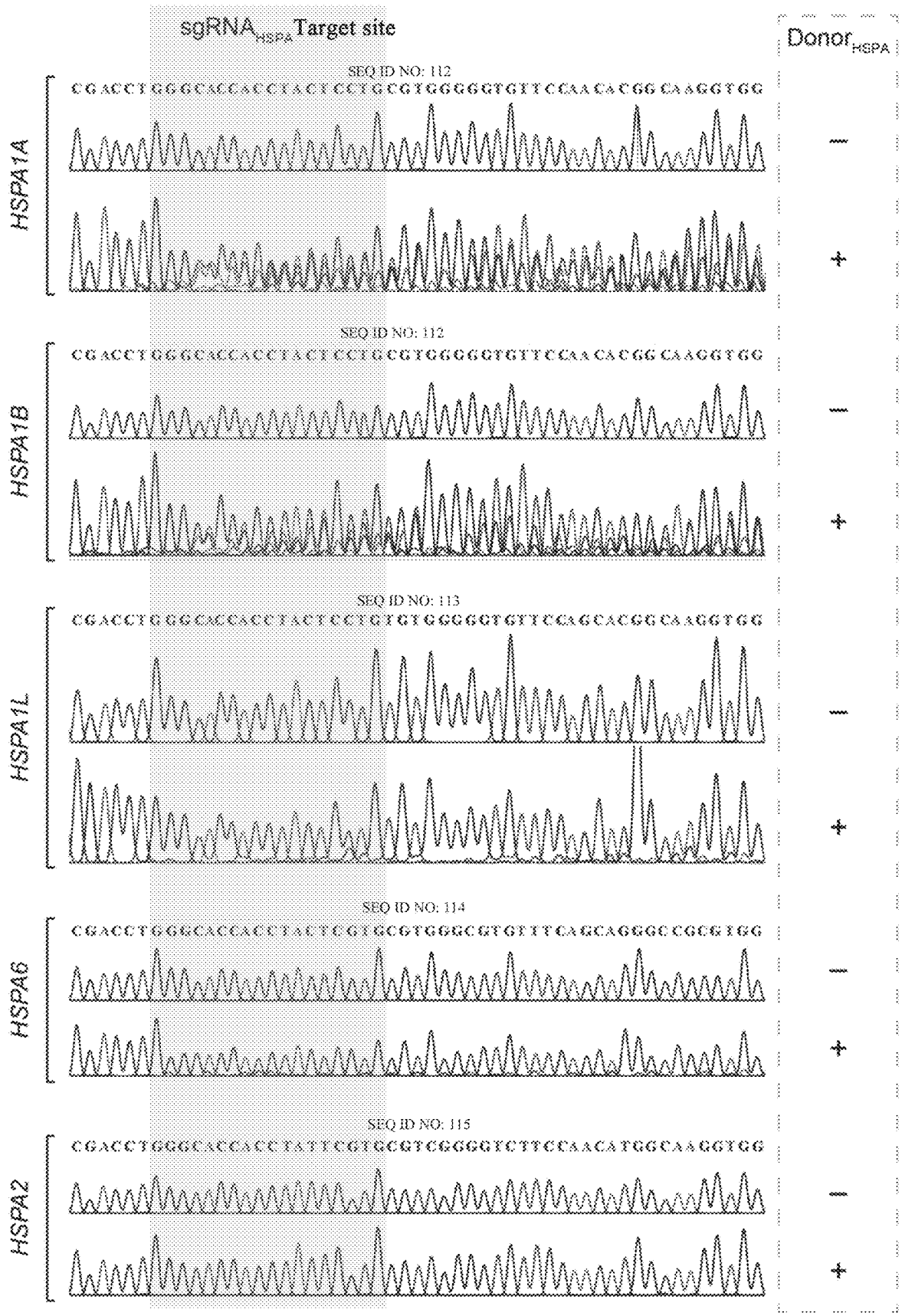
FIG. 10 shows the sequencing chromatogram of target regions of the HSPA family genes in pooled cells transfected with or without a donor. The sgRNA-targeting sites are shaded, and target regions containing donor insertions are not included in these sequencing analyses.

The target regions of HSPA family genes in pooled population co-transfected with and without the donor were sequenced. The results are shown in FIG. 10. The results showed that the cell pool sequencing results are consistent with the results of T7E1 assay, regardless of whether there is donor transfection at the HSPA family gene loci.

Notably, the T7E1 assay demonstrates that the selected pooled clones are highly rich in cells carrying target mutations, and the enrichment factor is approximately 753 (5.5*6.1*3.4*6.6) compared with traditional methods without using a donor. Considering that this calculation does not consider genes with donor insertions, the actual efficiency is even higher.

Figures 11A, 11B:
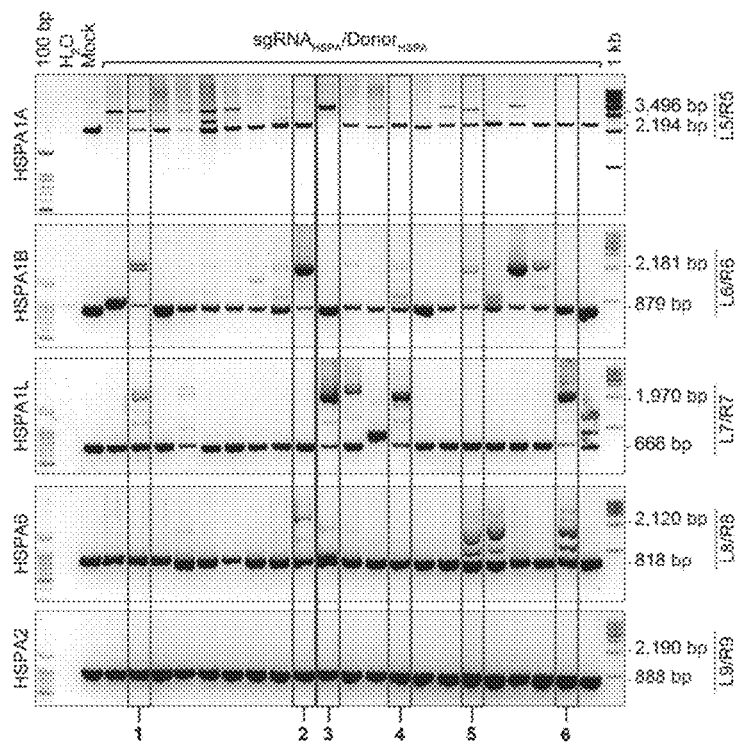
FIGS. 11A-11B show identification of single clones with inserted donor at target sites of five HSPA family genes, HSPA1A, HSPA1B, HSPA1L, HSPA6 and HSPA2.

For puromycin-resistant single clones, PCR verification was performed at five target sites. Specific primers (L5/R5, L6/R6, L7/R7, L8/R8, and L9/R9) used to amplify target sites of all five genes are listed in Table 8. The results are shown in FIG. 11A and FIG. 11B. Genomic sequence analysis was performed on six selected clones (identified by boxes in the figure and numbered 1-6, respectively) with donor insertions in at least two target genes. The results are shown in FIG. 11B. Clone 3 has modifications at the corresponding sites of the four genes: frameshift mutations in HSPA1A, HSPA1B and HSPA1L resulting in complete knockouts, as well as two in-frame mutations in HSPA6 (FIG. 8F).

TABLE 8

Primers for amplifying five gene target sites of the HSPA family in HeLa$_{OC}$ cells

| Primer pair | Sequence |
| --- | --- |
| L5/R5 | 5'-GAGAGTGACTCCCGTTGTCC-3' (SEQ ID NO: 17) /5'-ACATTGCAAACACAGGAAATTGAG-3' (SEQ ID NO: 18) |
| L6/R6 | 5'-GTGTTGAGTTTCCGGCGTTC-3' (SEQ ID NO: 19) /5'-TCGCTTGTTCTGGCTGATGT-3' (SEQ ID NO: 20) |
| L7/R7 | 5'-GCACTCTCCCAAAACAGTATCTTA-3' (SEQ ID NO: 21) /5'-GTGCCTCCACCCAGATCAAA-3' (SEQ ID NO: 22) |
| L8/R8 | 5'-GGGTGAGGCGCAAAAGGATA-3' (SEQ ID NO: 23) /5'-ACACCAGCGTCAATGGAGAG-3' (SEQ ID NO: 24) |

Example 8. Enrichment of CSPG4 Gene Knockout Events in SC-8 Cells Using Linear Donor DNAs Containing Universal sgRNAs 1. Screening of universal sgRNAs The following 10 sgRNAs were selected as candidate sequences for screening, as shown in the following table:

| sgRNA | Target Sequence (PAM) (5' to 3') | Predicted gene knockout efficiency |
| --- | --- | --- |
| sgRNA$_{Universal\_1}$ | GTACGGGGCGATCATCCACACGG (SEQ ID NO: 25) | 0.982784325 |

| sgRNA | Target Sequence (PAM) (5' to 3') | Predicted gene knockout efficiency |
|---|---|---|
| sgRNA$_{Universal\_2}$ | GCAAAAGTGGCATAAAACCGCGG (SEQ ID NO: 26) | 0.971302462 |
| sgRNA$_{Universal\_3}$ | TATCGCTTCCGATTAGTCCGCGG (SEQ ID NO: 27) | 0.96832667 |
| sgRNA$_{Universal\_4}$ | CTATCTCGAGTGGTAATGCGCGG (SEQ ID NO: 28) | 0.966411034 |
| sgRNA$_{Universal\_5}$ | GTAGCTGCTGTAAATCGCATCGG (SEQ ID NO: 29) | 0.963330804 |
| sgRNA$_{Universal\_6}$ | TATACCAGACCACAGCGCCGCGG (SEQ ID NO: 30) | 0.963267571 |
| sgRNA$_{Universal\_7}$ | GCACGAGGTGAACAGCCGCTCGG (SEQ ID NO: 31) | 0.960224565 |
| sgRNA$_{Universal\_8}$ | ATGATATCTGACATGCAGCGCGG (SEQ ID NO: 32) | 0.95578653 |
| sgRNA$_{Universal\_9}$ | AATCGACTCGAACTTCGTGTCGG (SEQ ID NO: 33) | 0.950640031 |
| sgRNA$_{Universal\_10}$ | CGAATCGGAACTTTGTACCGCGG (SEQ ID NO: 34) | 0.948431616 |

2. Construction of Linear Donor DNAs 10 linear donor DNAs (Donor$_{sSGRMA\_Imoversa;\_1\sim10\ puro}$) were constructed based on the above-mentioned 10 universal sgRNAs, respectively.

These linear donor DNAs comprise, from 5'-end to 3'-end: a 20-bp protective sequence, a target sequence that sgRNA$_{Universal\_1\sim10}$ targets, a reverse termination codon, CMV promoter-driven puromycin-resistant gene, a forward termination codon, and a 20-bp protective sequence, respectively.

Figure 12:
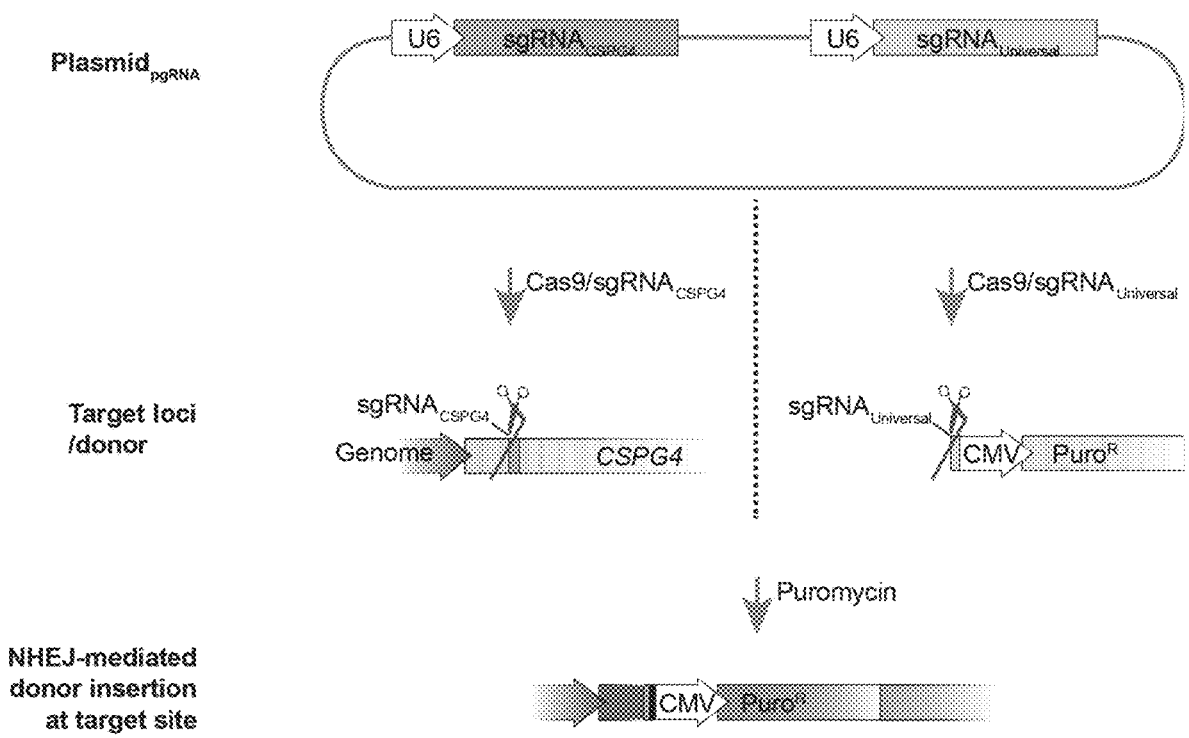
FIG. 12 shows an experimental flow chart of gene knockout using a donor comprising a universal sgRNA.

3. Construction of Tandem sgRNA Plasmids 10 tandem sgRNA plasmids (Plasmid$_{pgRNA\_Universal\_1\sim10}$) were constructed based on the above-mentioned 10 linear donors, respectively, the structures of which are shown in FIG. 12.

Two tandem sgRNAs were sgRNA$_{CSPG4}$ and sgRNA$_{Universal\_1\sim10}$, respectively. Among these sgRNAs, sgRNA$_{CSPG4}$ targets CSPG4, the receptor of TcdB toxin, while sgRNA$_{Universal\_1\sim10}$ targets the target sequence in the corresponding donor DNA (Donor$_{sgRNA\_Universal\_1\sim10puro}$)

4. Transfection

The cell line used in the transfection experiment was a cell line stably expressing Cas9 (SC-8). SC-8 cells were co-transfected with ten tandem plasmids Plasmid$_{pgRNA\_Universal\_1\sim10}$ and the corresponding donor DNAs (Donors$_{sgRNA\_Universal\_1\sim10puro}$). As a control, SC-8 cells were co-transfected with ten linear donor DNAs (Donors$_{sgRNA\_Universal\_1\sim10puro}$) alone. Puromycin was added to the cells for resistance screening. A pooled population was obtained. The screening results are shown in the following table.

| Experimental condition | Viable colonies (resistant to puromycin) |
|---|---|
| Dnonr$_{sgRNA\_Universal\_1-puro}$ | 0 |
| Plasmid$_{pgRNA}$/Dnonr$_{sgRNA\_Universal\_1-puro}$ | 47 |
| Dnonr$_{sgRNA\_Universal\_2-puro}$ | 3 |
| Plasmid$_{pgRNA}$/Dnonr$_{sgRNA\_Universal\_2-puro}$ | 23 |
| Dnonr$_{sgRNA\_Universal\_3-puro}$ | 14 |
| Plasmid$_{pgRNA}$/Dnonr$_{sgRNA\_Universal\_3-puro}$ | 60 |
| Dnonr$_{sgRNA\_Universal\_4-puro}$ | 7 |
| Plasmid$_{pgRNA}$/Dnonr$_{sgRNA\_Universal\_4-puro}$ | 8 |
| Dnonr$_{sgRNA\_Universal\_5-puro}$ | 7 |
| Plasmid$_{pgRNA}$/Dnonr$_{sgRNA\_Universal\_5-puro}$ | 29 |
| Dnonr$_{sgRNA\_Universal\_6-puro}$ | 7 |
| Plasmid$_{pgRNA}$/Dnonr$_{sgRNA\_Universal\_6-puro}$ | 42 |
| Dnonr$_{sgRNA\_Universal\_7-puro}$ | 0 |
| Plasmid$_{pgRNA}$/Dnonr$_{sgRNA\_Universal\_7-puro}$ | 18 |
| Dnonr$_{sgRNA\_Universal\_8-puro}$ | 0 |
| Plasmid$_{pgRNA}$/Dnonr$_{sgRNA\_Universal\_8-puro}$ | 17 |
| Dnonr$_{sgRNA\_Universal\_9-puro}$ | 0 |
| Plasmid$_{pgRNA}$/Dnonr$_{sgRNA\_Universal\_9-puro}$ | 74 |
| Dnonr$_{sgRNA\_Universal\_10-puro}$ | 0 |
| Plasmid$_{pgRNA}$/Dnonr$_{sgRNA\_Universal\_10-puro}$ | 19 |

According to the above-mentioned results, four sgRNAs, i.e., sgRNA$_{Universal\_1}$, sgRNA$_{Universal\_3}$, sgRNA$_{Universal\_6}$ and sgRNA$_{Universal\_9}$, had better effects. Therefore, in subsequent experiments, pooled clones corresponding to these four sgRNAs were used as the experimental objects.

4. Verification of Gene Knockout Efficiency

Figure 13:
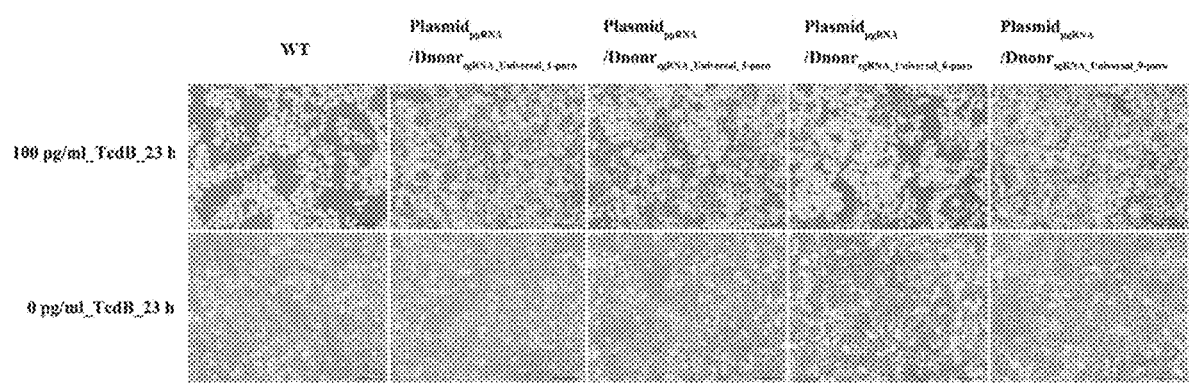
FIG. 13 shows the efficiency verification of gene knockout using a donor comprising a universal sgRNA.

TcdB toxin was added to the four pooled clones for screening, and the cell survival was observed after 23 hours. The experimental results are shown in FIG. 13. It can be seen that 23 hours after the addition of TcdB toxin, the cell survival rates corresponding to the experimental groups with sgRNA$_{Universal\_1}$ and sgRNA$_{Universal\_9}$ added were significantly higher than those of the other two groups, indicating that sgRNA$_{Universal\_1}$ and sgRNA$_{Universal\_9}$ achieve higher gene knockout efficiency.

The materials and methods used in Examples 1-7 above were as follows:

Cell Culture and Transfection

HeLa, HeLa$_{oc}$ and HEK293T cells were maintained in a Dulbecco's modified Eagle's medium (DMEM, 10-013-CV, Corning, Tewksbury, MA, USA) supplemented with 10% fetal bovine serum (FBS, Lanzhou Bailing Biotechnology Co., Ltd., Lanzhou, China) at a temperature of 37° C., and supplied with 5% CO2. For transfection, all cells were seeded on a 6-well plate and transfected with X-tremeGENE HP (06366546001, Roche, Mannheim, Germany) according to the supplier's instructions. Briefly, 2 μg of DNA and 4 μl of X-tremeGENE HP were added to 200 μl of Opti-MEM I Reduced Serum Medium (31985088, Thermo Fisher Scientific, Grand Island, N.Y., USA). The mixture was incubated for 15 minutes at room temperature and then added to the cells.

Cloning of a Plasmid Expressing a gRNA

For plasmids expressing sgRNAs, the oligonucleotide of each sgRNA coding sequence was designed separately (see Table 9) and synthesized (Beijing Ruibo Xingke Biotechnology Co., Ltd.).

two gRNA coding sequences (Table 5), and the PCR product was then purified and ligated into the sgRNA backbone vector using the "Golden Gate" method. Compared with the previously reported sgRNA backbone vector [17], the sgRNA backbone vector of the present invention has modifications in the sgRNA backbone [38], and has the EGFP sequence replaced with the mCherry coding sequence.

T7E1 Assay

Genomic DNAs were extracted using a DNeasy Blood & Tissue kit (69504, Qiagen, Hilden, Germany), and the genomic region comprising the gRNA target sequence was subjected to PCR amplification. The primer sequences used in the assay are shown in Table 2, Table 5, Table 7, and Table 8. 300-500 ng of PCR product obtained using these primer sequences was mixed with 10× NEB Buffer2 in a 50 μl of system, heated at 95° C. for 3 minutes, and slowly cooled to room temperature. The resulting product was incubated with 0.5 μl of T7E1 for 15 min at 37° C. for agarose gel electrophoresis. The electropherogram was analyzed by Image J image analysis software for the band cleavage efficiency which indicates the efficiency of generating Indels by sgRNAs.

TABLE 9

Primers for construction of an sgRNA or a pgRNA

| sgRNA | Forward primer | Reverse primer |
| --- | --- | --- |
| sgRNA1$_{ANTXR1}$ | 5'-ACCGAGCGGAGAGCCCTCGGCAT-3' (SEQ ID NO: 35) | 5'-AAACATGCCGAGGGCTCTCCGCT-3' (SEQ ID NO: 36) |
| sgRNA2$_{ANTXR1}$ | 5'-ACCGTGCTCATCTGCGCCGGGCAA-3' (SEQ ID NO: 37) | 5'-AAACTTGCCCGGCGCAGATGAGCA-3' (SEQ ID NO: 38) |
| pgRNA$_{ANTXR1}$ | 5'-TATACGTCTCAACCGAGCGGAGAGCCCTC GGCATGTTTAAGAGCTATGCTGGAAACAG-3' (SEQ ID NO: 39) | 5'-TATACGTCTCAAAACTTGCCCGGCGCAG ATGAGCACGGTGTTTCGTCCTTTTCCACA-3' (SEQ ID NO: 40) |
| sgRNA1$_{HBEGF}$ | 5'-ACCGGACTGGCGAGAGCCTGGAG-3' (SEQ ID NO: 41) | 5'-AAACCTCCAGGCTCTCGCCAGTC-3' (SEQ ID NO: 42) |
| sgRNA2$_{HBEGF}$ | 5'-ACCGCGGACCAGCTGCTACCCCT-3' (SEQ ID NO: 43) | 5'-AAACAGGGGTAGCAGCTGGTCCG-3' (SEQ ID NO: 44) |
| pgRNA$_{HBEGF}$ | 5'-TATACGTCTCAACCGGACTGGCGAGAGCC TGGAGGTTTAAGAGCTATGCTGGAAACAG-3' (SEQ ID NO: 45) | 5'-TATACGTCTCAAAACAGGGGTAGCAGCT GGTCCGCGGTGTTTCGTCCTTTTCCACA-3' (SEQ ID NO: 46) |
| sgRNA$_{PSEN1}$ | 5'-ACCGCCAGAATGCACAGATGTCTG-3' (SEQ ID NO: 47) | 5'-AAACCAGACATCTGTGCATTCTGG-3' (SEQ ID NO: 48) |
| sgRNA$_{PSEN2}$ | 5'-ACCGTTCATGGCCTCTGACAGCG-3' (SEQ ID NO: 49) | 5'-AAACCGCTGTCAGAGGCCATGAA-3' (SEQ ID NO: 50) |
| pgRNA$_{PSEN}$ | 5'-TATACGTCTCaACCGCCAGAATGCACAGA TGTCTGGTTTAAGAGCTATGCTGGAAACA-3' (SEQ ID NO: 51) | 5'-TATACGTCTCaAAACCGCTGTCAGAGGC CATGAACGGTGTTTCGTCCTTTTCCACA-3' (SEQ ID NO: 52) |
| sgRNA$_{HSPA}$ | 5'-ACCGCAGGAGTAGGTGGTGCCC-3' (SEQ ID NO: 53) | 5'-AAACGGGCACCACCTACTCCTG-3' (SEQ ID NO: 54) |

Oligonucleotides were dissolved to a concentration of 10 μM in 1×TE, and the paired oligonucleotides were mixed with TransTaq HiFi Buffer II (K10222, Beijing TransGen Biotech Co., Ltd.), heated to 95° C. for 3 minutes, and then slowly cooled to 4° C. These annealed oligonucleotide pairs were phosphorylated for 30 minutes at 37° C. After heat inactivation, the product was ligated into the sgRNA backbone vector using the "Golden Gate" method. For plasmids expressing pgRNAs, the scaffold sequence of the gRNA and the U6 promoter were amplified with primers comprising Construction of a Linear Donor A donor sequence comprising a CMV-driven puromycin-resistant gene or EGFP gene, and termination codon sequences were pre-produced, and cloned into the pEASY-T5-Zero clone vector (CT501-02, Beijing TransGen Biotech Co., Ltd.) as a universal template. The template was amplified using primers comprising sgRNA cleavage target sites and protective sequences. The primer sequences are shown in Table 10.

TABLE 10

Primers for construction of a linear donor

| Donor | Primer (forward/reverse) Step 1 | Step 2 |
|---|---|---|
| Donor$_{ANTXR1-sg1}$ | 5'-AGAGCCCTCGGCATCGGCTTCCAGTGGCTCTCTTTGGTTAGTCACCTACTAGTTAGTCA-3' (SEQ ID NO: 55) /5'-GGCTTAGGATTGTTACGCCCTCACTTATCTACTAATCAATTA-3' (SEQ ID NO: 56) | 5'-TCCACTGCGACGTCGCGAGTAGCGGAGAGCCCTCGGCATCGGCTTCCAGTGGCTCTC-3' (SEQ ID NO: 57) /5'-GGCTTAGGATTGTTACGCCCTCACTTATCTACTAATCAATTA-3' (SEQ ID NO: 56) |
| Donor$_{ANTXR1-sg2}$ | 5'-TCTGCGCCGGGCAAGGGGGACGCAGGGAGGATGGGGGTTAGTCACCTACTAGTTAGTCA-3' (SEQ ID NO: 58) /5'-GGCTTAGGATTGTTACGCCCTCACTTATCTACTAATCAATTA-3' (SEQ ID NO: 56) | 5'-TCCACTGCGACGTCGCGAGTTGCTCATCTGCGCCGGGCAAGGGGGACGCAGGGCAGGAT-3' (SEQ ID NO: 59) /5'-GGCTTAGGATTGTTACGCCCTCACTTATCTACTAATCAATTA-3' (SEQ ID NO: 56) |
| Donor$_{ANTRXR1-pgRNA}$ | 5'-AGAGCCCTCGGCATCGGCTTCCAGTGGCTCTCTTTGGTTAGTCACCTACTAGTTAGTCA-3' (SEQ ID NO: 55) /5'-CCCGGCGCAGATGAGCACCAGAGTGGCCAAAGAGAGCTCACTTATCTACTAATCAATTA-3' (SEQ ID NO: 60) | 5'-TCCACTGCGACGTCGCGAGTAGCGGAGAGCCCTCGGCATCGGCTTCCAGTGGCTCTC-3' (SEQ ID NO: 57) /5'-GGCTTAGGATTGTTACGCCCCCCTTGCCCGGCGCAGATGAGCACCAGAGTGG-3' (SEQ ID NO: 61) |
| Donor$_{HBEGF-sg1}$ | 5'-GCGAGAGCCTGGAGCGGCTTCGGAGAGGGCTAGCTGCTTAGTCACCTACTAGTTAGTCA-3' (SEQ ID NO: 62) /5'-GGCTTAGGATTGTTACGCCCTCACTTATCTACTAATCAATTA-3' (SEQ ID NO: 56) | 5'-TCCACTGCGACGTCGCGAGTGACTGGCGAGAGCCTGGAGCGGCTTCGGAGAGGGCT-3' (SEQ ID NO: 63) /5'-GGCTTAGGATTGTTACGCCCTCACTTATCTACTAATCAATTA-3' (SEQ ID NO: 56) |
| Donor$_{HBEGF-sg2}$ | 5'-AGCTGCTACCCCTAGGAGGCGGCCGGGACCGGAAAGTTAGTCACCTACTAGTTAGTCA-3' (SEQ ID NO: 64) /5'-GGCTTAGGATTGTTACGCCCTCACTTATCTACTAATCAATTA-3' (SEQ ID NO: 56) | 5'-TCCACTGCGACGTCGCGAGTCGGACCAGCTGCTACCCCTAGGAGGCGGCCGGGACCGGA-3' (SEQ ID NO: 65) /5'-GGCTTAGGATTGTTACGGGCCACTTATCTACTAATCAATTA-3' (SEQ ID NO: 56) |
| Donor$_{HBGEF-pgRNA}$ | 5'-GCGAGAGCCTGGAGCGGCTTCGGAGAGGGCTAGCTGCTTAGTCACCTACTAGTTAGTCA-3' (SEQ ID NO: 62) /5'-GGGTAGCAGCTGGTCCGTGGATACAGTGGGAGGGTCCTCACTTATCTACTAATCAATTA-3' (SEQ ID NO: 66) | 5'-TCCACTGCGACGTCGCGAGTGACTGGCGAGAGCCTGGAGCGGCTTCGGAGAGGGCT-3' (SEQ ID NO: 63) /5'-GGCTTAGGATTGTTACGCCCCCTAGGGGTAGCAGCTGGTCCGTGGATACAGTGGGA-3' (SEQ ID NO: 67) |
| Donor$_{PSEN1}$ | 5'-GATGTCTGAGGACAACCACCTGAGCAATACTTTAGTCACCTACTAGTTAGTCA-3' (SEQ ID NO: 68) /5'-GGCTTAGGATTGTTACGCCCTCACTTATCTACTAATCAATTA-3' (SEQ ID NO: 56) | 5'-TCCACTGCGACGTCGCGAGTCCAGAATGCACAGATGTCTGAGGACAACCACCTG-3' (SEQ ID NO: 69) /5'-GGCTTAGGATTGTTACGCCCTCACTTATCTACTAATCAATTA-3' (SEQ ID NO: 56) |
| Donor$_{PSEN2}$ | 5'-CTGACAGCGAGGAAGAAGTGTGTGATGAGCGGTTAGTCACCTACTAGTTAGTCA-3' (SEQ ID NO: 70) /5'-GGCTTAGGATTGTTACGCCCTCACTTATCTACTAATCAATTA-3' (SEQ ID NO: 56) | 5'-TCCACTGCGACGTCGCGAGTTTCATGGCCTCTGACAGCGAGGAAGAAGTG-3' (SEQ ID NO: 71) /5'-GGCTTAGGATTGTTACGCCCTCACTTATCTACTAATCAATTA-3' (SEQ ID NO: 56) |
| Donor$_{PSEN1+PSEN2}$ | 5'-GATGTCTGAGGACAACCACCTGAGCAATACTTTAGTCACCTACTAGTTAGTCA-3' (SEQ ID NO: 68) /5'-GGCTTAGGATTGTTACGCCCCCTCGCTGTCAGAGGCCATGAATGTGAGCATAGC-3' (SEQ ID NO: 72) | 5'-TCCACTGCGACGTCGCGAGTCCAGAATGCACAGATGTCTGAGGACAACCACCTG-3' (SEQ ID NO: 69) /5'-GCCATGAATGTGAGCATAGCCCTGCCTCTCACTTATCTACTAATCAATTA-3' (SEQ ID NO: 73) |
| Donor$_{HSPA}$ | 5'-ACCACCTACTCCTGCGTGGGGGTGTTCCAACACGTTAGTCACCTACTAGTTAGTCA-3' (SEQ ID NO: 74) /5'-GGCTTAGGATTGTTACGCCCTCACTTATCTACTAATCAATTA-3' (SEQ ID NO: 56) | 5'-TCCACTGCGACGTCGCGAGTCCTGGGCACCACCTACTCCTGCGTGGGGGTGTTC-3' (SEQ ID NO: 75) /5'-GGCTTAGGATTGTTACGCCCTCACTTATCTACTAATCAATTA-3' (SEQ ID NO: 56) |

NHEJ-Based Donor Insertion and Cell Selection

HeLa$_{oc}$ cells were transfected with 1 µg of purified linear donor PCR product and 1 µg of sgRNA/pgRNA, and treated with 1 µg/ml puromycin two weeks after transfection. HeLa and HEK293T cells were transfected with 1 µg of a donor, 0.5 µg of sgRNA/pgRNA and 0.5 µg of Cas9 plasmid. The cells were then treated with 1 µg/ml puromycin two weeks after transfection, or determined to be EGFP positive by the fluorescence activated cell sorting (FACS), depending on which type of donor was used.

Splinkerette PCR

The splinkerette PCR method has been previously reported (Potter, C. J. & Luo, L. Splinkerette PCR for mapping transposable elements in *Drosophila*. PLoS One 5, e10168 (2010); Uren, A. G. et al. A high-throughput splinkerette-PCR method for the isolation and sequencing of retroviral insertion sites. Nat Protoc 4, 789-798 (2009); and Yin, B. & Largaespada, D.A. PCR-based procedures to isolate insertion sites of DNA elements. *Biotechniques* 43, 79-84 (2007)). The primer and adaptor sequences used are shown in Table 11.

TABLE 11

Primers for Splinkerette PCR

| Primer | Sequence |
| --- | --- |
| Long-strand adaptor | 5'-CGAAGAGTAACCGTTGCTAGGAGAGACCGTGGC TGAATGAGACTGGTGTCGACACTAGTGG-3' (SEQ ID NO: 76) |
| Short-strand adaptor | 5'-CGCGCCACTAGTGTCGACACCAGTCTCTAATTT TTTTTTCAAAAAAA (SEQ ID NO: 77) |
| Splink1 | 5'-CGAAGAGTAACCGTTGCTAGGAGAGACC-3' (SEQ ID NO: 78) |
| Splink2 | 5'-GTGGCTGAATGAGACTGGTGTCGAC-3' (SEQ ID NO: 79) |
| R1 | 5'-GCAACCTCCCCTTCTACGAGCGGC-3' (SEQ ID NO: 80) |
| R2 | 5'-GCATGGCCGTGTTGAGCGGTTCCC-3' (SEQ ID NO: 81) |

REFERENCES

1. Kim, Y. G., Cha, J. & Chandrasegaran, S. Hybrid restriction enzymes: zinc finger fusions to Fok I cleavage domain. Proc Natl Acad Sci USA 93, 1156-1160 (1996).
2. Boch, J. et al. Breaking the code of DNA binding specificity of TAL-type III effectors. Science 326, 1509-1512 (2009).
3. Moscou, M. J. & Bogdanove, A. J. A simple cipher governs DNA recognition by TAL effectors. Science 326, 1501 (2009).
4. Miller, J. C. et al. A TALE nuclease architecture for efficient genome editing. Nat Biotechnol 29, 143-148 (2011).
5. Jinek, M. et al. A programmable dual-RNA-guided DNA endonuclease in adaptive bacterial immunity. Science 337, 816-821 (2012).
6. Mali, P. et al. RNA-guided human genome engineering via Cas9. Science 339, 823-826 (2013).
7. Cong, L. et al. Multiplex Genome Engineering Using CRISPR/Cas Systems. Science 339, 819-823 (2013).
8. Phillips, E. R. & McKinnon, P. J. DNA double-strand break repair and development. Oncogene 26, 7799-7808 (2007).
9. Chapman, J. R., Taylor, M. R. & Boulton, S. J. Playing the end game: DNA double-strand break repair pathway choice. Mol Cell 47, 497-510 (2012).
10. Gilbert, L. A. et al. CRISPR-mediated modular RNA-guided regulation of transcription in eukaryotes. Cell 154, 442-451 (2013).
11. Ma, H. et al. Multicolor CRISPR labeling of chromosomal loci in human cells. Proc Natl Acad Sci USA 112, 3002-3007 (2015).
12. Chen, B. et al. Dynamic imaging of genomic loci in living human cells by an optimized CRISPR/Cas system. Cell 155, 1479-1491 (2013).
13. Li, H.L., Gee, P., Ishida, K. & Hotta, A. Efficient genomic correction methods in human iPS cells using CRISPR-Cas9 system. Methods (2015).
14. Savic, N. & Schwank, G. Advances in therapeutic CRISPR/Cas9 genome editing. Translational research: the journal of laboratory and clinical medicine 168, 15-21 (2016).
15. Miyaoka, Y. et al. Isolation of single-base genome-edited human iPS cells without antibiotic selection. Nat Methods 11, 291-293 (2014).
16. Fu, Y. et al. High-frequency off-target mutagenesis induced by CRISPR-Cas nucleases in human cells. Nat Biotechnol 31, 822-826 (2013).
17. Zhou, Y. et al. High-throughput screening of a CRISPR/Cas9 library for functional genomics in human cells. Nature 509, 487-491 (2014).
18. Yu, C. et al. Small Molecules Enhance CRISPR Genome Editing in Pluripotent Stem Cells. Cell Stem Cell 16, 142-147 (2015).
19. Liao, S., Tammaro, M. & Yan, H. Enriching CRISPR-Cas9 targeted cells by co-targeting the HPRT gene. Nucleic Acids Res 43, e134 (2015).
20. Kim, H. et al. Surrogate reporters for enrichment of cells with nuclease-induced mutations. Nat Methods 8, 941-943 (2011).
21. Ramakrishna, S. et al. Surrogate reporter-based enrichment of cells containing RNA-guided Cas9 nuclease-induced mutations. Nature communications 5, 3378 (2014).
22. Wang, T., Wei, J. J., Sabatini, D. M. & Lander, E. S. Genetic screens in human cells using the CRISPR-Cas9 system. Science 343, 80-84 (2014).
23. Yuan, P. et al. Chondroitin sulfate proteoglycan 4 functions as the cellular receptor for *Clostridium difficile* toxin B. Cell Res 25, 157-168 (2015).
24. Yang, J. et al. ULtiMATE System for Rapid Assembly of Customized TAL Effectors. PLoS One 8, e75649 (2013).
25. Perez, E. E. et al. Establishment of HIV-1 resistance in CD4+ T cells by genome editing using zinc-finger nucleases. Nat Biotechnol 26, 808-816 (2008).
26. Kim, H. J., Lee, H. J., Kim, H., Cho, S. W. & Kim, J. S. Targeted genome editing in human cells with zinc finger nucleases constructed via modular assembly. Genome Res 19, 1279-1288 (2009).
27. Lackner, D. H. et al. A generic strategy for CRISPR-Cas9-mediated gene tagging. Nature communications 6, 10237 (2015).
28. Auer, T. O. & Del Bene, F. CRISPR/Cas9 and TALEN-mediated knock-in approaches in zebrafish. Methods (2014).

29. Li, K., Wang, G., Andersen, T., Zhou, P. & Pu, W. T. Optimization of Genome Engineering Approaches with the CRISPR/Cas9 System. PLoS One 9, e105779 (2014).
30. Orlando, S. J. et al. Zinc-finger nuclease-driven targeted integration into mammalian genomes using donors with limited chromosomal homology. Nucleic Acids Res 38, e152 (2010).
31. Sakuma, T., Nakade, S., Sakane, Y., Suzuki, K. T. & Yamamoto, T. MMEJ-assisted gene knock-in using TALENs and CRISPR-Cas9 with the PITCh systems. Nat Protoc 11, 118-133 (2016).
32. Nakade, S. et al. Microhomology-mediated end-joining-dependent integration of donor DNA in cells and animals using TALENs and CRISPR/Cas9. Nature communications 5, 5560 (2014).
33. Cristea, S. et al. In vivo cleavage of transgene donors promotes nuclease-mediated targeted integration. Biotechnol Bioeng 110, 871-880 (2013).
34. Chen, F. et al. High-frequency genome editing using ssDNA oligonucleotides with zinc-finger nucleases. Nat Methods 8, 753-755 (2011).
35. Potter, C. J. & Luo, L. Splinkerette PCR for mapping transposable elements in *Drosophila*. PLoS One 5, e10168 (2010).
36. Uren, A. G. et al. A high-throughput splinkerette-PCR method for the isolation and sequencing of retroviral insertion sites. Nat Protoc 4, 789-798 (2009).
37. Yin, B. & Largaespada, D. A. PCR-based procedures to isolate insertion sites of DNA elements. Biotechniques 43, 79-84 (2007).
38. Peng, J., Zhou, Y., Zhu, S. & Wei, W. High-throughput screens in mammalian cells using the CRISPR-Cas9 system. FEBS J 282, 2089-2096 (2015).

The invention claimed is:

1. A universal donor construct being a linear donor DNA or being cleavable in a cell to produce a linear donor DNA, wherein the linear donor DNA, from its middle to both ends, sequentially comprises: an expression cassette; a sequence extension consisting of a reverse termination codon located at the 5'-end of the expression cassette and a sequence extension consisting of a forward termination codon located at the 3'-end of the expression cassette; a universal target sequence located at the 5'-end and/or 3'-end, comprising a target site cleavable by a Cas9 nuclease; and protective sequences located at both ends;
   wherein the expression cassette comprises a promoter-driven marker gene; and
   wherein the universal target sequence is absent in a cell genome to be subjected to a gene knockout.

2. The universal donor construct of claim 1, which is a linear donor DNA.

3. The universal donor construct of claim 1, wherein the protective sequence is 5-30 bp.

4. A method for generating a gene knockout in a cell, comprising the steps of:
(1) introducing into the cell:
  (a) a Cas9 nuclease;
  (b) a gRNA that recognizes a specific target sequence in a cell genome;
  (c) a universal donor construct, wherein the universal donor construct is a linear donor DNA or is cleavable in a cell to produce a linear donor DNA, and the linear donor DNA, from the middle to both ends, sequentially comprises: an expression cassette; a sequence extension consisting of a reverse termination codon located at the 5'-end of the expression cassette and a sequence extension consisting of a forward termination codon located at the 3'-end of the expression cassette; a universal target sequence located at the 5'-end and/or 3'-end, comprising a target site cleavable by a Cas9 nuclease; and protective sequences located at both ends;
   wherein the expression cassette comprises a promoter-driven marker gene; and
   wherein the universal target sequence is absent in the cell genome to be subjected to a gene knockout; and
  (d) a gRNA that recognizes the universal target sequence contained in the linear donor DNA;
(2) inserting the linear donor DNA into a specific target site in the cell genome by non-homologous end joining; and
(3) screening cells positive for the marker expression.

5. The method of claim 4, wherein the universal donor construct is a linear donor DNA.

6. The method of claim 4, wherein the gRNA that recognizes the specific target sites in the cell genome is one kind of gRNA, or more than one kind of gRNA that recognize different target sites in the cell genome.

7. The method of claim 4, wherein the marker gene is an antibiotic resistance gene or a fluorescent protein gene.

8. A system or kit for a gene knockout, comprising:
   (1) a Cas9 nuclease or a vector or cell capable of expressing the Cas9 nuclease;
   (2) a gRNA that recognizes a specific target sequence in a cell genome;
   (3) a universal donor construct, wherein the universal donor construct is a linear donor DNA or is cleavable in a cell to produce a linear donor DNA, and the linear donor DNA, from the middle to both ends, sequentially comprises: an expression cassette; a sequence extension consisting of a reverse termination codon located at the 5'-end of the expression cassette and a sequence extension consisting of a forward termination codon located at the 3'-end of the expression cassette; a universal target sequence located at the 5'-end and/or 3'-end, comprising a target site cleavable by a Cas9 nuclease; and protective sequences located at both ends;
   wherein the expression cassette comprises a promoter-driven marker gene; and
   wherein the universal target sequence is absent in the cell genome to be subjected to a gene knockout; and
   (4) a gRNA that recognizes the universal target sequence in the linear donor DNA.

9. The system or kit of claim 8, wherein the universal donor construct is a linear donor DNA.

10. The system or kit of claim 9, wherein the marker gene is an antibiotic resistance gene or a fluorescent protein gene.

11. The universal donor construct of claim 2, which is a double-stranded linear donor DNA.

12. The universal donor construct of claim 2, wherein the linear donor DNA only has the universal target sequence at the 5'-end or the 3'-end.

13. The universal donor construct of claim 2, wherein the marker gene is an antibiotic resistance gene or a fluorescent protein gene.

14. The universal donor construct of claim 3, wherein the protective sequence is 20 bp, in length.

15. The universal donor construct of claim 3, wherein the universal target sequence comprises 5'-GTACGGGGCGATCATCCACA-3' or 5'-AATCGACTCGAACTTCGTGT-3'.

16. The method of claim 5, wherein the universal donor construct is a double-stranded linear donor DNA.

17. The method of claim 5, wherein the linear donor DNA only has the universal target sequence at the 5'-end or the 3'-end.

18. The method of claim 6, wherein the gRNA that recognizes the specific target sequence in the cell genome is an sgRNA, and/or the gRNA that recognizes the universal target sequence in the linear donor DNA is an sgRNA.

19. The method of claim 18, wherein the sgRNA that recognizes the specific target site in the cell genome and the sgRNA that recognizes the universal target sequence in the linear donor DNA are located in the same vector; or the sgRNA that recognizes the specific target site in the cell genome and the sgRNA that recognizes the universal target sequence in the linear donor DNA are located in different vectors.

20. The method of claim 7, wherein the cells are screened by drug resistance, or the cells are screened by a FACS method.

21. The method of claim 7, wherein the protective sequence is 5-30 bp in length.

22. The method of claim 21, wherein the protective sequence is 20 bp in length.

23. The method of claim 7, wherein the universal target sequence comprises 5'-GTACGGGGCGATCATCCACA-3' or 5'-AATCGACTCGAACTTCGTGT-3'.

24. The system or kit of claim 9, wherein the universal donor construct is a double-stranded linear donor DNA.

25. The system or kit of claim 9, wherein the linear donor DNA only has the universal target sequence at the 5'-end or the 3' end.

26. The system or kit of claim 9, wherein the gRNA that recognizes the specific target site in the cell genome is one kind of gRNA, or more than one kind of gRNA that recognize different target sites in the cell genome.

27. The system or kit of claim 9, wherein the gRNA that recognizes the specific target sequence in the cell genome is an sgRNA, and/or the gRNA that recognizes the universal target sequence in the linear donor DNA is an sgRNA.

28. The system or kit of claim 27, wherein the sgRNA that recognizes the specific target sequence in the cell genome and the sgRNA that recognizes the universal target sequence in the linear donor DNA are located in the same vector; or the sgRNA that recognizes the specific target sequence in the cell genome and the sgRNA that recognizes the universal target sequence in the linear donor DNA are located in different vectors.

29. The system or kit of claim 10, wherein the protective sequence is 20 bp in length.

30. The system or kit of claim 10, wherein the universal target sequence comprises 5'-GTACGGGGCGATCATCCACA-3' or 5'-AATCGACTCGAACTTCGTGT-3'.

31. The universal donor construct of claim 2, wherein the linear donor DNA has the universal target sequence at both of the 5'-end and the 3'-end.

32. The method of claim 5, wherein the linear donor DNA has the universal target sequences at both of the 5'-end and the 3'-end.

33. The system or kit of claim 9, wherein the linear donor DNA has the universal target sequences at both of the 5'-end and the 3'-end.

* * * * *